United States Patent [19]

Fukumaru et al.

[11] 3,995,059
[45] Nov. 30, 1976

[54] PHARMACEUTICAL COMPOSITIONS CONTAINING FATTY ACID AMIDE DERIVATIVES

[75] Inventors: Toshitsugu Fukumaru, Kyoto; Noritaka Hamma, Nishinomiya; Hiroshi Nakatani, Toyonaka; Hideaki Fukushima; Katsuyuki Toki, both of Nishinomiya, all of Japan

[73] Assignee: Sumitomo Chemical Company, Limited, Osaka, Japan

[22] Filed: Aug. 23, 1971

[21] Appl. No.: 174,149

Related U.S. Application Data

[62] Division of Ser. No. 671,228, Sept. 28, 1967, abandoned.

[30] Foreign Application Priority Data

| Oct. 4, 1966 | Japan | 41-65504 |
|---|---|---|
| Oct. 12, 1966 | Japan | 41-67326 |
| Oct. 14, 1966 | Japan | 41-67672 |
| Nov. 2, 1966 | Japan | 41-72548 |
| Nov. 4, 1966 | Japan | 41-72770 |
| Nov. 4, 1966 | Japan | 41-72772 |
| Dec. 1, 1966 | Japan | 41-79092 |
| Oct. 5, 1966 | Japan | 41-65792 |
| Oct. 13, 1966 | Japan | 41-67618 |
| Oct. 14, 1966 | Japan | 41-67673 |
| Nov. 2, 1966 | Japan | 41-72549 |
| Nov. 4, 1966 | Japan | 41-72771 |
| Nov. 4, 1966 | Japan | 41-72773 |
| Dec. 1, 1966 | Japan | 41-79093 |
| Dec. 1, 1966 | Japan | 41-79095 |
| Dec. 2, 1966 | Japan | 41-79212 |
| Dec. 3, 1966 | Japan | 41-79486 |
| Dec. 15, 1966 | Japan | 41-82478 |
| Mar. 31, 1967 | Japan | 42-20644 |
| June 2, 1967 | Japan | 42-35424 |
| June 7, 1967 | Japan | 42-36653 |
| July 20, 1967 | Japan | 42-46974 |
| July 22, 1967 | Japan | 42-47330 |
| July 26, 1967 | Japan | 42-48371 |

[52] U.S. Cl. .............................. 424/324; 424/320; 260/404

[51] Int. Cl.$^2$ .................. A01N 9/20; A01N 9/24
[58] Field of Search ............ 424/320, 324; 260/404

[56] References Cited
UNITED STATES PATENTS

| 3,250,794 | 5/1966 | Mod et al. | 260/404 |
|---|---|---|---|
| 3,551,462 | 12/1970 | Seki et al. | 260/404 |
| 3,621,043 | 11/1971 | Seki et al. | 260/404 |

*Primary Examiner*—Albert T. c Meyers
*Assistant Examiner*—D. W. Robinson
*Attorney, Agent, or Firm*—Stevens, Davis, Miller & Mosher

[57] ABSTRACT

A pharmaceutical composition consisting essentially of pharmaceutically effective amount of an N-substituted fatty acid amide of the formula,

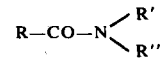

wherein R is a $C_{13} - C_{25}$ aliphatic hydrocarbon chain or a $C_{13} - C_{25}$ hydroxylated aliphatic hydrocarbon chain and RCO— is other than isostearoyl; R' is d- or l-α-$C_1 - C_4$ alkylbenzyl, racemic-, d- or l-α-$C_1 - C_4$ alkylbenzyl substituted in the benzene ring with one or two substituents selected from the group consisting of $C_1 - C_4$ alkyl, $C_1 - C_4$ alkoxy, halogen and nitro, or racemic-, d- or l-α-benzylbenzyl; R" is hydrogen; or R' and R" together are cyclohexyl; and when RCO— is isostearoyl R' is alkyl, alkenyl, cycloalkyl, alkylcycloalkyl, hydroxycycloalkyl, alkoxycycloalkyl, alkylphenyl, hydroxyphenyl, alkoxyphenyl, halogenophenyl, halogen-alkyl-substituted phenyl, halogenoalkyl- and halogen-substituted phenyl, alkoxy- and halogen-substituted phenyl, benzyl, racemic-, d- or l-α-$C_1 - C_4$ alkylbenzyl, benzyl substituted in the benzene ring with lower alkyl or lower alkoxy, racemic-, d- or l-α-benzylbenzyl or hydroxybenzyl, and R" is hydrogen or any one of the groups represented by R', and a pharmaceutically acceptable carrier, which is useful for lowering elevated levels of cholesterol in the blood.

2 Claims, No Drawings

PHARMACEUTICAL COMPOSITIONS CONTAINING FATTY ACID AMIDE DERIVATIVES

CROSS REFERENCE TO THE RELATED APPLICATION

This is the divisional application of the U.S. Ser. No. 671,228 filed on Sept. 28, 1967 now abandoned.

The present invention relates to cholesterol-lowering agents. More particularly, it relates to agents which are useful for the lowering of elevated levels of cholesterol in the blood.

Atherosclerosis, which is a form of simple intimal arteriosclerosis, is an adult disease for which there is no known satisfactory cure. Although the cause of atherosclerosis is not yet known, in spite of discussions in the academic world, it has broadly been recognized that one of the most significant histopathological manifestations of atherosclerosis is the deposition of lipids in the blood. Accordingly, research has been directed to the disturbed metabolism of lipids, and attenuation has been given to the extraordinarily elevated level of cholesterol in the blood.

A number of experimental and clinical facts have been reported which indicate the relationship between atherosclerosis and elevated blood cholesterol level. Hence, the development of agents to reduce the elevated blood cholesterol level is extremely important for the prevention of atherosclerosis.

Concentrated efforts have heretofore been made for the development of such agents for lowering cholesterol and a number of compounds have been tested clinically, but none of them have proved to be completely satisfactory. Some are fairly effective but produce harmful side effects which are not negligible, and others have inadequate effectiveness, so that they require to be administered in large doses.

A group of compounds practically employed nowadays for the above purposes comprises unsaturated fatty acids, especially linoleic acid. The reason why linoleic acid is employed is because of its harmlessness to the human body. However, its effectiveness is not very high and it is uncertain and indefinite. Accordingly, large doses are required to obtain at least appreciable efficacy as a cholesterol-lowering agent.

We have found a group of compounds which are effective as cholesterol-lowering agents and are substantially non-toxic.

In accordance with this invention there is provided a cholesterol-lowering agent comprising an N-substituted fatty acid amide having the formula,

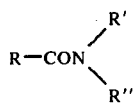

(I)

wherein R is a $C_{13}$–$C_{25}$, branched or straight, saturated or unsaturated, synthetic or natural aliphatic chain having or not having OH group. Examples of RCO are the residues of following fatty acids, in the case of saturated acids, myristic acid, palmitic acid, stearic acid, isostearic acids, arachidic acid, behenic acid, lignoceric acid, cerotic acid and montanic acid; and in the case of unsaturated acids, residues of tsuzuic acid, physetoleic acid, myristoleic acid, zoomaric acid, palmitoleic acid, petroselinic acid, oleic acid, elaidic acid, vaccenic acid, gadoleic acid, erucic acid, brassidic acid, selacholeic acid, linoleic acid, linolenic acid, eleostearic acid, ricinoleic acid, parinaric acid, arachidonic acid, eicosatetraenoic acid. eicosapentaenoic acid, docosapentaenoic acid, hemp-seed oil fatty acid, linseed oil fatty acid, perilla oil fatty acid, styrax oil fatty acid, oiticica oil fatty acid, kayo oil fatty acid, walnut oil fatty acid, poppy-seed oil fatty acid, safflower oil fatty acid, water melon-seed oil fatty acid, soybean oil fatty acid, sunflower oil fatty acid, rice bran oil fatty acid, pumpkin-seed oil fatty acid, kaoliang oil fatty acid, sesame oil fatty acid, corn oil fatty acid, rape oil fatty acid, cottonseed oil fatty acid, olive oil fatty acid, cashew oil fatty acid, tsubaki oil fatty acid, ergot oil fatty acid, castor oil fatty acid, peanut oil fatty acid, palm oil fatty acid, palm kernel oil fatty acid, coconut oil fatty acid, beef tallow fatty acid, lard fatty acid, bone oil fatty acid, horse fat fatty acid, locust oil fatty acid, crystalis oil fatty acid, shark oil fatty acid, cuttlefish oil fatty acid, sardine oil fatty acid, horse-mackerel oil fatty acid, mackerel oil fatty acid, saury pike oil fatty acid, herring oil fatty acid, saurel oil fatty acid, cod oil fatty acid, trout oil fatty acid, gray mullet oil fatty acid, tunny oil fatty acid, menuke oil fatty acid, menhaden oil fatty acid, flatfish oil fatty acid, eel oil fatty acid, various kinds of whale oil fatty acid, body oil fatty acid, skin oil fatty acid, head oil fatty acid, liver oil fatty acid, residual oil fatty acid and egg oil fatty acid and the like plant, land or marine animal oils. In addition on thereto, double bond position isomers or stereoisomers thereof may also be used.

Of the above acids, if desired, saturated fatty acid can be removed roughly from the natural fatty acids according to a suitable method such as, for example, cooling method, urea method, recrystallization method, metal salt method, distillation method and the like.

Further, in the above formula, R' is a d- or l-α-lower alkylbenzyl group, a racemic, d- or l-α-substituted lower alkylbenzyl group having substituents on the benzene ring such as lower alkyl group, halogen atom, lower alkoxy group or nitro group, a racemic, d- or l-α-benzylbenzyl group or adamantyl group, R" is a hydrogen atom or R' and R" are cyclohexyl group, in the case which RCO is an isostearoyl group, R' represents, in addition to the above, an alkyl, alkenyl, cycloalkyl, alkylcycloalkyl, hydroxycycloalkyl, alkoxycycloalkyl, alkylaryl, hydroxyaryl, alkoxyaryl, halogenoaryl, halogenoalkylaryl, halogenoalkyl-halogenoaryl, alkoxyhalogenoaryl, aralkyl, alkylaralkyl, hydroxyaralkyl, alkoxyaralkyl or rac-α-lower alkylaralkyl; and R" is a hydrogen atom, any one of the groups represented by R', or a heterocyclic ring group (having 7 or less carbon atoms) which is constituted by NR'R" containing or not containing oxygen atom.

The starting amines are d- or l-optical isomers of α-lower alkylbenzylamines such as d- or l-α-methylbenzylamine, d- or l-α-ethylbenzylamine, d- or l-α-propyl (n- or i-) benzylamine and d- or l-α-butyl (n-, i- or t-) benzylamine groups, and such racemi, d- or l-amines as α-lower alkylbenzylamine derivatives substituted in the α-position by a lower alkyl group such as a methyl, ethyl, n-propyl, i-propyl, n-butyl, i-butyl or t-butyl group, and also having radicals in phenyl radical such as one or more members of halogen atoms such as fluorine, chlorine, bromine and iodine atoms, lower alkyl groups such as methyl, ethyl, n-propyl, i-propyl, n-butyl, i-butyl and t-butyl groups; lower alkoxy groups such as methoxy, ethoxy, n-propoxy, i-apropoxy, n-butoxy, i-butoxy and t-butoxy; and $NO_2$ radical. These optically active amines can be easily resolved, by the method described in, for example, "Journal of the Chemical Education," Vol. 42, page 296, from racemic amines synthesized according to the process set forth in, for example, "Bulletin de Societe Chimie de Belgiuml" Vol. 72 pages 195–207. Further, rac-, d- and l-α-benzylbenzylamines can be readily resolved according to the process disclosed in "J. Prackt. Chem.," [2] 101, 297 (1921).

In addition thereto, dicyclohexylamines and adamantylamines may also be used.

In the case of isostearoyl amides, there are used, in addition to the above-mentioned amines, mono- or di-alkylamins such as mono- or di-methylamine, mono- or di-ethylamine, mono- or di-n-propylamine, mono- or di-i-propylamine, mono- or di-n-butylamine, mono- or di-i-butylamine, mono- or di-t-butylamine, mono- or di-dodecylamine, mono- or di-palmitylamine, mono- or di-stearylamine, and the like, the mono- or di-alkenylamines such as mono- or di-acrylamine, mono- or di-arylamine, mono- or di-crotonylamine, mono- or di-oleylamine, mono- or di-lineoleylamine, mono- or di-linoleylamine, and the like. Cycloalkylamines such as mono- or di-cyclopentylamine, cyclohexylamine and mono- or dicycloheptylamine, and said cycloalkylamines substituted by one or more members of lower alkyl groups such as methyl, ethyl, n-propyl, i-propyl, n-butyl, i-butyl and t-butyl; hydroxyl groups; lower alkoxy groups such as methoxy, ethoxy, n-propoxy, i-propoxy, n-butoxy, i-butoxy and t-butoxy groups; and N-substituted methyl, ethyl, n-propyl, i-propyl, n-butyl, i-butyl and t-butyl groups. Aromatic amines such as diphenylamines or aniline substituted by one or more members of hydroxyl groups; alkyl groups such as methyl, ethyl, n-propyl, i-propyl, n-butyl, i-butyl and t-butyl; halogen atoms such as chlorine, fluorine, bromine and iodine atoms; $CF_3$; and alkoxy groups such as methoxy, ethoxy, n-propoxy, i-propoxy, n-butoxy, i-butoxy and t-butoxy groups. Anilines substituted by lower alkyl groups such as N-methyl, N-ethyl, N-n-propyl, N-i-propyl, N-n-butyl, N-i-butyl and N-t-butyl. Substituted arylamine comprising N-lower alkylanilines substituted by the above-mentioned substituents. Heterocyclic amines such as pyrrole, pyrrolidine, morpholine, piperidine and hexamethyleneimine. Such amines as benzylamine and dibenzylamine or said amines substituted by one or more members of hydroxyl groups, lower alkyl groups such as methyl, ethyl, n-propyl, i-propyl, n-butyl, i-butyl and t-butyl; alkoxy groups such as methoxy, ethoxy, n-propoxy, i-propoxy, n-butoxy, i-butoxy and t-butoxy groups; α-substituted lower alkyl groups such as racemic α-methyl, α-ethyl, α-n-propyl, α-i-propyl, α-n-butyl, α-i-butyl and α-t-butyl groups; and N-substituted lower alkyl groups such as N-methyl, N-ethyl, N-n-propyl, N-i-propyl, N-n-butyl, N-i-butyl and N-t-butyl groups.

In the present invention, the isostearic acids signify stearic acids having side chains such as 3-, 4-, 5- to 16-methylheptadecanoic acids. However, these acids and other $C_{18}$ acids having side chains should be included in the present invention. These substances are free from double bonds and hence have such advantages that they are relatively unsusceptible to oxidation.

For the production of the present N-substituted acid amides may be used any of the processes known for the preparation of acid amides.

For example, (1) a fatty acid of the formula, is made RCOOH to react directly with an amine of the formula,

in the presence or absence of such dehydrating agent as a di-substituted carbodiimide compound, p-toluenesulfonic acid or p-toluenesulfonyl chloride or the like in an aqueous or organic solvent, (2) a fatty acid of the formula, RCOOH is converted to acid halide of the formula, RCOX, wherein X is a halogen atom, (Organic Synthesis Vol. 37, page 56) and the resulting acid chloride is brought into contact with at least an equimolar amount of the amine of the formula

in the presence of a basic condensing agent, (3) a lower alkyl ester or glyceride of a fatty acid of the formula, ROOCH is made to react directly with the amine of the formula,

in the presence or absence of a solvent and condensing agent or (4) a mixed acid anhydride of a fatty acid of the formula, RCOOH, having the formula,

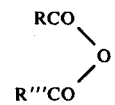

wherein R''' is an alkyl or hologenoalkyl having 1 to 4 carbons, is made to react with the amine of the formula,

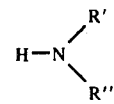

in the presence of a basic condensing catalyst, in the above (1) to (4) processes the R, R' and R'' are the same meanings as defined before. The processes (1) to (4) will be more fully explained below. (1) (a) There have already been various researches wherein dicyclohexyl carbodiimide is used in synthesizing polypeptide. But there has never been a report that an amide is synthesized by using such higher fatty acid to produce an antiatherosclerosis agent, and therefore the process of the present invention is significant. Especially, the process of the present invention can be said to be very advantageous because of the fact that the desired product is readily isolated by filtering and separating the urea precipitated when the reaction has been completed, without any special operation and that the said urea can be used again after being regenerated by such treatment as dehydration.

For the di-substituted carbodiimide to be used in the process of the present invention, there may be exemplified dicyclohexylcarbodiimide, diisopropylcarbodiimide, diphenylcarbodiimide and any other dialkyl-, dicyclalkyl- or di-substituted phenyl-carbodiimide. Any of them is equally useful in the process of the present invention.

In carrying out the process, a fatty acid, a corresponding amine and di-substituted carbodiimide, for example, are separately dissolved in an organic solvent, for example, such aromatic hydrocarbon organic solvent as benzene or toluene, such hydrocarbon solvent as n-hexane, cycloalkane, petroleum ether or gasoline, such ether solvent as dioxane, ether or tetrahydrofuran or such alkyl halide solvent as chloroform, ethylene dichloride or carbon tetrachloride or such ester solvent as methyl, ethyl, propyl or butylacetate. These solutions are mixed at once at the room temperature or under cooling when heat generation is severe so as to be of about 1 in the mole ratio, and the mixture is stirred as required and is then allowed to stand at room temperature for about 3 to 24 hours, whereupon the corresponding urea which is a by-product of the reaction will be precipitated. After the precipitates are filtered off, the desired product will be able to be obtained from the filtrate. Further, the excess di-substituted carbodiimide may be decomposed with acetic acid or the like as required.

The recovered urea is dehydrated and the resulting carbodiimide is usable again for the main reaction.

(b) The above-mentioned fatty acid and amine are dissolved in a suitable solvent such as, benzene, toluene, xylene, chloroform or carbon tetrachloride and the like. To the solution is added sulfuric acid, phenolsulfonic acid, p-toluenesulfonic acid, p-toluenesulfonylchloride, or an acidic or basic ion-exchange resin, e.g. IRA-400, IR-50 or IR-120 or Amberlist 15, 21, 26 or 27 as a dehydrating agent. Subsequently, the solution is heated using a water separator to separate and remove the water generated. Thereafter, the solvent is removed and the resultant is purified, whereby a desired product can be obtained in a high yield and in a simple manner. Alternatively, the desired object of the present process may sufficiently be achieved by merely heating the solution in the presence of a dehydrating agent, using as the solvent a tertiary oganic amine such as pyridine, picoline or lutidine, besides the above-mentioned solvent.

c. Thermal dehydration process:
The aforesaid fatty acid and amine are heated at about 130°–300° C. for several hours to several 10 hours, if necessary in the presence of an acid catalyst such as boric acid, whereby a desired product is obtained. In this case, water generated may be removed out of the reaction system or the reaction can be carried out in an autoclave to maintain the higher temperature.

2. The reaction for condensing an organic amine with an acid halide is also known. However, so far as we know, there has been no report on the production of antiatherosclerosis agents by utilizing this process. We have found that, by using this process, an amide derivative which is useful as an antiatherosclerosis agent can be obtained at a favorable yield under a mild nonoxidative condition.

Even when an excess of such basic condensing agent as such caustic alkali as caustic lithium soda or potash, such alkaline earth hydroxide as calcium or barium hydroxide, such alkali carbonate as lithium, sodium or potassium carbonate, such alkaline earth carbonate as calcium or barium carbonate, such tertiary amine as trimethylamine, triethylamine dimethylaniline, pyridine, picoline, anion exchange resin or an excess of the starting amine or any of the above-mentioned amines is used, the object of the invention will be able to be attained.

As for the solvent in this reaction, is used water, such organic ketone as acetone, methylethyl ketone or methylisobutyl ketone, such ester as methyl acetate, ethyl acetate, propyl acetate or butyl acetate, such other as ethyl ether, propyl ether, tetrahydrofuran or dioxane, such hydrocarbon solvent as n-hexane, cyclohexane, benzene or toluene, such alkyl halide as ethylene dichloride, chloroform or carbon tetrachloride, such as tertiary amine as dimethyl formamide, pyridine or picoline or any of the starting material amines as alone or as properly mixed.

Any temperature from the freezing point up to near the boiling point of the solvent used can be applied to the reaction. Further, it is desirable that the reaction is conducted in a stream of such inert gas as nitrogen or helium.

3. a. Process using glycerides:
The aforesaid oil glyceride and an equimolar amount of an amine are mixed with a basic catalyst such as, sodium methylate, soldium ethylate, potassium butylate, potassium hydroxide or sodium hydroxide and the like, or with an acidic catalyst such as ammonium chloride or boric acid and the like, and the mixture is heated at about 50° – 300° C. for 30 minutes to several ten hours to obtain a desired product. Even in the absence of the basic or acidic catalyst, the desired product can be obtained in a favorable yield when the amine is used in excess. In this case, the object can be achieved either in the presence or absence of an inert organic solvent.

b. Process using esters:
An ester of the aforesaid fatty acid or of a fatty acid mixture obtained from the aforesaid oils or fats is mixed with an amine, and the mixture is heated at about 100° – 300° C. for 30 minutes to several 10 hours either in the presence or absence of the above-mentioned basic or acidic catalyst and of an inert organic solvent, whereby the object of the present process can be achieved. In this case, an alcohol formed may be removed out of the reaction system or an autoclave may be used.

The reactions of both processes (a) and (b) mentioned above should be done in an inert gas such as nitrogen to inhibit the formation of peroxides, coloring matters and the like undesirable by-products.

4. The reaction of mixed anhydride method which is carried out at a low temperature is substantially complete at a low temperature is substantially complete at about 0° C. Unsaturated fatty acid derivatives, in particular, are unstable substances which, under certain conditions undergo oxidation, polymerization, position or geometrical isomerization and the like due to heat and air. Therefore, the process for producing unsaturated fatty acid amide derivatives according to the present invention, which is a low temperature reaction, has found a great significance to attain excellent results.

The solvents employed in the present reaction include ether, dioxane, tetrahydrofuran, dichloromethane, chloroform, carbon, tetrachloride, methyl acetate, ethyl acetate, benzene, toluene, xylene, acetone and methylisobutylketone. As the basic materials, organic solvent-soluble tertiary amines such as trimethylamine, triethylamine, dimethylaniline, diethylaniline and pyridine and the like are desirably used. In some cases, however, inorganic bases, such as potassium carbonate and sodium carbonate, or basic ion exchange resins may also be used.

In order to prepare said mixed acid having 1 to 4 carbon atoms ester is reacted with a fatty acid of the formula, RCOOH wherein R is the same meanings as identified above. Examples of the said lower alkyl halogeno acid ester include chloroformate, and acetate.

The chloroformate, and acetate to be employed are methyl chloroformate, acetate, ethyl chloroformate, acetate and butyl chloroformate, acetate and the like.

The effectiveness of the compounds was tested by using mice fed on a specific diet which was enriched with cholesterol and bile acids. The blood cholesterol level of the mice had been raised to 3 to 6 times as high as the normal level. The amide compound as well was mixed with the specific diet in an amount of 0.2%, and continuously administered orally for 8 to 12 days. Then the total cholesterol value in the blood serum of the animals was evaluated. During the tests, unfavourable side effects, such as the prevention of body weight gain and others, were not observed. It is noted that the stated compound is superior to linoleic acid. Moreover, in the linoleic acid-administered group, ineffective cases were sometimes observed due to the individual difference of the animals, and the effectiveness varied considerably even in the same individual animal. While, it should be emphasized that no such phenomena were observed in the acidamide administered group.

Another significant effect of the N-substituted acidamide compounds according to the present invention is to prevent the deposition of cholesterol and fat in the liver, which occurs in animals fed on a diet rich in cholesterol. It seems that the linoleamide compounds improve the declined lipid-metabolism function of the liver. This effectiveness is also favorable, in view of the fact that the metabolism of lipid mainly relies upon the function of the liver. In the administration of linoleic acid, such effectiveness is never observed. The results are shown in Table 1.

The extremely low toxicities of the present acidamide compounds are illustrated in Table 2, in which the acute toxicities of some of the present compounds in mice are listed.

Table 1

| | Compound | Serum cholesterol mg % | Liver cholesterol mg/100 g. |
|---|---|---|---|
| [I] | Control (no compound added) | 546 | 3585 |
| | Linoleic acid | 324 | 4585 |
| | (+) N-(α-Methylbenzyl)-linoleamide | 267 | 764 |
| | (+) N-(α-Methylbenzyl)-oleamide | 288 | 797 |
| | (+) N-(α-Methylbenzyl)-linolenamide | 269 | 784 |
| | (+) N-(α-Methylbenzyl)-isostearamide | 251 | 761 |
| | Safflower oil (+)α-methylbenzylamide | 273 | 790 |
| | Soybean oil (+)α-methylbenzylamide | 280 | 805 |
| | Linseed oil (+)α-methylbenzylamide | 291 | 796 |
| | Cod oil (+)α-methylbenzylamide | 251 | 743 |
| | Cuttlefish oil (+)α-ethylbenzylamide | 248 | 748 |
| | Cotton seed oil (+)α-propylbenzylamide | 262 | 800 |
| [II] | Control (no compound added) | 521 | 3308 |
| | Linoleic acid | 329 | 4491 |
| | (−) (α-Methylbenzyl)-linoleamide | 286 | 908 |
| | (−) (α-Methylbenzyl)-oleamide | 283 | 808 |
| | (−) (α-Methylbenzyl)-linolenamide | 253 | 767 |
| | (−) (α-Methylbenzyl)-isostearamide | 246 | 777 |
| | (−) (α-Ethylbenzyl)-linoleamide | 251 | 821 |
| | Safflower oil (−)α-methylbenzylamide | 276 | 898 |
| | Soybean oil (−)α-methylbenzylamide | 274 | 799 |
| | Linseed oil (−)α-methylbenzylamide | 290 | 776 |
| | Sardine oil (−)α-methylbenzylamide | 261 | 744 |
| | Cod oil (−)α-methylbenzylamide | 250 | 739 |
| | $C_{17}H_{33}CONHCH(d)(C_6H_5)$ / $CH_3$ | 290 | 815 |
| | $C_{17}H_{33}CONHCH(l)(C_6H_5)$ / $CH_3$ | 295 | 1330 |
| | $C_{13}H_{27}CONHCH(d)(C_6H_5)$ / $CH_3$ | 302 | 1620 |
| | $C_{13}H_{27}CONHCH(l)(C_6H_5)$ / $CH_3$ | 252 | 1820 |

Table 1-continued

| Compound | Serum cholesterol mg % | Liver cholesterol mg/100 g. |
|---|---|---|
| C$_{15}$H$_{31}$CONHCH(d)(CH$_3$)—C$_6$H$_5$ | 300 | 906 |
| C$_{15}$H$_{31}$CONHCH(l)(CH$_3$)—C$_6$H$_5$ | 314 | 1160 |
| C$_{17}$H$_{31}$CONHCH(d)(C$_2$H$_5$)—C$_6$H$_5$ | 274 | 992 |
| C$_{17}$H$_{31}$CONHCH(l)(C$_2$H$_5$)—C$_6$H$_5$ | 302 | 1042 |
| Safflower oil-CONHCH(d)(C$_3$H$_7$)—C$_6$H$_5$ | 290 | 992 |
| Cuttlefish oil-CONHCH(d)(C$_4$H$_9$)—C$_6$H$_5$ | 277 | 968 |
| [III] Control (no compound added) | 471 | |
| C$_{17}$H$_{31}$CONHCH(CH$_3$)—C$_6$H$_4$—Cl | 225 | 946 |
| C$_{17}$H$_{31}$CONHCH(CH$_3$)—C$_6$H$_3$Cl$_2$ | 315 | 856 |
| C$_{17}$H$_{31}$CONHCH(CH$_3$)—C$_6$H$_4$—OCH$_3$ | 385 | 1511 |
| C$_{17}$H$_{31}$CONHCH(CH$_3$)—C$_6$H$_4$—Br | 322 | 1341 |
| C$_{17}$H$_{31}$CONHCH(C$_2$H$_5$)—C$_6$H$_4$—CH$_3$ | 242 | 1065 |
| C$_{17}$H$_{31}$CONHCH(d)(CH$_3$)—C$_6$H$_4$—CH$_3$ | 237 | 1047 |
| [IV] Control (no compound added) | 595 | 3145 |
| C$_{17}$H$_{31}$CONHCH(CH$_3$)—C$_6$H$_4$—CH$_3$ | 240 | 828 |
| C$_{17}$H$_{31}$CONHCH(C$_2$H$_5$)—C$_6$H$_4$—CH$_3$ | 321 | 908 |
| C$_{17}$H$_{31}$CONHCH(d)(CH$_3$)—C$_6$H$_4$—Cl | 217 | 826 |

Table 1-continued

| Compound | Serum cholesterol mg % | Liver cholesterol mg/100 g. |
|---|---|---|
| C₁₇H₃₁CONHCH(CH₃)-C₆H₃(Cl)(Cl) (l) | 251 | 1000 |
| C₁₇H₃₁CONHCH(CH₃)-C₆H₄-OCH₃ (d) | 234 | 1007 |
| iso-C₁₇H₃₅CONHCH(C₂H₅)-C₆H₄-C(CH₃)₃ | 297 | 905 |
| C₁₇H₂₉CONHCH(CH₃)-C₆H₄-CH₃ | 222 | 913 |
| Safflower oil-CONHCH(C₂H₅)-C₆H₄-CH₃ | 216 | 1003 |
| Cuttlefish oil-CONHCH(CH₃)-C₆H₄-CH₃ | 232 | 922 |

[V]
| Compound | Serum | Liver |
|---|---|---|
| Control (no compound added) | 372 | 2640 |
| Linoleic acid | 351 | 3124 |
| C₁₇H₂₉CONH—CH(CH₂-C₆H₅)-C₆H₅ | 238 | 729 |
| C₁₇H₃₁CO " | 214 | 544 |
| d- " | 200 | 500 |
| l- " | 208 | 623 |
| C₁₇H₃₃CO—CH(CH₂-C₆H₅)-C₆H₅ | 245 | 831 |
| d- " | 222 | 729 |
| l- " | 263 | 888 |
| iso-C₁₇H₃₅CO " | 221 | 609 |
| d- " | 209 | 561 |
| l- " | 252 | 639 |
| Safflower oil-CO " | 220 | 575 |
| d- " | 204 | 515 |
| l- " | 253 | 632 |
| Linseed oil-CO " | 249 | 800 |
| Cuttlefish-oil-CO " | 223 | 631 |
| Shark oil-CO " | 248 | 621 |
| Sardine oil-CO " | 231 | 607 |

[VI]
| Compound | Serum | Liver |
|---|---|---|
| Control (no compound added) | 508 | 3270 |
| Linoleic acid | 314 | 4550 |
| Linoleamide | 260 | 784 |
| Linolenamide | 261 | 1071 |
| Isostearamide | 266 | 821 |
| Safflower oil amide (RCON(C₆H₁₁)₂) | 278 | 1081 |
| Cod oil amide | 249 | 920 |
| Cuttlefish oil amide | 258 | 830 |
| Sardine oil amide | 269 | 1005 |

[VII]
| Compound | Serum | Liver |
|---|---|---|
| Control (no compound added) | 508 | 3535 |
| Linoleic acid | 341 | 4550 |

Table 1-continued

| Compound | Serum cholesterol mg % | Liver cholesterol mg/100 g. |
|---|---|---|
| isostearoyl-NH–⬡ | 278 | 1081 |
| isostearoyl-N(–⬡)(–⬡) | 281 | 1053 |
| isostearoyl-NHCH(CH₃)–⬡ | 265 | 1061 |
| isostearoyl-NHCH(CH₃)–⬡–CH₃ | 232 | 868 |
| isostearoyl-NHCH(CH₃)(CH₃) | 290 | 1100 |
| isostearoyl-NH–⬡–OCH₃ | 300 | 1090 |
| [VIII] Control (no compound added) | 472 | 2652 |
| $C_{17}H_{31}$CONHCH(CH₃)–⬡(o-NO₂) | 299 | 1003 |
| $C_{17}H_{31}$CONHCH(CH₃)–⬡(m-NO₂) | 287 | 992 |
| $C_{17}H_{31}$CONHCH(CH₃)–⬡–NO₂ | 340 | 1603 |
| $C_{17}H_{31}$CONHCH(C₂H₅)–⬡–NO₂ | 331 | 980 |
| i-$C_{17}H_{35}$CONHCH(CH₃)–⬡–NO₂ | 294 | 821 |
| i-$C_{17}H_{35}$CONHCH(CH₃)–⬡–NO₂ | 362 | 1305 |
| $C_{17}H_{29}$CONHCH(C₂H₅)–⬡(o-NO₂) | 300 | 1091 |
| $C_{17}H_{33}$CONHCH(CH₃)–⬡(o-NO₂) | 309 | 1113 |

Table 1-continued

| Compound | Serum cholesterol mg % | Liver cholesterol mg/100 g. |
|---|---|---|
| Safflower oil-CONHCH(CH₃)-C₆H₄-NO₂ (o) | 312 | 982 |
| Cuttlefish oil-CONHCH(CH₃)-C₆H₄-NO₂ (m) | 300 | 1502 |
| Cod oil-CONHCH(CH₃)-C₆H₄-NO₂ (o) | 340 | 1403 |
| [IX] Control (no compound added) | 336 | 2200 |
| C₁₇H₃₁CONH-adamantyl | 288 | 721 |
| C₁₇H₃₃CONH-adamantyl | 294 | 1120 |
| C₁₇H₂₉CONH-adamantyl | 279 | 750 |
| iso-C₁₇H₃₅CONH-adamantyl | 280 | 761 |
| Safflower oil-CONH-adamantyl | 292 | 745 |
| Linseed oil-CONH-adamantyl | 300 | 802 |
| Cod oil-CNH-adamantyl | 270 | 777 |
| Sardine oil-CONH-adamantyl | 259 | 758 |
| [X] Control | 554 | 3293 |
| C₁₇H₃₁CONHCH(d)(CH₃)-C₆H₄-CH₃ | 228 | 820 |
| C₁₇H₃₃CONHCH(dl)(CH₃)-C₆H₄-C₂H₅ | 304 | 1010 |

Table 1-continued

| Compound | Serum cholesterol mg % | Liver cholesterol mg/100 g. |
|---|---|---|
| C₁₇H₃₃CONHCH(CH₃)–C₆H₄–C₂H₅ | 398 | 1210 |
| C₁₇H₃₃CONHCH(CH₃)–C₆H₄–C₂H₅ (d) | 254 | 841 |
| iso-C₁₇H₃₅CONHCH(CH₃)–C₆H₄–CH₃ | 308 | 923 |
| C₁₇H₂₉CONHCH(CH₃)–C₆H₄–CH₃ (d) | 249 | 1000 |
| C₁₇H₂₉CONHCH(CH₃)–C₆H₄–CH₃ | 295 | 1015 |
| Safflower oil-CONHCH(CH₃)–C₆H₄–CH₃ (d) | 230 | 841 |
| Safflower oil-CONHCH(CH₃)–C₆H₄–CH₃ | 299 | 1014 |
| Herring oil-CONHCH(CH₃)–C₆H₄–CH₃ (d) | 262 | 823 |
| Herring oil-CONHCH(CH₃)–C₆H₄–CH₃ | 315 | 1022 |
| [XI] Control | 595 | 3451 |
| C₁₇H₃₁CONHCH(CH₃)–C₆H₄–Cl | 230 | 845 |
| C₁₇H₃₁CONHCH(CH₃)–C₆H₄–NO₂ (d) | 275 | 1011 |
| C₁₇H₃₁CONHCH(CH₃)–C₆H₄–NO₂ | 315 | 1098 |
| C₁₇H₃₁CONHCH(CH₃)–C₆H₄–OCH₃ (d) | 325 | 1061 |
| C₁₇H₃₁CONHCH(CH₃)–C₆H₄–OCH₃ | 352 | 1125 |
| C₁₇H₃₃CONHCH(CH₃)–C₆H₄–Br (dl) | 299 | 1039 |
| C₁₇H₃₃CONHCH(CH₃)–C₆H₄–Br (d) | 253 | 921 |

Table 1-continued

| Compound | Serum cholesterol mg % | Liver cholesterol mg/100 g. |
|---|---|---|
| C₁₇H₃₃CONHCH(CH₃)—C₆H₄—Br (l, para) | 277 | 1009 |
| C₁₇H₃₃CONHCH(C₂H₅)—C₆H₄—NO₂ (dl, meta) | 362 | 1342 |
| C₁₇H₃₃CONHCH(C₂H₅)—C₆H₄—NO₂ (d, meta) | 289 | 906 |
| C₁₇H₃₃CONHCH(C₂H₅)—C₆H₄—NO₂ (l, meta) | 315 | 1125 |
| C₁₇H₃₃CONHCH(CH₃)—C₆H₄—OCH₃ (dl, para) | 382 | 1210 |
| C₁₇H₃₃CONHCH(CH₃)—C₆H₄—OCH₃ (d, para) | 306 | 1069 |
| C₁₇H₃₃CONHCH(CH₃)—C₆H₄—OCH₃ (l, para) | 318 | 1115 |
| C₁₇H₃₃CON(cyclohexyl)(CH₂-cyclohexyl) | 309 | 929 |
| iso-C₁₇H₃₅CONHCH(CH₃)—C₆H₄—Cl (dl, para) | 299 | 1068 |
| iso-C₁₇H₃₅CONHCH(CH₃)—C₆H₄—Cl (d, para) | 239 | 906 |
| iso-C₁₇H₃₅CONHCH(CH₃)—C₆H₄—Cl (l, para) | 256 | 929 |
| iso-C₁₇H₃₅CONHCH(CH₃)—C₆H₄—NO₂ (dl, para) | 321 | 1222 |
| iso-C₁₇H₃₅CONHCH(CH₃)—C₆H₄—OCH₃ (dl, para) | 367 | 1191 |
| iso-C₁₇H₃₅CONHCH(CH₃)—C₆H₄—OCH₃ (d, para) | 300 | 949 |

Table 1-continued

| Compound | Serum cholesterol mg % | Liver cholesterol mg/100 g. |
|---|---|---|
| iso-$C_{17}H_{35}$CONHCH(CH$_3$)—C$_6$H$_4$—OCH$_3$ | 333 | 1094 |
| $C_{17}H_{29}$CONHCH(CH$_3$)—C$_6$H$_4$—Cl (dl) | 309 | 1125 |
| $C_{17}H_{29}$CONHCH(CH$_3$)—C$_6$H$_4$—Cl (d) | 275 | 995 |
| $C_{17}H_{29}$CONHCH(CH$_3$)—C$_6$H$_4$—Cl (l) | 300 | 1029 |
| $C_{17}H_{29}$CONHCH(C$_2$H$_5$)—C$_6$H$_4$—NO$_2$ (d) | 245 | 1004 |
| $C_{17}H_{29}$CONHCH(C$_2$H$_5$)—C$_6$H$_4$—NO$_2$ (l) | 365 | 1325 |
| $C_{17}H_{29}$CONHCH(CH$_2$C$_6$H$_5$)—C$_6$H$_5$ (d) | 240 | 623 |
| $C_{17}H_{29}$CONHCH(CH$_2$C$_6$H$_5$)—C$_6$H$_5$ (l) | 275 | 1632 |
| $C_{17}H_{29}$CONHCH(C$_2$H$_5$)—C$_6$H$_4$—OCH$_3$ (dl) | 325 | 1450 |
| $C_{17}H_{29}$CONHCH(C$_2$H$_5$)—C$_6$H$_4$—OCH$_3$ (d) | 280 | 870 |
| $C_{17}H_{29}$CONHCH(C$_2$H$_5$)—C$_6$H$_4$—OCH$_3$ (l) | 339 | 1620 |
| Safflower oil-CONHCH(C$_2$H$_5$)—C$_6$H$_4$—Br (dl) | 350 | 1062 |
| Safflower oil-CONHCH(C$_2$H$_5$)—C$_6$H$_4$—Br (d) | 255 | 823 |
| Safflower oil-CONHCH(C$_2$H$_5$)—C$_6$H$_4$—Br (l) | 372 | 1234 |

Table 1-continued

| Compound | Serum cholesterol mg % | Liver cholesterol mg/100 g. |
|---|---|---|
| Safflower oil-CONHCH(d)(CH₃)—C₆H₄—NO₂ | 270 | 985 |
| Safflower oil-CONHCH(l)(CH₃)—C₆H₄—NO₂ | 291 | 1109 |
| Safflower oil-CONHCH(dl)(CH₃)—C₆H₄—OCH₃ | 378 | 1229 |
| Safflower oil-CONHCH(l)(CH₃)—C₆H₄—OCH₃ | 388 | 1411 |
| Safflower oil-CONHCH(d)(CH₃)—C₆H₄—OCH₃ | 300 | 974 |
| Flatfish oil-CONHCH(dl)(C₂H₅)—C₆H₄—Cl | 365 | 889 |
| Flatfish oil-CONHCH(d)(C₂H₅)—C₆H₄—Cl | 290 | 714 |
| Flatfish oil-CONHCH(l)(C₂H₅)—C₆H₄—Cl | 323 | 1158 |
| Sardine oil-CONHCH(d)(CH₃)—C₆H₄—NO₂ | 275 | 967 |
| Sardine oil-CONHCH(l)(CH₃)—C₆H₄—NO₂ | 339 | 1450 |
| Sardine oil-CONHCH(d)(CH₂—C₆H₅)—C₆H₅ | 222 | 711 |
| Sardine oil-CONHCH(l)(CH₂—C₆H₅)—C₆H₅ | 320 | 1069 |
| Sardine oil-CONHCH(dl)(CH₃)—C₆H₄—OCH₃ | 340 | 1215 |
| Sardine oil-CONHCH(d)(CH₃)—C₆H₄—OCH₃ | 279 | 887 |

Table 1-continued

| Compound | Serum cholesterol mg % | Liver cholesterol mg/100 g. |
|---|---|---|
| Sardine oil-CONHCH(CH₃)—⌬—OCH₃ | 350 | 1309 |

[XII]

| Compound | Blood cholesterol level index % |
|---|---|
| Control | 100 |
| iso-C₁₇H₃₅CONHCH(CH₃)₂ | 62 |
| iso-NHCH₂CH=CH₂ | 58 |
| iso-NH—cyclopentyl | 60 |
| iso-NH—cycloheptyl | 72 |
| iso-NH—C₆H₁₀—OH | 54 |
| iso-NH—C₆H₁₀—OCH₃ | 71 |
| iso-NH—C₆H₁₀—CH₃ | 68 |
| iso-NH—⌬—OH | 42 |
| iso-NH—⌬(o-Cl) | 55 |
| iso-NH—⌬(m-OCH₃) | 63 |
| iso-NH—⌬(m-CF₃) | 62 |
| iso-NHCH₂—⌬—CH₃ | 60 |
| iso-NHCH₂—⌬(o-OH) | 58 |
| iso-NHCH₂—⌬—OCH₃ | 44 |
| iso-N(cyclohexyl)(CH₃) | |

(Note: "iso-" denotes the sardine oil-CO— group shown at the top, with the indicated amine substituent.)

Table 2

| | LD₅₀ (Mouse, P.O.) |
|---|---|
| C₁₇H₃₁CONHCH(d)(C₆H₅)CH₃ | > 50 g/kg |
| C₁₇H₃₁CONHCH(l)(C₆H₅)CH₃ | > 50 g/kg |
| C₁₇H₃₁CONHCH(C₆H₄-CH₃)CH₃ | > 50 g/kg |
| C₁₇H₃₁CONHCH(C₆H₅)CH₂C₆H₅ | > 50 g/kg |
| C₁₇H₃₁CONH-adamantyl | > 50 g/kg |
| iso-C₁₇H₃₅CONHCH(C₆H₅)CH₂C₆H₅ | > 50 g/kg |
| C₁₇H₃₁CONHCH(d)(C₆H₅)CH₂C₆H₅ | > 50 g/kg |
| C₁₇H₃₁CONHCH(l)(C₆H₅)CH₂C₆H₅ | > 50 g/kg |

Further, the present compounds were administered to rabbits in a dose of 200 mg/day together with a cholesterol rich diet to obtain such favorable results as shown below. Serum cholesterol, mg. %.

| Compound | 2 weeks | 4 weeks | 6 weeks | 8 weeks | 10 weeks |
|---|---|---|---|---|---|
| Control | 250 | 563 | 890 | 1150 | 1750 |
| β-Sitosterol | 250 | 438 | 875 | 1063 | 1200 |
| N,N-dicyclohexyl linoleamide | 250 | 120 | 62 | 62 | 65 |
| C₁₇H₃₁CONHCH(C₆H₅)CH₃ | 250 | 130 | 65 | 60 | 52 |

| Compound | Dose | Rabbit serum cholesterol lowering ratio (after 9 weeks) |
|---|---|---|
| Control | 0 | 0% |
| β-Sitosterol | 800 mg/kg/day | 21.2% |
| C₁₇H₃₁CONHCH(C₆H₄-CH₃)CH₃ | 100 mg/kg/day | 60.1% |
| C₁₇H₃₁CONHCH(C₆H₄-CH₃)C₂H₅ | 100 mg/kg/day | 59.2% |
| C₁₇H₃₁CONHCH(d)(C₆H₄-Cl)CH₃ | 100 mg/kg/day | 80.1% |
| C₁₇H₃₁CONHCH(C₆H₃Cl₂)CH₃ | 100 mg/kg/day | 61.5% |
| C₁₇H₃₁CONHCH(C₆H₄-OCH₃)CH₃ | 100/mg/day | 58.3% |
| iso-C₁₇H₃₅CONHCH(C₆H₄-C(CH₃)₃)C₂H₅ | 100 mg/kg/day | 59.4% |
| C₁₇H₂₉CONHCH(C₆H₄-CH₃)CH₃ | 100 mg/kg/day | 54.5% |
| Safflower oil CONHCH(C₆H₄-CH₃)C₂H₅ | 100 mg/kg/day | 60.6% |
| Cuttlefish oil CONHCH(C₆H₄-CH₃)CH₃ | 100 mg/kg/day | 67.3% |

All the products involved in the present invention are novel compounds unknown to the literature.

As is seen from Table 2, no fatal case and no significant toxic symptoms were observed even in such large doses (per os) as 0.5 g. per 10 g., namely 50 g./kg. of the body weight. Also, no significant toxic symptoms, or fatal cases, were observed when the amides in amounts of 1, 0.5 or 0.2% in the diet were administered to mice everyday for three weeks. The appetite was normal and digestive functions were unchanged. When the internal organs were inspected by dissection, there was no appreciable change.

The cholesterol-lowering agents of this invention may be orally administered. Usually the amount orally administered is 0.1 g. –20 g. per day, preferably 0.5 g. –5 g. per day and the administration may be continued for 1 to 5 months, usually for 3 months. The cholesterol-lowering agent may be in any suitable form which is conventional for oral administration. Thus, it may be encased in a capsule, or it may be in a liquid form, in a tablet form, or in a powder form. In preparing the agents in these various forms, the active compound may be mixed with or impregnated in a suitable solid carrier, or it may be mixed with a liquid carrier such as an edible oil, preferably those containing linoleic acid. It is also possible to use a mixture of two or more of the N-substituted amides of the invention. It may also be used as mixed with linoleic acid.

The present invention will be explained in detail with reference to the following examples which are given only for illustration and not for limitation of the invention in any way.

EXAMPLE 1

A mixture of 10 g. of linoleic acid and 5 g. of l(—)α-methylbenzylamine was heated and refluxed for about 8 hours in 300 ml. of toluene in the presence of 0.2 g. of p-toluenesulfonic acid, while using a water separator.

After completion of the reaction, the toluene layer formed was subjected to acid-washing, alkali-washing and water-washing, was dried and was then concentrated to obtain 12.3 g. of a desired product, m.p. 200°–221° C./0.05 mmHg. Elementary analysis:

|       | Theoretical | Analytical |
|-------|-------------|------------|
| C (%) | 81.40       | 81.70      |
| H (%) | 10.77       | 10.88      |
| N (%) | 3.65        | 3.48       |

Examples 2–37 are shown in the following in which:
Dehydration assistant:
A. p-Toluenesulfonic acid.
B. p-Toluenesulfonic acid chloride.
C. Sulfuric acid.
D. Phenolsulfonic acid.
E. IRA-400
F. Amberlist-15
Solvent:
a. Toluene
b. Pyridine
c. Benzene
d. Chloroform
e. Xylene
f. Tetrachlorocarbon

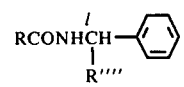

| Example No. | Fatty acid | —R'''' | Dehydration assistant | Solvent | Reaction time (hr) | b.p. °C./mmHg | C % Theoretical | C % Analytical | H % Theoretical | H % Analytical | N % Theoretical | N % Analytical |
|---|---|---|---|---|---|---|---|---|---|---|---|---|
| 2 | Oleic acid | $CH_3$ | A | a | 8 | 203–214/0.05 | 80.98 | 81.22 | 11.24 | 11.46 | 3.63 | 3.44 |
| 3 | Oleic acid | $CH_3$ | B | b | 20 | 204–218/0.07 | 80.98 | 81.10 | 11.24 | 11.42 | 3.63 | 3.43 |
| 4 | Linoleic acid | $CH_3$ | A | d | 10 | 200–217/0.05 | 81.40 | 81.65 | 10.77 | 10.90 | 3.65 | 3.41 |
| 5 | Linoleic acid | $CH_3$ | D | e | 10 | 202–218/0.05 | 81.40 | 81.65 | 10.77 | 10.90 | 3.65 | 3.42 |
| 6 | Linolenic acid | $CH_3$ | A | a | 10 | 204–213/0.05 | 81.83 | 82.00 | 10.30 | 10.62 | 3.67 | 6.32 |
| 7 | Linolenic acid | $CH_3$ | E | e | 10 | 206–214/0.05 | 81.83 | 82.13 | 10.30 | 10.54 | 3.67 | 6.45 |
| 8 | Isostearic acid | $CH_3$ | A | f | 12 | 206–217/0.04 | 80.56 | 80.70 | 11.70 | 11.75 | 3.61 | 3.58 |
| 9 | Isostearic acid | $CH_3$ | B | b | 20 | 202–218/0.06 | 80.56 | 80.70 | 11.70 | 11.97 | 3.61 | 3.46 |
| 10 | Safflower oil | $C_2H_5$ | F | e | 8 | 205–217/0.05 | | | | | | |
| 11 | Soybean oil | $CH_3$ | A | e | 8 | 204–216/0.05 | | | | | | |
| 12 | Sesame oil | $CH_3$ | A | e | 8 | 200–218/0.06 | | | | | | |
| 13 | Castor oil | $CH_3$ | A | d | 8 | 196–216/0.05 | | | | | | |
| 14 | Corn oil | $C_2H_5$ | B | b | 20 | 186–218/0.05 | | | | | | |
| 15 | Cottonseed oil | $CH_3$ | A | f | 8 | 189–208/0.06 | | | | | | |
| 16 | Olive oil | $CH_3$ | D | a | 8 | 183–207/0.05 | | | | | | |
| 17 | Linseed oil | $CH_3$ | C | a | 10 | 187–212/0.05 | | | | | | |
| 18 | Rape seed oil | $CH_3$ | A | a | 12 | 193–214/0.06 | | | | | | |
| 19 | Rice bran oil | $CH_3$ | A | a | 8 | 193–218/0.05 | | | | | | |
| 20 | Chrysalis oil | $CH_3$ | C | a | 8 | 188–212/0.05 | | | | | | |
| 21 | Sunflower oil | $CH_3$ | A | e | 8 | 191–215/0.06 | | | | | | |
| 22 | Flatfish oil | $CH_3$ | D | e | 8 | 196–220/0.05 | | | | | | |
| 23 | Shark oil | $CH_3$ | A | a | 10 | 186–209/0.06 | | | | | | |
| 24 | Whale oil | $CH_3$ | E | a | 10 | 184–220/0.05 | | | | | | |

-continued $$RCONHCH-\!\!\!\bigcirc \atop R''''$$

| Example No. | Fatty acid | —R'''' | Dehydration assistant | Solvent | Reaction time (hr) | b.p. °C./mmHg | C % Theoretical | C % Analytical | H % Theoretical | H % Analytical | N % Theoretical | N % Analytical |
|---|---|---|---|---|---|---|---|---|---|---|---|---|
| 25 | Cuttlefish oil | CH₃ | A | a | 8 | 198–219/0.06 | | | | | | |
| 26 | Sardine oil | CH₃ | B | b | 20 | 201–218/0.06 | | | | | | |
| 27 | Mackerel oil | CH₃ | F | a | 8 | 200–217/0.05 | | | | | | |
| 28 | Saury pike oil | C₂H₅ | A | c | 8 | 187–216/0.06 | | | | | | |
| 29 | Herring oil | CH₃ | C | d | 10 | 186–215/0.05 | | | | | | |
| 30 | Saurel oil | CH₃ | A | a | 10 | 184–213/0.05 | | | | | | |
| 31 | Manhaden oil | CH₃ | A | a | 10 | 182–222/0.08 | | | | | | |
| 32 | Cod oil | CH₃ | A | e | 8 | 192–218/0.05 | | | | | | |
| 33 | Liver oil | CH₃ | D | f | 12 | 182–217/0.06 | | | | | | |
| 34 | Residual oil | CH₃ | A | a | 8 | 184–223/0.08 | | | | | | |
| 35 | Manuke oil | CH₃ | A | e | 8 | 176–226/0.08 | | | | | | |
| 36 | Safflower oil | C₃H₇ | A | e | 10 | 199–204/0.02 | | | | | | |
| 37 | Safflower oil | C₄H₉ | A | e | 10 | 197–209/0.03 | | | | | | |

EXAMPLE 38

Linoleic acid (10 g.), 5 g. of (−)α-methylbenzylamine and 10 g. of dicyclohexyl carbodiimide were individually dissolved in 50 ml. of toluene. The solutions were mixed together at one portion, and the mixed solution was allowed to stand at room temperature for 8 hours.

After filtering the solution, the filtrate was with acid, alkali and water, and was then dried, concentrated and distilled to obtain 11.1 g. of a desired product, b.p. 201°–209° C./0.04 mmHg. Elementary analysis:

| | Theoretical | Analytical |
|---|---|---|
| C (%) | 81.40 | 81.51 |
| H (%) | 10.77 | 10.88 |
| N (%) | 3.65 | 3.51 |

Examples 39–74 are shown in the table below.

| Example No. | Acid | Amine R'''' | BN=C=NB B | Solvent | b.p. °C./mmHg | C % Theoretical | C % Analytical | H % Theoretical | H % Analytical | N % Theoretical | N % Analytical |
|---|---|---|---|---|---|---|---|---|---|---|---|
| 39 | Linoleic acid | CH₃ | —⟨⟩ | Ether | 200–208/0.04 | 81.40 | 81.77 | 10.77 | 10.73 | 3.65 | 3.45 |
| 40 | Linoleic acid | CH₃ | —⟨⟩ | Dioxane | 204–208/0.04 | 81.40 | 81.65 | 10.79 | 10.91 | 3.65 | 3.38 |
| 41 | Oleic acid | CH₃ | CH₃\CH—/CH₃ | Dioxane | 203–219/0.06 | 80.98 | 81.03 | 11.24 | 11.34 | 3.63 | 3.49 |
| 42 | Linolenic acid | CH₃ | —⟨⟩ | Tetrahydrofuran | 205–217/0.05 | 81.83 | 82.06 | 10.30 | 10.55 | 3.67 | 3.47 |
| 43 | Isostearic acid | CH₃ | —⟨⟩ | Ether | 208–218/0.07 | 80.56 | 80.71 | 11.70 | 11.86 | 3.61 | 3.54 |
| 44 | Isostearic acid | CH₃ | —⟨⟩ | Toluene | 200–214/0.05 | 80.56 | 80.98 | 11.70 | 11.87 | 3.61 | 3.48 |
| 45 | Safflower oil fatty acid | C₂H₅ | —⟨⟩ | Toluene | 201–214/0.05 | | | | | | |
| 46 | Soybean oil fatty acid | CH₃ | —⟨⟩ | Chloroform | 195–218/0.05 | | | | | | |
| 47 | Sesame oil fatty acid | CH₃ | —⟨⟩ | Toluene | 189–218/0.07 | | | | | | |
| 48 | Castor oil fatty acid | CH₃ | —⟨⟩ | Tetrachlorocarbon | 193–213/0.07 | | | | | | |

-continued

| Example No. | Acid | Amine R'''' | BN=C=NB B | Solvent | b.p. °C./mmHg | C % Theoretical | C % Analytical | H % Theoretical | H % Analytical | N % Theoretical | N % Analytical |
|---|---|---|---|---|---|---|---|---|---|---|---|
| 49 | Rape-seed oil | CH₃ |  | Benzene | 194–211/0.06 | | | | | | |
| 50 | Olive oil fatty acid | C₂H₅ |  | Pyridine | 196–215/0.06 | | | | | | |
| 51 | Rice bran oil fatty acid | CH₃ |  | Benzene | 185–214/0.06 | | | | | | |
| 52 | Cottonseed oil fatty acid | CH₃ |  | Toluene | 198–218/0.05 | | | | | | |
| 53 | Corn oil fatty acid | CH₃ |  | Toluene | 199–218/0.05 | | | | | | |
| 54 | Peanut oil fatty acid | CH₃ |  | Ether | 195–218/0.06 | | | | | | |
| 55 | Olive oil fatty acid | CH₃ |  | Toluene | 191–219/0.06 | | | | | | |
| 56 | Chrysalis oil fatty acid | CH₃ |  | Toluene | 196–215/0.05 | | | | | | |
| 57 | Shark oil fatty acid | CH₃ |  | Benzene | 205–222/0.05 | | | | | | |
| 58 | Cuttlefish oil fatty acid | CH₃ |  | Toluene | 181–228/0.05 | | | | | | |
| 59 | Sardine oil fatty acid | CH₃ |  | Ether | 192–226/0.07 | | | | | | |
| 60 | Mackerel oil fatty acid | CH₃ |  | Ether | 194–216/0.05 | | | | | | |
| 61 | Saury pike oil fatty acid | CH₃ |  | Benzene | 190–217/0.06 | | | | | | |
| 62 | Herring oil fatty acid | CH₃ |  | Ether | 192–218/0.05 | | | | | | |
| 63 | Saurel oil fatty acid | CH₃ |  | Toluene | 182–218/0.05 | | | | | | |
| 64 | Cod oil fatty acid | CH₃ |  | Chloroform | 186–216/0.05 | | | | | | |
| 65 | Trout oil fatty acid | CH₃ |  | Tetrahydrofuran | 180–219/0.05 | | | | | | |
| 66 | Gray mullet oil fatty acid | CH₃ |  | Tetrahydrofuran | 194–225/0.05 | | | | | | |
| 67 | Menuke oil fatty acid | CH₃ |  | Toluene | 189–215/0.06 | | | | | | |
| 68 | Menhaden oil fatty acid | C₂H₅ |  | Dioxane | 193–226/0.05 | | | | | | |
| 69 | Eel oil fatty acid | CH₃ |  | Benzene | 196–229/0.05 | | | | | | |

-continued

| Example No. | Acid | Amine BN=C=NB R'''' / B | Solvent | b.p. °C./mmHg | C % Theoretical | C % Analytical | H % Theoretical | H % Analytical | N % Theoretical | N % Analytical |
|---|---|---|---|---|---|---|---|---|---|---|
| 70 | Flatfish oil fatty acid | $CH_3$ / cyclohexyl | Dioxane | 189–220/0.05 | | | | | | |
| 71 | Whale oil fatty acid | $CH_3$ / cyclohexyl | Benzene | 175–223/0.06 | | | | | | |
| 72 | Liver oil fatty acid | $CH_3$ / cyclohexyl | Toluene | 190–218/0.07 | | | | | | |
| 73 | Residual oil fatty acid | $C_2H_5$ / cyclohexyl | Toluene | 194–228/0.08 | | | | | | |
| 74 | Safflower oil fatty acid | $C_3H_7$ / cyclohexyl | Dioxane | 199–209/0.06 | | | | | | |

EXAMPLE 75

A mixture of 10 g. of linoleic acid and 6 g. of l(−)α-methylbenzylamine, was heated at 180° C. for 24 hours removing water out of the reaction system. The reaction mixture was immediately subjected to distillation to obtain 11.3 g. of a desired product, b.p. 203°–221° C./0.07 mmHg. Elementary analysis:

| | Theoretical | Analytical |
|---|---|---|
| C (%) | 81.40 | 81.56 |
| H (%) | 10.77 | 10.86 |
| N (%) | 3.65 | 3.55 |

Examples 76–103 are shown in the table below.

$$RCONHCH\text{—}\bigcirc \quad / \quad R''''$$

| Example No. | Acid RCOOH | R'''' | Reaction temperature | Reaction time (hr) | b.p. °C./mmHg | C % Theoretical | C % Analytical | H % Theoretical | H % Analytical | N % Theoretical | N % Analytical |
|---|---|---|---|---|---|---|---|---|---|---|---|
| 76 | Isostearic acid | o | 180 | 24 | 206–218/0.06 | 80.56 | 80.67 | 11.70 | 11.98 | 3.61 | 3.38 |
| 77 | Oleic acid | o | 180 | 24 | 206–217/0.05 | 80.98 | 81.28 | 11.24 | 11.53 | 3.63 | 3.39 |
| 78 | Linolenic acid | o | 180 | 24 | 209–216/0.06 | 81.83 | 81.95 | 10.30 | 10.54 | 3.67 | 3.38 |
| 79 | Safflower oil acid | o | 180 | 24 | 194–219/0.07 | | | | | | |
| 80 | Soybean oil acid | o | 200 | 20 | 197–221/0.05 | | | | | | |
| 81 | Corn oil acid | o | 180 | 20 | 193–208/0.06 | | | | | | |
| 82 | Cottonseed oil acid | x | 180 | 24 | 197–215/0.05 | | | | | | |
| 83 | Sesame oil acid | o | 160 | 36 | 198–206/0.04 | | | | | | |
| 84 | Castor oil acid | o | 160 | 36 | 200–222/0.04 | | | | | | |
| 85 | Olive oil acid | o | 180 | 24 | 188–211/0.06 | | | | | | |
| 86 | Rape-seed oil acid | o | 180 | 24 | 206–216/0.05 | | | | | | |
| 87 | Sunflower oil acid | o | 180 | 24 | 198–214/0.06 | | | | | | |
| 88 | Linseed oil acid | o | 180 | 24 | 188–215/0.05 | | | | | | |
| 89 | Rice bran oil acid | o | 180 | 24 | 181–213/0.07 | | | | | | |
| 90 | Shark oil acid | x | 180 | 24 | 185–221/0.05 | | | | | | |
| 91 | Whale oil acid | o | 180 | 26 | 175–225/0.04 | | | | | | |
| 92 | Mackerel oil acid | o | 180 | 24 | 193–208/0.06 | | | | | | |
| 93 | Saurel oil acid | o | 180 | 24 | 189–215/0.07 | | | | | | |
| 94 | Cuttlefish oil acid | o | 200* | 18 | 186–214/0.06 | | | | | | |
| 95 | Cod oil acid | o | 200* | 18 | 188–222/0.08 | | | | | | |
| 96 | Herring oil acid | o | 210* | 18 | 193–215/0.04 | | | | | | |
| 97 | Sardine oil acid | o | 180 | 20 | 196–220/0.08 | | | | | | |
| 98 | Flatfish oil acid | o | 180 | 24 | 194–221/0.05 | | | | | | |
| 99 | Menhaden oil acid | o | 180 | 24 | 190–218/0.06 | | | | | | |
| 100 | Liver oil acid | o | 180 | 20 | 195–220/0.05 | | | | | | |
| 101 | Residual oil acid | o | 180 | 20 | 186–215/0.05 | | | | | | |
| 102 | Safflower oil acid | + | 180 | 20 | 202–210/0.04 | | | | | | |
| 103 | Safflower oil | § | 180 | 20 | 205–211/0.05 | | | | | | |

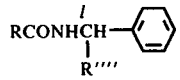

| Example No. | Acid RCOOH | R'''' | Reaction temperature | Reaction time (hr) | b.p. °C./mmHg | C % Theoretical | C % Analytical | H % Theoretical | H % Analytical | N % Theoretical | N % Analytical |
|---|---|---|---|---|---|---|---|---|---|---|---|
| | acid | | | | | | | | | | |

* In an autoclave
o = CH₃
x = C₂H₅
+ = C₃H₇
§ = C₄H₉

EXAMPLE 104

A mixture of 10 g. of methyl linoleate and 6 g. of (−)α-methylbenzylamine was heated in a nitrogen atmosphere at 180° C. for 30 hours removing methanol out of the reaction system. The reaction mixture was distilled to obtain 12.3 g. of a desired product, b.p. 200°−216° C./0.05 mmHg, [α] D₂₅ −59.5. Elementary analysis:

| | Theoretical | Analytical |
|---|---|---|
| C (%) | 81.40 | 81.60 |
| H (%) | 10.77 | 10.81 |
| N (%) | 3.65 | 3.48 |

EXAMPLE 105

A mixture of 10 g. of methyl isostearate, 5 g. of (−)α-methylbenzylamine and 1 g. of sodium methylate was heated at 150° C. for 3 hours, while excluding out of the reaction system methanol by-produced in this case. Subsequently, the reaction mixture was washed with acid, alkali and water according to ordinary procedures, and was then dried and concentrated to obtain 12.3 g. of a desired product, b.p. 205°−226° C./0.06 mmHg. Elementary analysis:

| | Theoretical | Analytical |
|---|---|---|
| C (%) | 80.56 | 80.50 |
| H (%) | 11.70 | 11.78 |
| N (%) | 3.61 | 3.74 |

EXAMPLE 106

To a mixture comprising 10 g. of ethyl oleate and 5 g. of (−)α-methylbenzylamine was added a solution of 0.5 g. of sodium in 8 ml. of ethyl alcohol. The mixture was reacted at 160° C. for about 2 hours removing ethyl alcohol during reaction. Thereafter, the same treatments as in Example 2 were effected to obtain 12.0 g. of a desired product, b.p. 208°−218° C./0.06 mmHg. Elementary analysis:

| | Theoretical | Analytical |
|---|---|---|
| C (%) | 80.98 | 80.89 |
| H (%) | 11.24 | 11.18 |
| N (%) | 3.63 | 3.80 |

EXAMPLE 107

A mixture of 10 g. of safflower oil and 6 g. of (−)α-methylbenzylamine was heated in an autoclave at 200° C. for 12 hours and was then immediately distilled to obtain 13.0 g. of a desired product, b.p. 197°−226° C./0.05 mmHg.

Examples 108−139 are shown in the following table:

| Example No. | Ester or glyceride | R'''' | Reference example | Reaction temperature | Reaction time (h) | Catalyst | Solvent | b.p. °C./mmHg |
|---|---|---|---|---|---|---|---|---|
| 108 | Methyl linoleate | o | 4 | 200 | 12 | | | 200−214/0.04 |
| 109 | Ethyl linoleate | o | 1 | 180 | 48 | | | 203−209/0.05 |
| 110 | Methyl oleate | o | 2 | 160 | 4 | KOtBu | | 204−227/0.06 |
| 111 | Methyl isostearate | o | 3 | 160 | 2 | NaOCH₃, | CH₃OH | 206−218/0.07 |
| 112 | Methyl linolenate | o | 4 | 200 | 14 | | | 206−218/0.05 |
| 113 | Safflower oil methyl ester | o | 4 | 200 | 14 | | | 198−209/0.05 |
| 114 | Sesame oil methyl esters | o | 4 | 200 | 12 | | | 198−213/0.05 |
| 115 | Castor oil methyl ester | o | 1 | 180 | 42 | | | 199−218/0.05 |
| 116 | Rape-seed oil methyl ester | * | 1 | 180 | 40 | | | 188−209/0.05 |
| 117 | Olive oil methyl ester | o | 2 | 150 | 3 | NaOCH₃ | | 188−209/0.05 |
| 118 | Rica bran oil | o | 4 | 180 | 10 | | | 189−214/0.15 |

-continued

| Example No. | Ester or glyceride | R'''' | Reference example | Reaction temperature | Reaction time (h) | Catalyst | Solvent | b.p. °C./mmHg |
|---|---|---|---|---|---|---|---|---|
| | methyl ester | | | | | | | |
| 119 | Cottonseed oil methyl ester | * | 1 | 180 | 38 | | | 195–203/0.05 |
| 120 | Chrysalis oil methyl ester | o | 1 | 180 | 38 | | | 193–216/0.06 |
| 121 | Sardine oil methyl ester | o | 1 | 180 | 42 | | | 187–218/0.05 |
| 122 | Fish oil methyl ester | o | 1 | 180 | 42 | | | 187–212/0.05 |
| 123 | Flatfish oil methyl ester | o | 1 | 180 | 38 | | | 197–224/0.05 |
| 124 | Safflower oil | * | 4 | 190 | 20 | | | 199–215/0.05 |
| 125 | Linseed oil | o | 4 | 190 | 18 | | | 187–214/0.06 |
| 126 | Soybean oil | o | 4 | 190 | 18 | | | 195–218/0.06 |
| 127 | Sunflower oil | o | 4 | 200 | 12 | | | 196–212/0.06 |
| 128 | Corn oil | o | 4 | 200 | 12 | | | 195–218/0.07 |
| 129 | Shark oil | o | 4 | 190 | 12 | | | 184–215/0.07 |
| 130 | Cuttlefish oil | o | 4 | 180 | 16 | | | 190–216/0.07 |
| 131 | Sardine oil | o | 4 | 190 | 14 | | | 194–218/0.07 |
| 132 | Mackerel oil | o | 4 | 190 | 15 | | | 193–200/0.06 |
| 133 | Saury pike oil | o | 4 | 200 | 12 | | | 194–218/0.06 |
| 134 | Herring oil | o | 4 | 200 | 12 | | | 196–218/0.04 |
| 135 | Saurel oil | o | 4 | 200 | 12 | | | 189–214/0.06 |
| 136 | Flatfish oil | o | 4 | 190 | 12 | | | 195–217/0.05 |
| 137 | Menhaden oil | o | 4 | 190 | 14 | | | 193–214/0.04 |
| 138 | Liver oil | o | 4 | 190 | 12 | | | 193–226/0.06 |
| 139 | Residual oil | o | 4 | 190 | 16 | | | 188–217/0.07 |

| Example No. | Ester or glyceride | Theoretical | Analytical | Theoretical | Analytical | Theoretical | Analytical |
|---|---|---|---|---|---|---|---|
| 108 | Methyl linoleate | 81.40 | 81.58 | 10.77 | 10.93 | 3.65 | 3.44 |
| 109 | Ethyl linoleate | 81.40 | 81.56 | 10.77 | 10.80 | 3.65 | 3.38 |
| 110 | Methyl oleate | 80.98 | 81.21 | 11.24 | 1.42 | 3.63 | 3.44 |
| 111 | Methyl isostearate | 80.50 | 80.78 | 11.70 | 11.99 | 3.61 | 3.46 |
| 112 | Methyl linolenate | 81.83 | 81.89 | 10.30 | 10.56 | 3.67 | 3.39 | o R'''' = CH$_3$
*R'''' = C$_2$H$_5$

EXAMPLE 140

Linoleic acid chloride (30 g.) was dissolved in 50 ml. of anhydrous ether. The solution was added dropwise with cooling and stirring at 0°–5° C. to a mixture of 12.5 g. of l(−)α-methylbenzylamine, 100 ml. of anhydrous ether and 8 g. of trimethylamine. After completion of the dropwise addition, the reaction mixture was boiled for 2 hours to complete the reaction. The ether solution of the reaction product was washed with acid, alkali and water and was then dried, concentrated and distilled to obtain 42 g. of a desired product, b.p. 209°–218° C./0.05 mmHg. Elementary analysis:

| | Theoretical | Analytical |
|---|---|---|
| C (%) | 81.46 | 81.38 |
| H (%) | 10.77 | 10.81 |
| N (%) | 3.45 | 3.61 |

Examples 141–175 are shown in the following table:

| Ex. No. | Acid halide Acid | x | | Solvent | Condensation assistant | b.p. °C./mmHg | C % Theoretical | C % Analytical | H % Theoretical | H % Analytical | N % Theoretical | N % Analytical |
|---|---|---|---|---|---|---|---|---|---|---|---|---|
| 141 | Oleic acid | Cl | o | Acetone | K$_2$CO$_3$ | 208–217/0.05 | 80.98 | 81.14 | 11.24 | 11.40 | 3.63 | 3.94 |
| 142 | Oleic acid | Cl | o | Tetrahydrofuran-water | NaOH | 207–217/0.05 | 80.98 | 81.08 | 11.24 | 11.30 | 3.63 | 3.65 |
| 143 | Isostearic acid | Cl | o | Ether | Trimethylamine | 206–219/0.06 | 80.56 | 80.74 | 11.70 | 11.92 | 3.61 | 3.40 |
| 144 | Isostearic acid | Cl | o | Toluene | Pyridine | 203–217/0.05 | 80.56 | 80.71 | 11.70 | 11.85 | 3.61 | 3.40 |
| 145 | Linoletic acid | Cl | o | Acetone | Picoline | 206–213/0.05 | 81.40 | 81.64 | 10.77 | 10.83 | 3.65 | 3.69 |
| 146 | Linoleic acid | Cl | o | Methylbutylketone | Triethylamine | 203–216/0.06 | 81.40 | 81.73 | 10.77 | 10.92 | 3.65 | 3.37 |
| 147 | Linolenic acid | Cl | o | Ether | Triethylamine | 202–218/0.05 | 81.83 | 81.92 | 10.30 | 10.54 | 3.67 | 3.44 |
| 148 | Linolenic acid | Cl | o | Benzene | Dimethylaniline | 204–216/0.04 | 81.83 | 81.96 | 10.30 | 10.65 | 3.67 | 3.45 |
| 149 | Safflower oil acid | Cl | * | Dioxane-water | KOH | 197–208/0.05 | | | | | | |
| 150 | Safflower oil acid | Cl | o | Dioxane-water | KOH | 198–211/0.05 | | | | | | |
| 151 | Soybean oil acid | Cl | o | Acetone-water | K$_2$CO$_3$ | 196–210/0.06 | | | | | | |
| 152 | Sesame oil acid | Cl | o | Ether | Pyridine | 198–214/0.06 | | | | | | |
| 153 | Castor oil acid | Cl | o | Ether | Pyridine | 193–218/0.04 | | | | | | |

-continued

| Ex. No. | Acid halide Acid | x | Solvent | Condensation assistant | b.p. °C./mmHg |
|---|---|---|---|---|---|
| 154 | Rape-seed oil acid | Cl o | Ether | Pyridine | 201–227/0.06 |
| 155 | Olive oil acid | Cl * | Toluene | Trimethylamine | 186–213/0.05 |
| 156 | Rica bran oil acid | Cl o | toluene | Triethylamine | 186–215/0.06 |
| 157 | Cottonseed oil acid | Cl o | Benzene | Pyridine | 194–213/0.05 |
| 158 | Chrysalis oil acid | Cl o | Toluene | Pyridine | 190–212/0.06 |
| 159 | Corn oil acid | Cl o | Acetone-water | NaOH | 208–221/0.08 |
| 160 | Linseed oil acid | Cl o | Ether | Pyridine | 190–211/0.06 |
| 161 | Sunflower oil acid | Cl o | Tetrahydrofuran-water | NaOH | 195–212/0.05 |
| 162 | Flatfish oil acid | Cl o | Methylbutylketone | $K_2CO_3$ | 189–215/0.04 |
| 163 | Shark oil acid | Cl * | Acetone-water | NaOH | 185–218/0.04 |
| 164 | Whale oil acid | Cl o | Acetone-water | $Na_2CO_3$ | 184–209/0.05 |
| 165 | Cuttlefish oil acid | Cl o | Dioxane-water | NaOH | 186–217/0.05 |
| 166 | Sardine oil acid | Cl * | Dioxane-water | $K_2CO_3$ | 198–218/0.05 |
| 167 | Mackerel oil acid | Cl o | Toluene | Pyridine | 195–211/0.05 |
| 168 | Saury pike oil acid | Cl o | Dioxane-water | NaOH | 199–210/0.05 |
| 169 | Herring oil acid | Cl o | Toluene | Pyridine | 193–217/0.05 |
| 170 | Saurel oil acid | Cl o | Acetone-water | NaOH | 183–214/0.05 |
| 171 | Menhaden oil acid | Cl o | Toluene | Pyridine | 195–225/0.05 |
| 172 | Cod-oil acid | Cl o | Acetone-water | KOH | 184–208/0.05 |
| 173 | Liver oil acid | Cl * | Ether | Pyridine | 196–215/0.04 |
| 174 | Residual oil acid | Cl o | Acetone-water | KOH | 188–218/0.06 |
| 175 | Menuke oil acid | Cl o | Acetone-water | NaOH | 189–205/0.06 |

EXAMPLE 176

A mixture of 100 g. of safflower oil, 43 g. of d(+)α-methyl-benzylamine and 2 g. of boric acid was heated at 140° C. for 7 hours. Subsequently, the reaction product was dissolved in ether. The resulting solution was washed with 5% hydrochloric acid water, 5% caustic soda water and water, and was dried, concentrated and distilled to obtain 121 g. of a desired product, b.p. 202°–209° C./0.04 mmHg.

Examples 177–223 are shown in the following tables:

$$RCONHCH-\underset{R''''}{\bigcirc}$$

| Example No. | Glyceride | Amine R'''' | | Reaction time (hr) | Reaction temperature °C. | b.p. °C./mmHg | Boric acid |
|---|---|---|---|---|---|---|---|
| 177 | Linseed oil | d (+) | $CH_3$ | 4 | 140° | 201–222/0.05 | 5 |
| 178 | Soybean oil | l (−) | $CH_3$ | 4 | " | 200–218/0.06 | 5 |
| 179 | Sunflower oil | d (+) | $C_2H_5$ | 4 | " | 198–219/0.06 | 3 |
| 180 | Rice bran oil | d (+) | $C_2H_5$ | 6 | " | 201–223/0.04 | 1 |
| 181 | Corn oil | d (+) | $C_3H_7$ | 6 | " | 200–219/0.05 | 1 |
| 182 | Sesame oil | l (−) | $C_3H_7$ | 5 | " | 189–213/0.03 | 2 |
| 183 | Cottonseed oil | l (−) | $C_4H_9$ | 6 | 150 | 203–230/0.07 | 1 |
| 184 | Castor oil | d (+) | $C_4H_9$ | 6 | 140 | 205–218/0.06 | 1 |
| 185 | Shark oil | l (−) | $CH_3$ | 4 | " | 193–223/0.05 | 3 |
| 186 | Cuttlefish oil | d (+) | $CH_3$ | 6 | " | 190–222/0.05 | 1 |
| 187 | Sardine oil | l (−) | $C_2H_5$ | 6 | " | 198–224/0.05 | 1 |
| 188 | Mackerel oil | l (−) | $C_2H_5$ | 8 | " | 200–218/0.06 | 0.5 |
| 189 | Saury pike oil | d (+) | $CH_3$ | 5 | " | 202–218/0.06 | 1 |
| 190 | Herring oil | l (−) | $CH_3$ | 8 | " | 188–219/0.05 | 1 |
| 191 | Saurel oil | d (+) | $CH_3$ | 5 | 160 | 199–228/0.04 | 2 |
| 192 | Cod oil | l (−) | $C_3H_7$ | 4 | 160 | 206–232/0.02 | 2 |
| 193 | Flatfish oil | d (+) | $C_4H_9$ | 6 | " | 200–223/0.05 | 2 |
| 194 | Whale oil | d (+) | $CH_3$ | 7 | " | 200–218/0.05 | 1 |

| | Acid or Ester | | | | | | |
|---|---|---|---|---|---|---|---|
| 195 | Linseed oil | H | d (+) | $CH_3$ | 5 | 145° | 201–222/0.05 | 3 |
| 196 | Soybean oil | H | l (−) | $CH_3$ | 5 | 145° | 200–219/0.05 | 3 |
| 197 | Sunflower oil | H | d (+) | $CH_3$ | 5 | 145° | 196–221/0.05 | 3 |

-continued

| | | | | | | | | |
|---|---|---|---|---|---|---|---|---|
| 198 | Rice bran oil | CH₃ | d (+) | CH₃ | 5 | 145° | 203–225/0.05 | 3 |
| 199 | Corn oil | CH₃ | d (+) | C₂H₅ | 5 | 145° | 200–220/0.06 | 3 |
| 200 | Sesame oil | H | l (−) | CH₃ | 5 | 145° | 188–215/0.03 | 3 |
| 201 | Cottonseed oil | CH₃ | l (−) | C₂H₅ | 5 | 145° | 205–230/0.05 | 3 |
| 202 | Castor oil | CH₃ | l (−) | CH₃ | 6 | 145° | 208–219/0.04 | 3 |
| 203 | Shark oil | H | d (+) | C₂H₅ | 5 | 145° | 198–225/0.05 | 3 |
| 204 | Cuttlefish oil | CH₃ | d (+) | C₃H₇ | 7 | 145° | 188–224/0.05 | 2 |
| 205 | Sardine oil | C₂H₅ | d (+) | C₃H₇ | 7 | 145° | 198–225/0.05 | 1 |
| 206 | Mackerel oil | H | d (+) | CH₃ | 5 | 145° | 200–218/0.06 | 3 |
| 207 | Saury pike oil | C₃H₇ | l (−) | C₄H₉ | 7 | 145° | 200–220/0.07 | 3 |
| 208 | Herring oil | H | d (+) | C₄H₉ | 8 | 145° | 189–219/0.05 | 1 |
| 209 | Saurel oil | CH₃ | l (−) | CH₃ | 8 | 145° | 198–230/0.03 | 1 |
| 210 | Cod oil | H | l (−) | C₃H₇ | 8 | 145° | 208–230/0.02 | 1 |
| 211 | Flatfish oil | H | l (−) | C₄H₉ | 5 | 145° | 200–225/0.04 | 3 |
| 212 | Whale oil | H | d (+) | CH₃ | 7 | 145° | 200–219/0.05 | 3 |

| Example No. | RCOOA R | A | R'''' | Reaction time (hr) | Reaction temperature | Boric acid | b.p. °C./mmHg | C % Theoretical | C % Analytical | H % Theoretical | H % Analytical | N % Theoretical | N % Analytical |
|---|---|---|---|---|---|---|---|---|---|---|---|---|---|
| 213 | C₁₇H₂₉ | H | d (+) CH₃ | 5 | 150 | 2 | 203–223/0.05 | 81.83 | 81.67 | 10.30 | 10.17 | 3.67 | 3.66 |
| 214 | C₁₇H₂₉ | CH₃ | l (−) CH₃ | 5 | 145 | 2 | 203–225/0.04 | 81.83 | 81.78 | 10.30 | 10.17 | 3.67 | 3.69 |
| 215 | C₁₇H₃₁ | H | l (−) CH₃ | 5 | 140 | 2 | 200–219/0.05 | 81.19 | 81.19 | 10.77 | 10.69 | 3.65 | 3.87 |
| 216 | C₁₇H₃₁ | CH₃ | d (+) C₂H₅ | 8 | 145 | 1 | 204–221/0.05 | 81.55 | 81.49 | 10.90 | 10.81 | 3.52 | 3.42 |
| 217 | C₁₇H₃₁ | C₂H₅ | d (+) C₂H₅ | 6 | 145 | 1 | 200–219/0.05 | 81.55 | 81.38 | 10.90 | 10.80 | 3.52 | 3.65 |
| 218 | Iso-C₁₇H₃₅ | H | d (+) CH₃ | 4 | 145 | 3 | 200–200/0.06 | 80.56 | 80.33 | 11.70 | 11.54 | 3.61 | 3.65 |
| 219 | Iso-C₁₇H₃₅ | H | l (−) CH₃ | 5 | 145 | 3 | 206–216/0.05 | 80.56 | 80.42 | 11.70 | 11.43 | 3.61 | 3.71 |
| 220 | Iso-C₁₇H₃₅ | H | l (−) C₂H₅ | 8 | 140 | 2 | 205–219/0.05 | 80.73 | 80.69 | 11.80 | 11.79 | 3.49 | 3.39 |
| 221 | C₁₇H₃₁ | H | d (+) CH₃ | 8 | 140 | 2 | 200–209/0.05 | 81.40 | 81.31 | 10.77 | 10.65 | 3.65 | 3.49 |
| 222 | C₁₇H₃₁ | CH₃ | d (+) C₃H₇ | 5 | 145 | 4 | 200–208/0.05 | 81.69 | 81.49 | 11.02 | 11.00 | 3.40 | 3.51 |
| 223 | C₁₇H₃₃ | H | l (−) CH₃ | 4 | 145 | 3 | 201–205/0.01 | 80.98 | 80.88 | 11.24 | 11.21 | 3.63 | 3.62 |

EXAMPLE 224

A mixture of 10 g. of linoleic acid and 5 g. of (+)α-methylbenzylamine was heated for about 8 hours in 300 ml. of toluene in the presence of 0.2 g. of p-toluenesulfonic acid, using a water separator.

After completion of the reaction, the toluene layer was washed with aqueous solution of acid, alkali and with water and dried and concentrated to obtain 12.1 g. of a desired product, b.p. 200°–211° C./0.05 mmHg. Elementary analysis:

| | Theoretical | Analytical |
|---|---|---|
| C (%) | 81.40 | 81.71 |
| H (%) | 10.77 | 10.93 |
| N (%) | 3.65 | 3.38 |

Examples 225–259 are shown in the following table, in which:

Dehydration agent:
A. p-Toluenesulfonic acid
B. p-Toluenesulfonic acid chloride
C. Sulfuric acid
D. Phenolsulfonic acid
E. IRA-400
F. Amberlist-15

Solvent:
a. Toluene
b. Pyridine
c. Benzene
d. Chloroform
e. Xylene
f. Carbon tetrachloride

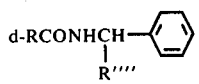

d-RCONHCH—⟨⟩
         |
         R''''

| Example No. | Fatty acid | R'''' | Dehydration assistant | Solvent | Reaction time (hr) | b.p. ° C./mmHg | C % Theoretical | C % Analytical | H % Theoretical | H % Analytical | N % Theoretical | N % Analytical |
|---|---|---|---|---|---|---|---|---|---|---|---|---|
| 225 | Oleic acid | CH₃ | A | a | 8 | 203–211/0.05 | 80.98 | 81.21 | 11.24 | 11.45 | 3.63 | 3.45 |
| 226 | Oleic acid | CH₃ | B | b | 20 | 205–216/0.07 | 80.98 | 81.19 | 11.24 | 11.41 | 3.63 | 3.49 |
| 227 | Linoleic acid | CH₃ | A | d | 10 | 200–211/0.05 | 81.40 | 81.63 | 10.77 | 10.93 | 3.65 | 3.41 |
| 228 | Linoleic acid | CH₃ | D | e | 10 | 201–210/0.05 | 81.40 | 81.66 | 10.77 | 10.97 | 3.65 | 3.43 |
| 229 | Linolenic acid | CH₃ | A | a | 10 | 201–213/0.05 | 81.83 | 82.09 | 10.30 | 10.61 | 3.67 | 6.32 |
| 230 | Linolenic acid | CH₃ | E | e | 10 | 200–212/0.05 | 81.83 | 82.12 | 10.30 | 10.59 | 3.67 | 6.41 |
| 231 | Isostearic acid | CH₃ | A | f | 12 | 206–218/0.04 | 80.56 | 80.78 | 11.70 | 11.76 | 3.61 | 3.58 |
| 232 | Isostearic acid | CH₃ | B | b | 20 | 201–219/0.06 | 80.56 | 80.79 | 11.70 | 11.98 | 3.61 | 3.40 |
| 233 | Safflower oil | C₂H₅ | F | e | 8 | 205–217/0.06 | | | | | | |
| 234 | Soybean oil | CH₃ | A | e | 8 | 201–210/0.05 | | | | | | |
| 235 | Sesame oil | CH₃ | A | e | 8 | 200–213/0.06 | | | | | | |
| 236 | Castor oil | CH₃ | A | d | 8 | 197–215/0.05 | | | | | | |
| 237 | Corn oil | C₂H₅ | B | b | 20 | 186–218/0.05 | | | | | | |
| 238 | Cottonseed oil | CH₃ | A | f | 8 | 189–209/0.06 | | | | | | |
| 239 | Olive oil | CH₃ | D | a | 8 | 183–208/0.05 | | | | | | |
| 240 | Linseed oil | CH₃ | C | a | 10 | 187–211/0.05 | | | | | | |

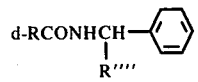

| Example No. | Fatty acid | R'''' | Dehydration assistant | Solvent | Reaction time (hr) | b.p. °C./mmHg |
|---|---|---|---|---|---|---|
| 241 | Rape-seed oil | CH₃ | A | a | 12 | 193–216/0.06 |
| 242 | Rice bran oil | CH₃ | A | a | 8 | 193–210/0.05 |
| 243 | Chrysalia oil | CH₃ | C | a | 8 | 188–214/0.06 |
| 244 | Sunflower oil | CH₃ | A | e | 8 | 191–213/0.06 |
| 245 | Flatfish oil | CH₃ | D | e | 8 | 190–220/0.05 |
| 246 | Shark oil | CH₃ | A | a | 10 | 187–209/0.06 |
| 247 | Whale oil | CH₃ | E | a | 10 | 187–220/0.05 |
| 248 | Cuttlefish oil | CH₃ | A | a | 8 | 193–218/0.06 |
| 249 | Sardine oil | CH₃ | B | b | 20 | 201–219/0.06 |
| 250 | Mackerel oil | CH₃ | F | a | 8 | 200–218/0.05 |
| 251 | Saury pike oil | C₂H₅ | A | c | 8 | 187–217/0.06 |
| 252 | Herring oil | CH₃ | C | d | 10 | 185–215/0.05 |
| 253 | Saurel oil | CH₃ | A | a | 10 | 184–212/0.05 |
| 254 | Manhaden oil | CH₃ | A | a | 10 | 182–222/0.08 |
| 255 | Cod oil | CH₃ | A | e | 8 | 190–218/0.05 |
| 256 | Liver oil | CH₃ | D | f | 12 | 189–217/0.06 |
| 257 | Residual oil | CH₃ | A | a | 8 | 184–221/0.08 |
| 258 | Menuke oil | CH₃ | A | e | 8 | 175–220/0.08 |
| 259 | Safflower oil | C₃H₇ | A | e | 12 | 199–211/0.04 |

EXAMPLE 260

A mixture of 10 g. of methyl linoleate and 6 g. of (+)α-methylbenzylamine was heated at 180° C. for 30 hours in a nitrogen atmosphere, while excluding by-produced methanol out of the reaction system. After completion of the reaction, the reaction mixture was distilled to obtain 12.3 g. of a desired product, b.p. 202°–215° C./0.05 mmHg, $[\alpha]^D_{25} +59.5$. Elementary analysis:

|  | Theoretical | Analytical |
|---|---|---|
| C (%) | 81.40 | 81.62 |
| H (%) | 10.77 | 10.85 |
| N (%) | 3.65 | 3.46 |

EXAMPLE 261

A mixture of 10 g. of methyl isostearate was mixed with 5 g. of (+)α-methylbenzylamine and 1 g. of sodium methylate. The mixture was reacted at 150° C. for 3 hours while excluding by-produced methanol out of the reaction system. The reaction mixture was washed with acid, alkali and water according to ordinary procedures and was dried and distilled to obtain 12.3 g. of a desired product, b.p. 207°–220° C./0.06 mmHg. Elementary analysis:

|  | Theoretical | Analytical |
|---|---|---|
| C (%) | 80.56 | 80.49 |
| H (%) | 11.70 | 11.77 |
| N (%) | 3.61 | 3.81 |

EXAMPLE 262

To a mixture of 10 g. of ethyl oleate and 5 g. of (+)α-methylbenzylamine was added a solution of 0.5 g. of sodium in 8 ml. of ethyl alcohol. The mixture was reacted at 160° C. for about 2 hours removing ethyl alcohol. Thereafter, the same treatments as in Example 261 were effected to obtain 12.0 g. of a desired product, b.p. 208°–219° C./0.06 mmHg. Elementary analysis:

|  | Theoretical | Analytical |
|---|---|---|
| C (%) | 80.98 | 80.88 |
| H (%) | 11.24 | 11.17 |
| N (%) | 3.63 | 3.81 |

EXAMPLE 263

A mixture of 10 g. of safflower oil and 6 g. of (+)α-methylbenzylamine was heated in an autoclave at 200° C. for 12 hours and was then immediately distilled to obtain 13.0 g. of a desired product, b.p. 197°–220° C./0.05 mmHg.

Examples 264–296 are shown in the following table:

RCONHCH—⌬ | R''''

| Example No. | Ester or glyceride | R'''' | Reference example | Reaction temperature | Reaction time (hr) | Catalyst | Solvent | b.p. °C./mmHg |
|---|---|---|---|---|---|---|---|---|
| 264 | Methyl linoleate | o | 263 | 200 | 12 |  |  | 200–211/0.04 |
| 265 | Ethyl linoleate | o | 260 | 180 | 48 |  |  | 201–209/0.05 |

-continued

| | | | | | | | |
|---|---|---|---|---|---|---|---|
| 266 | Methyl oleate | o | 261 | 160 | 4 | KOtBu | 204–221/0.06 |
| 267 | Methyl isostearate | o | 262 | 160 | 2 | NaOCH$_3$,CH$_3$OH | 206–219/0.07 |
| 268 | Methyl linolenate | o | 263 | 200 | 14 | | 205–218/0.05 |
| 269 | Safflower oil methyl ester | 0 | 263 | 200 | 14 | | 198–209/0.05 |
| 270 | Sesame oil methyl ester | o | 263 | 200 | 12 | | 198–211/0.05 |
| 271 | Castor oil methyl ester | o | 260 | 180 | 42 | | 199–215/0.05 |
| 272 | Rape-seed oil methyl ester | * | 260 | 180 | 40 | | 201–220/0.06 |
| 273 | Olive oil methyl ester | o | 261 | 150 | 3 | NaOCH$_3$ | 188–209/0.55 |
| 274 | Rice bran oil methyl ester | o | 263 | 190 | 10 | | 189–211/0.05 |
| 275 | Cottonseed oil methyl ester | * | 260 | 180 | 38 | | 193–208/0.05 |
| 276 | Chrysalis oil methyl ester | o | 260 | 180 | 38 | | 193–212/0.06 |
| 277 | Sardine oil methyl ester | o | 260 | 180 | 42 | | 187–215/0.05 |
| 278 | Fish oil methyl ester | o | 260 | 180 | 42 | | 187–208/0.05 |
| 279 | Flatfish oil methyl ester | o | 260 | 180 | 36 | | 197–223/0.05 |
| 280 | Safflower oil | * | 263 | 190 | 20 | | 199–210/0.05 |
| 281 | Linseed oil | o | 263 | 190 | 18 | | 187–216/0.06 |
| 282 | Soybean oil | o | 263 | 190 | 18 | | 196–217/0.06 |
| 283 | Sunflower oil | o | 263 | 200 | 12 | | 194–212/0.06 |
| 284 | Corn oil | o | 263 | 200 | 12 | | 195–213/0.07 |
| 285 | Shark oil | o | 263 | 190 | 12 | | 184–216/0.07 |
| 286 | Cuttlefish oil | o | 263 | 180 | 16 | | 189–217/0.07 |
| 287 | Sardine oil | o | 263 | 190 | 14 | | 191–213/0.07 |
| 288 | Mackerel oil | o | 263 | 190 | 15 | | 193–209/0.06 |
| 289 | Saury pike oil | o | 263 | 200 | 12 | | 194–213/0.06 |
| 290 | Herring oil | o | 263 | 200 | 12 | | 196–213/0.04 |
| 291 | Saurel oil | o | 263 | 200 | 12 | | 188–214/0.06 |
| 292 | Flatfish oil | o | 263 | 190 | 12 | | 196–217/0.05 |
| 293 | Menhaden oil | o | 263 | 190 | 14 | | 193–219/0.04 |
| 294 | Liver oil | o | 263 | 190 | 12 | | 193–220/0.06 |
| 295 | Residual oil | o | 263 | 190 | 16 | | 188–218/0.07 |
| 296 | Safflower oil (R''''=C$_3$H$_7$) | | 263 | 200 | 18 | | 200–209/0.02 |

| Example No. | Ester or glyceride | C% Theoretical | C% Analytical | H% Theoretical | H% Analytical | N% Theoretical | N% Analytical |
|---|---|---|---|---|---|---|---|
| 264 | Methyl linoleate | 81.40 | 81.59 | 10.77 | 10.91 | 3.65 | 3.44 |
| 265 | Ethyl linoleate | 81.40 | 81.58 | 10.77 | 10.88 | 3.65 | 3.33 |
| 266 | Methyl oleate | 80.98 | 81.20 | 11.24 | 11.44 | 3.63 | 3.42 |
| 267 | Methyl isostearate | 80.56 | 80.77 | 11.70 | 11.98 | 3.61 | 3.47 |
| 268 | Methyl linolenate | 81.83 | 81.88 | 10.30 | 10.55 | 3.67 | 3.29 |
| 269 | Safflower oil methyl ester | | | | | | |
| 270 | Sesame oil methyl ester | | | | | | |
| 271 | Castor oil methyl ester | | | | | | |
| 272 | Rape-seed oil methyl ester | | | | | | |
| 273 | Olive oil methyl ester | | | | | | |
| 274 | Rice bran oil methyl ester | | | | | | |
| 275 | Cottonseed oil methyl ester | | | | | | |
| 276 | Chrysalis oil methyl ester | | | | | | |
| 277 | Sardine oil methyl ester | | | | | | |
| 278 | Fish oil methyl ester | | | | | | |
| 279 | Flatfish oil methyl ester | | | | | | |
| 280 | Safflower oil | | | | | | |
| 281 | Linseed oil | | | | | | |
| 282 | Soybean oil | | | | | | |
| 283 | Sunflower oil | | | | | | |
| 284 | Corn oil | | | | | | |
| 285 | Shark oil | | | | | | |
| 286 | Cuttlefish oil | | | | | | |
| 287 | Sardine oil | | | | | | |
| 288 | Mackerel oil | | | | | | |
| 289 | Saury pike oil | | | | | | |
| 290 | Herring oil | | | | | | |
| 291 | Saurel oil | | | | | | |
| 292 | Flatfish oil | | | | | | |
| 293 | Menhaden oil | | | | | | |
| 294 | Liver oil | | | | | | |
| 295 | Residual oil | | | | | | |
| 296 | Safflower oil (R''''=C$_3$H$_7$) | | | | | | | o R'''' = CH$_3$
* R'''' C$_2$H$_5$

EXAMPLE 297

Linoleic acid (10 g.), 5 g. of d(+)α-methylbenzylamine and 10 g. of dicyclohexyl carbodiimide were individually dissolved in 50 ml. of toluene. The solutions were mixed together at one time, and the mixed solution was allowed to stand at room temperature for 8 hours. After filtering the solution, the filtrate was washed with acid alkali and water and was dried concentrated and distilled to obtain 11.1 g. of a desired product, b.p. 201°–209° C./0.04 mmHg. Elementary analysis:

|  | Theoretical | Analytical |
|---|---|---|
| C (%) | 81.40 | 81.66 |
| H (%) | 10.77 | 10.91 |
| N (%) | 3.65 | 3.42 |

Examples 298–332 are shown in the following table:

d-RCONHCH(C₆H₅)
            |
            R''''

| Ex. No. | Acid | Amine R'''' | BN=C=NB | Solvent | b.p. °C./mmHg | C % Theoretical | C % Analytical | H % Theoretical | H % Analytical | N % Theoretical | N % Analytical |
|---|---|---|---|---|---|---|---|---|---|---|---|
| 298 | Linoleic acid | CH₃ | cyclohexyl | Ether | 200–209/0.04 | 81.40 | 81.67 | 10.77 | 10.93 | 3.65 | 3.44 |
| 299 | Linoleic acid | CH₃ | cyclohexyl | Dioxane | 201–209/0.04 | 81.40 | 81.68 | 10.77 | 10.91 | 3.65 | 3.33 |
| 300 | Oleic acid | CH₃ | (CH₃)₂CH– | Dioxane | 203–109/0.06 | 80.98 | 81.05 | 11.24 | 11.44 | 3.63 | 3.48 |
| 301 | Linolenic acid | CH₃ | cyclohexyl | Tetrahydrofuran | 205–211/0.05 | 81.83 | 82.05 | 10.30 | 10.65 | 3.67 | 3.49 |
| 302 | Isostearic acid | CH₃ | cyclohexyl | Ether | 203–214/0.07 | 80.56 | 80.72 | 11.70 | 11.97 | 3.61 | 3.51 |
| 303 | Isostearic acid | CH₃ | cyclohexyl | Toluene | 200–214/0.05 | 80.56 | 80.88 | 11.70 | 11.87 | 3.61 | 3.49 |
| 304 | Safflower oil | C₂H₅ | cyclohexyl | Toluene | 199–214/0.05 | | | | | | |
| 305 | Soybean oil | CH₃ | cyclohexyl | Chloroform | 195–213/0.05 | | | | | | |
| 306 | Sesame oil | CH₃ | cyclohexyl | Toluene | 189–216/0.07 | | | | | | |
| 307 | Castor oil | CH₃ | phenyl | Tetrachlorocarbon | 192–213/0.07 | | | | | | |
| 308 | Rape-seed oil | CH₃ | cyclohexyl | Benzene | 191–211/0.06 | | | | | | |
| 309 | Olive oil | C₂H₅ | cyclohexyl | Pyridine | 190–215/0.06 | | | | | | |
| 310 | Rice bran oil | CH₃ | cyclohexyl | Benzene | 185–214/0.06 | | | | | | |
| 311 | Cottonseed oil | CH₃ | cyclohexyl | Toluene | 193–215/0.05 | | | | | | |
| 312 | Corn oil | CH₃ | cyclohexyl | Toluene | 190–213/0.05 | | | | | | |
| 313 | Peanut oil | CH₃ | cyclohexyl | Ether | 192–218/0.06 | | | | | | |
| 314 | Olive oil | CH₃ | cyclohexyl | Toluene | 191–219/0.06 | | | | | | |

-continued d-RCONHCH—
|
R''''

| Ex. No. | Acid | Amine R'''' | BN=C=NB B | Solvent | b.p. °C./mmHg | C % Theoretical | C % Analytical | H % Theoretical | H % Analytical | N % Theoretical | N % Analytical |
|---|---|---|---|---|---|---|---|---|---|---|---|
| 315 | Chrysalis oil | CH₃ | | Toluene | 190–215/0.05 | | | | | | |
| 316 | Shark oil | CH₃ | | Benzene | 204–222/0.05 | | | | | | |
| 317 | Cuttlefish oil | CH₃ | | Toluene | 179–223/0.05 | | | | | | |
| 318 | Sardine oil | CH₃ | | Ether | 190–220/0.07 | | | | | | |
| 319 | Mackerel oil | CH₃ | | Ether | 192–215/0.05 | | | | | | |
| 320 | Saury pike oil | CH₃ | | Benzene | 190–211/0.06 | | | | | | |
| 321 | Herring oil | CH₃ | | Ether | 191–218/0.05 | | | | | | |
| 322 | Saurel oil | CH₃ | | Toluene | 181–219/0.05 | | | | | | |
| 323 | Cod oil | CH₃ | | Chloroform | 185–210/0.05 | | | | | | |
| 324 | Trout oil | CH₃ | | Tetrahydrofuran | 180–219/0.05 | | | | | | |
| 325 | Gray mullet oil | CH₃ | | Tetrahydrofuran | 191–225/0.05 | | | | | | |
| 326 | Munuke oil | CH₃ | | Toluene | 187–215/0.06 | | | | | | |
| 327 | Menhaden oil | C₂H₅ | | Dioxane | 193–225/0.05 | | | | | | |
| 328 | Eel oil | CH₃ | | Benzene | 196–220/0.05 | | | | | | |
| 329 | Flatfish oil | CH₃ | | Dioxane | 187–220/0.05 | | | | | | |
| 330 | Whale oil | CH₃ | | Benzene | 175–219/0.06 | | | | | | |
| 331 | Liver oil | CH₃ | | Toluene | 190–219/0.07 | | | | | | |
| 332 | Residual oil | C₂H₅ | | Toluene | 191–223/0.08 | | | | | | |

EXAMPLE 333

To a solution of 12.5 g. of (+)α-methylbenzylamine and 8 g. of trimethylamine in 100 ml. of anhydrous ether was added 30 g. of linoleic acid chloride in 50 ml. of anhydrous ether under stirring at 0°–5° C. After addition, the reaction mixture was boiled for 2 hours to complete the reaction. Subsequently, the ether solution was washed with acid, alkali and water and dried, concentrated and distilled to obtain 42 g. of a desired product, b.p. 207°–217° C./0.05 mmHg. Elementary analysis:

| | Theoretical | Analytical |
|---|---|---|
| C (%) | 81.46 | 81.58 |
| H (%) | 10.77 | 10.91 |
| N (%) | 3.65 | 3.41 |

Examples 334–369 are shown in the following table:

| | o α-Methyl-benzylamine | * α-Ethylbenzylamine | + α-Propylbenzylamine | | | § α-Butylbenzylamine | | | | | |
|---|---|---|---|---|---|---|---|---|---|---|---|
| | | | | | | C % | | H % | | N % | |
| Ex. No. | Acid halide acid | RCOX | X | Solvent | Condensation agent | b.p. °C./mmHg | Theoretical | Analytical | Theoretical | Analytical | Theoretical | Analytical |
| 334 | Oleic acid | o | Cl | Acetone | K₂CO₃ | 205–217/0.05 | 80.98 | 81.11 | 11.24 | 11.41 | 3.63 | 3.91 |
| 335 | Oleic acid | o | Cl | Tetrahydrofuran-water | NaOH | 207–216/0.05 | 80.98 | 81.09 | 11.24 | 11.35 | 3.63 | 3.66 |
| 336 | Isostearic acid | o | Cl | Ether | Trimethylamine | 206–218/0.06 | 80.56 | 80.77 | 11.70 | 11.91 | 3.61 | 3.42 |
| 337 | Isostearic acid | o | Cl | Toluene | Pyridine | 203–214/0.05 | 80.56 | 80.72 | 11.70 | 11.89 | 3.61 | 3.48 |
| 338 | Linoleic acid | o | Cl | Acetone | Picoline | 200–213/0.05 | 81.40 | 81.62 | 10.77 | 10.81 | 3.65 | 3.62 |
| 339 | Linoleic acid | o | Cl | Methylbutylketone | Triethylamine | 200–216/0.06 | 81.40 | 81.70 | 10.77 | 10.94 | 3.65 | 3.33 |
| 340 | Linolenic acid | o | Cl | Ether | Triethylamine | 201–217/0.05 | 81.83 | 81.93 | 10.30 | 10.54 | 3.67 | 3.44 |
| 341 | Linolenic acid | o | Cl | Benzene | Dimethylaniline | 205–215/0.04 | 81.83 | 81.95 | 10.30 | 10.63 | 3.67 | 3.46 |
| 342 | Safflower oil acid | * | Cl | Dioxane-water | KOH | 198–208/0.05 | | | | | | |
| 343 | Soybean oil acid | o | Cl | Acetone-water | K₂CO₃ | 195–210/0.06 | | | | | | |
| 344 | Sesame oil acid | o | Cl | Ether | Pyridine | 198–211/0.06 | | | | | | |
| 345 | Castor oil | o | Cl | Ether | Pyridine | 193–216/0.04 | | | | | | |
| 346 | Rape-seed oil | o | Cl | Ether | Pyridine | 201–222/0.06 | | | | | | |
| 347 | Olive oil | * | Cl | Toluene | Trimethylamine | 188–213/0.05 | | | | | | |
| 348 | Rice bran oil | o | Cl | Toluene | Triethylamine | 187–213/0.06 | | | | | | |
| 349 | Cottonseed oil | o | Cl | Benzene | Pyridine | 194–218/0.05 | | | | | | |
| 350 | Chrysalis acid | o | Cl | Toluene | Pyridine | 190–214/0.06 | | | | | | |
| 351 | Corn oil | o | Cl | Acetone-water | NaOH | 203–221/0.08 | | | | | | |
| 352 | Linseed oil | o | Cl | Ether | Pyridine | 190–215/0.06 | | | | | | |
| 353 | Sunflower oil | o | Cl | Tetrahydrofuran-water | NaOH | 193–212/0.05 | | | | | | |
| 354 | Flatfish oil | o | Cl | Methylbutylketone | K₂CO₃ | 188–214/0.04 | | | | | | |
| 355 | Shark oil | * | Cl | Acetone-water | | 183–218/0.04 | | | | | | |
| 356 | Whale oil | o | Cl | Acetone-water | Na₂CO₃ | 183–208/0.05 | | | | | | |
| 357 | Cuttlefish oil | o | Cl | Dioxane-water | NaOH | 180–214/0.05 | | | | | | |
| 358 | Sardine oil | * | Cl | Dioxane-water | K₂CO₃ | 190–213/0.05 | | | | | | |
| 359 | Mackerel oil | o | Cl | Toluene | Pyridine | 192–211/0.05 | | | | | | |
| 360 | Saury pike oil | o | Cl | Dioxane-water | NaOH | 190–210/0.05 | | | | | | |
| 361 | Herring oil | o | Cl | Toluene | Pyridine | 193–214/0.05 | | | | | | |
| 362 | Saurel oil | o | Cl | Acetone-water | NaOH | 183–219/0.05 | | | | | | |
| 363 | Menhaden oil | o | Cl | Toluene | Pyridine | 193–223/0.05 | | | | | | |
| 364 | Cod oil | o | Cl | Acetone-water | KOH | 186–209/0.05 | | | | | | |
| 365 | Liver oil | * | Cl | Ether | Pyridine | 190–214/0.04 | | | | | | |
| 366 | Residual oil | o | Cl | Acetone-water | KOH | 187–219/0.06 | | | | | | |
| 367 | Menuke oil | o | Cl | Acetone-water | NaOH | 188–208/0.06 | | | | | | |
| 368 | Safflower oil | § | Cl | Acetone-water | NaOH | 193–206/0.06 | | | | | | |
| 369 | Safflower oil | + | Cl | Acetone-water | NaOH | 197–211/0.08 | | | | | | |

EXAMPLE 370

A mixture of 10 g. of linoleic acid and 6 g. of d(+)α-methylbenzylamine was heated at 180° C. for 24 hours while removing water out of the reaction system during the reaction. After completion of the reaction, the reaction mixture was immediately distilled to obtain 11.3 g. of a desired product, b.p. 203° – 221° C./0.07 mmHg. Elementary analysis:

| | Theoretical | Analytical |
|---|---|---|
| C (%) | 81.40 | 81.66 |
| H (%) | 10.77 | 10.90 |
| N (%) | 3.65 | 3.42 |

Examples 371–396 are as shown in the following table:

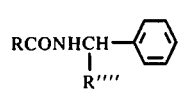

| Example No. | Acid | R'''' | Reaction temperature | Reaction time (hr.) | b.p. °C./mmHg | C % Theoretical | Analytical | H % Theoretical | Analytical | N % Theoretical | Analytical |
|---|---|---|---|---|---|---|---|---|---|---|---|
| 371 | Isostearic acid | o | 180 | 24 | 205–218/0.06 | 80.56 | 80.77 | 11.70 | 11.97 | 3.61 | 3.30 |
| 372 | Oleic acid | o | 180 | 24 | 205–217/0.05 | 80.98 | 81.30 | 11.24 | 11.63 | 3.63 | 3.29 |
| 373 | Linolenic acid | o | 180 | 24 | 208–216/0.06 | 81.83 | 81.96 | 10.30 | 10.61 | 3.67 | 3.38 |
| 374 | Safflower oil acid | o | 180 | 24 | 195–219/0.07 | | | | | | |
| 375 | Soybean oil acid | o | 200 | 20 | 198–221/0.05 | | | | | | |
| 376 | Corn oil acid | o | 180 | 20 | 194–209/0.06 | | | | | | |
| 377 | Cottonseed oil acid | x | 180 | 24 | 196–213/0.05 | | | | | | |
| 378 | Sesame oil acid | o | 160 | 36 | 198–206/0.04 | | | | | | |

-continued

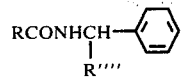

| Example No. | Acid | R'''' | Reaction temperature | Reaction time (hr.) | b.p. °C./mmHg | C % Theoretical | C % Analytical | H % Theoretical | H % Analytical | N % Theoretical | N % Analytical |
|---|---|---|---|---|---|---|---|---|---|---|---|
| 379 | Castor oil acid | o | 160 | 36 | 200–221/0.04 | | | | | | |
| 380 | Olive oil acid | o | 180 | 24 | 188–211/0.06 | | | | | | |
| 381 | Rape-seed oil acid | o | 180 | 24 | 200–216/0.05 | | | | | | |
| 382 | Sunflower oil acid | o | 180 | 24 | 193–211/0.06 | | | | | | |
| 383 | Linseed-oil acid | o | 180 | 24 | 188–216/0.05 | | | | | | |
| 384 | Rice bran oil acid | o | 180 | 24 | 189–215/0.07 | | | | | | |
| 385 | Shark oil acid | x | 180 | 24 | 184–220/0.05 | | | | | | |
| 386 | Whale oil acid | o | 180 | 26 | 172–223/0.04 | | | | | | |
| 387 | Mackerel oil acid | o | 180 | 24 | 193–209/0.06 | | | | | | |
| 388 | Saurel oil acid | o | 180 | 24 | 189–216/0.07 | | | | | | |
| 389 | Cuttlefish oil acid | o | 200* | 18 | 186–217/0.06 | | | | | | |
| 390 | Cod oil acid | o | 200* | 18 | 188–223/0.08 | | | | | | |
| 391 | Herring oil acid | o | 210* | 18 | 193–212/0.04 | | | | | | |
| 392 | Sardine oil acid | o | 180 | 20 | 190–220/0.08 | | | | | | |
| 393 | Flatfish oil acid | o | 180 | 24 | 197–221/0.05 | | | | | | |
| 394 | Manhaden oil acid | o | 180 | 24 | 190–218/0.06 | | | | | | |
| 395 | Liver oil acid | o | 180 | 20 | 193–220/0.05 | | | | | | |
| 396 | Residual oil acid | o | 180 | 20 | 185–216/0.05 | | | | | | |

*In an autoclave
o R'''' = $CH_3$
x R'''' = $C_2H_5$

EXAMPLE 397

To a solution of 14 g. of linoleic acid and 5.5 g. of triethylamine in 100 cc. of tetrahydrofuran was added 5.9 g. of ethyl chloroformate under stirring at −10° to −5° C. After addition, the stirring was continued at −5° C. for additional 20 minutes. Subsequently, 6.5 g. of d(+)α-methylbenzylamine was added dropwise with stirring at −5° C. After the dropwise addition, the ice water bath was removed and stirring was continued until the temperature reached room temperature. Subsequently, the temperature was gradually increased, and stirring was continued at 40° C. for 20 minutes. After cooling, tetrahydrofuran was removed by distillation under reduced pressure, and the residue was dissolved in ether. The solution was washed with cold dilute aqueous solution of hydrochloric acid, sodium carbonate and water, and was dried over anhydrous sodium carbonate. The ether was removed by distillation and the residue was distilled in vacuo to obtain 15.8 g. of a desired product, b.p. 202°–207° C./0.03 mmHg, [α]$_D$ + 50.0. Elementary analysis:

| | Theoretical | Analytical |
|---|---|---|
| C (%) | 81.40 | 81.72 |
| H (%) | 10.77 | 10.89 |
| N (%) | 3.65 | 3.42 |

In the same manner as in Example 397, each 1 mole of fatty acids and each 1–1.1 moles of basic substances were individually dissolved in a solvent in an amount of 7 to 10 times the amount of the acid. To the solutions was added 1–1.1 moles of chloroformate dropwise under stirring at −5° to −10° C. After addition, the mixtures were stirred at said temperature for 10–30 minutes. Subsequently, each 1–1.1 moles of amine derivative was added dropwise under stirring to the solution. During about 10 minutes after addition, the reaction was completed essentially. In some case, if necessary, the mixtures were heated to 40°–50° C. Thereafter, the mixtures were treated according to ordinary procedures to obtain in 40–85% yields such compounds as seen in Examples 398 to 551, which are shown in the following tables:

| Example No. | Acid | R'''' | b.p. °C./mmHg | C % Theoretical | C % Analytical | H % Theoretical | H % Analytical | N % Theoretical | N % Analytical |
|---|---|---|---|---|---|---|---|---|---|
| 398 | Linoleic acid | d-$CH_3$ | 201–209/0.04 | 81.40 | 81.66 | 10.77 | 10.95 | 3.65 | 3.58 |
| 399 | Linoleic acid | l-$CH_3$ | 200–209/0.04 | 81.40 | 81.58 | 10.77 | 10.84 | 3.65 | 3.63 |
| 400 | Oleic acid | d-$CH_3$ | 205–209/0.04 | 80.98 | 81.04 | 11.24 | 11.34 | 3.63 | 3.58 |
| 401 | Linolenic acid | d-$CH_3$ | 205–213/0.05 | 81.83 | 82.03 | 10.30 | 10.35 | 3.67 | 3.47 |
| 402 | Isostearic acid | d-$CH_3$ | 202–214/0.07 | 80.56 | 80.62 | 11.70 | 11.97 | 3.61 | 3.52 |
| 403 | Isostearic acid | l-$CH_3$ | 201–213/0.05 | 80.56 | 80.73 | 11.70 | 11.89 | 3.61 | 3.48 |
| 404 | Safflower oil | d-$C_2H_5$ | 199–213/0.03 | | | | | | |
| 405 | Soybean oil | l-$CH_3$ | 193–215/0.04 | | | | | | |
| 406 | Sesame oil | d-$CH_3$ | 188–214/0.07 | | | | | | |
| 407 | Castor oil | d-$CH_3$ | 194–211/0.07 | | | | | | |
| 408 | Rape-seed oil | l-$CH_3$ | 190–210/0.06 | | | | | | |
| 409 | Olive oil | d-$C_2H_5$ | 193–215/0.06 | | | | | | |
| 410 | Rice bran oil | l-$CH_3$ | 185–210/0.06 | | | | | | |
| 411 | Cottonseed oil | d-$CH_3$ | 195–214/0.05 | | | | | | |
| 412 | Corn oil | d-$CH_3$ | 191–218/0.05 | | | | | | |

-continued

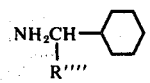

| Example No. | Acid | R'''' | b.p. °C./mmHg | C % Theoretical | C % Analytical | H % Theoretical | H % Analytical | N % Theoretical | N % Analytical |
|---|---|---|---|---|---|---|---|---|---|
| 413 | Peanut oil | d-$CH_3$ | 193–217/0.06 | | | | | | |
| 414 | Olive oil | d-$CH_3$ | 191–209/0.06 | | | | | | |
| 415 | Chrysalis oil | d-$CH_3$ | 198–215/0.04 | | | | | | |
| 416 | Shark oil | d-$CH_3$ | 202–222/0.04 | | | | | | |
| 417 | Cuttlefish oil | d-$CH_3$ | 178–225/0.04 | | | | | | |
| 418 | Sardine oil | d-$CH_3$ | 194–222/0.06 | | | | | | |
| 419 | Mackerel oil | l-$CH_3$ | 191–214/0.05 | | | | | | |
| 420 | Saury pike oil | l-$CH_3$ | 197–211/0.05 | | | | | | |
| 421 | Herring oil | d-$CH_3$ | 191–218/0.05 | | | | | | |
| 422 | Saurel oil | d-$CH_3$ | 184–219/0.05 | | | | | | |
| 423 | Cod oil | l-$CH_3$ | 185–214/0.05 | | | | | | |
| 424 | Trout oil | l-$CH_3$ | 180–218/0.05 | | | | | | |
| 425 | Gray mullet oil | d-$CH_3$ | 193–225/0.04 | | | | | | |
| 426 | Menuke oil | d-$CH_3$ | 189–215/0.05 | | | | | | |
| 427 | Menhaden oil | l-$C_2H_5$ | 193–225/0.05 | | | | | | |
| 428 | Eel oil | d-$CH_3$ | 195–219/0.05 | | | | | | |
| 429 | Flatfish oil | l-$CH_3$ | 188–220/0.05 | | | | | | |
| 430 | Whale oil | l-$CH_3$ | 178–219/0.06 | | | | | | |
| 431 | Liver oil | d-$CH_3$ | 192–217/0.05 | | | | | | |
| 432 | Residual oil | d-$C_2H_5$ | 191–222/0.08 | | | | | | |

| Ex. No. | Acid | Amine | b.p. °C./mmHg | C % Theoretical | C % Analytical | H % Theoretical | H % Analytical | N % Theoretical | N % Analytical |
|---|---|---|---|---|---|---|---|---|---|
| 433 | Linoleic acid | $NH_2CH(CH_3)$–C$_6H_4$–$CH_3$ (o) | 202–212/0.04 | 81.55 | 81.70 | 10.90 | 11.07 | 3.52 | 3.56 |
| 434 | Linoleic acid | $NH_2CH(CH_3)$–C$_6H_4$–$CH_3$ (m) | 203–216/0.05 | 81.55 | 81.65 | 10.90 | 11.05 | 3.52 | 3.64 |
| 435 | Linoleic acid | $NH_2CH(CH_3)$–C$_6H_4$–$CH_3$ (d, p) | 208–214/0.04 | 81.55 | 81.74 | 10.90 | 11.08 | 3.52 | 3.72 |
| 436 | Linoleic acid | $NH_2CH(C_2H_5)$–C$_6H_4$–$CH_3$ (o) | 199–216/0.05 | 81.69 | 81.87 | 11.02 | 11.48 | 3.40 | 3.40 |
| 437 | Linoleic acid | $NH_2CH(CH_3)$–C$_6H_4$–Cl (o) | 220–223/0.08 | 74.69 | 74.77 | 9.65 | 9.71 | 3.35 | 3.48 |
| 438 | Linoleic acid | $NH_2CH(CH_3)$–C$_6H_4$–Cl (m) | 222–224/0.07 | 74.69 | 74.82 | 9.65 | 9.73 | 3.35 | 3.37 |
| 439 | Linoleic acid | $NH_2CH(CH_3)$–C$_6H_4$–Cl (p) | 220–226/0.08 | 74.69 | 74.58 | 9.65 | 9.96 | 3.35 | 3.49 |
| 440 | Linoleic acid | $NH_2CH(CH_3)$–C$_6H_3$–Cl$_2$ | 225–240/0.08 | 69.01 | 69.90 | 8.69 | 8.79 | 3.10 | 3.32 |

-continued

| Ex. No. | Acid | Amine | b.p. °C./mmHg | C % Theoretical | C % Analytical | H % Theoretical | H % Analytical | N % Theoretical | N % Analytical |
|---|---|---|---|---|---|---|---|---|---|
| 441 | Linoleic acid | NH₂CH(CH₃)—C₆H₄—Br (p) | 225–234/0.2 | 67.52 | 67.66 | 8.72 | 8.76 | 3.03 | 3.27 |
| 442 | Linoleic acid | NH₂CH(CH₃)—C₆H₄—Br (o) | 223–238/0.1 | 67.52 | 67.54 | 8.72 | 8.75 | 3.03 | 3.08 |
| 443 | Linoleic acid | NH₂CH(CH₃)—C₆H₄—Br (m) | 224–236/0.1 | 67.52 | 67.68 | 8.72 | 8.82 | 3.03 | 3.19 |
| 444 | Linoleic acid | NH₂CH(C₂H₅)—C₆H₄—Br | 218–237/0.09 | 68.06 | 68.09 | 8.82 | 8.84 | 2.94 | 3.05 |
| 445 | Linoleic acid | (l) NH₂CH(CH₃)—C₆H₄—CH₃ | 210–224/0.04 | 81.55 | 81.58 | 10.90 | 10.94 | 3.52 | 3.58 |
| 446 | Linoleic acid | (l) NH₂CH(CH₃)—C₆H₄—Cl | 217–220/0.08 | 74.69 | 74.73 | 9.65 | 9.83 | 3.35 | 3.50 |
| 447 | Linoleic acid | (d) NH₂CH(CH₃)—C₆H₄—Cl | 217–226/0.08 | 74.69 | 74.63 | 9.65 | 9.70 | 3.35 | 3.25 |
| 448 | Linoleic acid | NH₂CH(CH₃)—C₆H₄—OCH₃ (o) | 220–223/0.09 | 78.40 | 78.29 | 10.48 | 10.34 | 3.39 | 3.38 |
| 449 | Linoleic acid | NH₂CH(CH₃)—C₆H₄—OCH₃ (m) | 209–223/0.09 | 78.40 | 78.38 | 10.48 | 10.33 | 3.39 | 3.29 |
| 450 | Linoleic acid | NH₂CH(CH₃)—C₆H₄—OCH₃ (p) | 218–223/0.1 | 78.40 | 78.37 | 10.48 | 10.37 | 3.39 | 3.24 |
| 451 | Oleic acid | NH₂CH(CH₃)—C₆H₄—C₂H₅ | 212–222/0.08 | 81.29 | 81.31 | 11.45 | 11.45 | 3.39 | 3.54 |
| 452 | Oleic acid | NH₂CH(C₂H₅)—C₆H₄—C₂H₅ | 212–223/0.09 | 81.44 | 81.56 | 11.55 | 11.59 | 3.28 | 3.56 |
| 453 | Oleic acid | NH₂CH(CH₃)—C₆H₄—Br | 224–231/0.09 | 67.24 | 67.34 | 9.05 | 8.94 | 3.01 | 3.29 |
| 454 | Isostearic acid | NH₂CH(CH₃)—C₆H₄—CH₃ | 202–217/0.08 | 80.73 | 80.74 | 11.83 | 12.92 | 3.49 | 3.52 |
| 455 | Isostearic acid | NH₂CH(C₂H₅)—C₆H₄—C(CH₃)₃ | 208–231/0.1 | 81.33 | 81.42 | 12.11 | 12.22 | 3.06 | 3.18 |

-continued

| Ex. No. | Acid | Amine | b.p. °C./mmHg | C % Theoretical | C % Analytical | H % Theoretical | H % Analytical | N % Theoretical | N % Analytical |
|---|---|---|---|---|---|---|---|---|---|
| 456 | Isostearic acid | NH₂CH(CH₃)—C₆H₄—Cl | 221–228/0.09 | 74.02 | 74.23 | 10.43 | 10.56 | 3.32 | 3.41 |
| 457 | Isostearic acid | NH₂CH(CH₂)—C₆H₄—Br | 223–241/0.1 | 66.95 | 67.04 | 9.44 | 9.58 | 3.00 | 3.20 |
| 458 | Isostearic acid | NH₂CH(CH₃)—C₆H₄—OCH₃ | 220–224/0.05 | 77.64 | 77.64 | 11.34 | 11.45 | 3.35 | 3.25 |
| 459 | Isostearic acid | NH₂CH(C₂H₅)—C₆H₄—OC₂H₅ | 220–230/0.09 | 78.14 | 78.24 | 11.53 | 11.55 | 3.14 | 3.09 |
| 460 | Linolenic acid | NH₂CH(CH₃)—C₆H₄—OC₂H₅ | 220–237/0.08 | 79.61 | 79.73 | 10.18 | 10.34 | 3.29 | 3.33 |
| 461 | Linolenic acid | NH₂CH(C₂H₅)—C₆H₄—OCH₃ | 215–229/0.1 | 79.61 | 79.77 | 10.18 | 10.32 | 3.29 | 3.40 |
| 462 | Linolenic acid | NH₂CH(CH₃)—C₆H₄—CH₃ | 221–242/0.09 | 81.97 | 82.04 | 10.45 | 10.65 | 3.54 | 3.48 |
| 463 | Linolenic acid | NH₂CH(CH₃)—C₆H₄—Cl | 217–238/0.2 | 75.09 | 75.19 | 9.14 | 10.07 | 3.36 | 3.37 |
| 464 | Linseed oil acid | NH₂CH(CH₃)—C₆H₄—CH₃ | 199–218/0.09 | | | | | | |
| 465 | Linseed oil acid | NH₂CH(CH₃)—C₆H₄—Cl | 222–228/0.08 | | | | | | |
| 466 | Safflower oil acid | NH₂CH(CH₃)—C₆H₄—CH₃ | 204–209/0.06 | | | | | | |
| 467 | Safflower oil acid | NH₂CH(C₂H₅)—C₆H₄—CH₃ | 203–212/0.06 | | | | | | |
| 468 | Safflower oil acid | NH₂CH(CH₃)—C₆H₄—OC₂H₅ | 219–229/0.06 | | | | | | |
| 469 | Safflower oil acid | NH₂CH(C₂H₅)—C₆H₄—Br | 220–224/0.1 | | | | | | |
| 470 | Soybean oil acid | NH₂CH(C₃H₇)—C₆H₄—C₃H₇ | 219–235/0.06 | | | | | | |

| Ex. No. | Acid | Amine | b.p. °C./mmHg | C % Theoretical | C % Analytical | H % Theoretical | H % Analytical | N % Theoretical | N % Analytical |
|---|---|---|---|---|---|---|---|---|---|
| 471 | Sunflower oil acid | NH₂CH(C₃H₇)—C₆H₄—OC₄H₉ | 220–240/0.05 | | | | | | |
| 472 | Castor oil acid | NH₂CH(CH₃)—C₆H₃(Cl)(Cl) | 217–227/0.06 | | | | | | |
| 473 | Rape-seed oil acid | NH₂CH(CH₃)—C₆H₄—OC₂H₅ | 220–226/0.06 | | | | | | |
| 474 | Cottonseed oil acid | NH₂CH(C₃H₇)—C₆H₄—OCH₃ | 222–229/0.05 | | | | | | |
| 475 | Olive oil acid | NH₂CH(CH₃)—C₆H₄—C₂H₅ | 215–227/0.05 | | | | | | |
| 476 | Peanut oil acid | (l) NH₂CH(CH₃)—C₆H₄—OCH₃ | 220–225/0.05 | | | | | | |
| 477 | Locust oil acid | (d) NH₂CH(CH₃)—C₆H₄—OCH₃ | 222–226/0.06 | | | | | | |
| 478 | Chrysalis oil acid | NH₂CH(C₂H₅)—C₆H₃(CH₃)(Cl) | 231–240/0.05 | | | | | | |
| 479 | Shark oil acid | NH₂CH(CH₃)—C₆H₃(OCH₃)(CH) | 223–240/0.05 | | | | | | |
| 480 | Sardine oil acid | NH₂CH(CH₃)—C₆H₄—OC₂H₅ | 217–231/0.05 | | | | | | |
| 481 | Mackerel oil acid | NH₂CH(CH₃)—C₆H₄—Br | 220–225/0.06 | | | | | | |
| 482 | Herring oil acid | NH₂CH(CH₃)—C₆H₄—CH₃ | 195–220/0.06 | | | | | | |
| 483 | Saurel oil acid | NH₂CH(CH₃)—C₆H₄—C₄H₉ | 201–230/0.05 | | | | | | |
| 484 | Cod oil acid | NH₂CH(C₄H₉)—C₆H₄—CH₃ | 200–225/0.04 | | | | | | |
| 485 | Gray mullet oil acid | NH₂CH(CH₃)—C₆H₄—OCH₃ | 196–236/0.05 | | | | | | |

-continued

| Ex. No. | Acid | Amine | b.p. °C./mmHg | C % Theoretical | C % Analytical | H % Theoretical | H % Analytical | N % Theoretical | N % Analytical |
|---|---|---|---|---|---|---|---|---|---|
| 486 | Menhaden oil acid | NH₂CH(CH₃)—C₆H₄—OCH₃ | 181–241/0.06 | | | | | | |
| 487 | Flatfish oil acid | NH₂CH(C₂H₅)—C₆H₄—Cl | 195–240/0.08 | | | | | | |
| 488 | Residual oil acid | NH₂CH(CH₃)—C₆H₄—OC₂H₅ | 204–235/0.05 | | | | | | |

| Example No. | Acid moiety | Amine moiety | n_D | C % Theoretical | C % Analytical | H % Theoretical | H % Analytical | N % Theoretical | N % Analytical |
|---|---|---|---|---|---|---|---|---|---|
| 489 | Linoleic acid | NH₂CH(CH₃)—C₆H₄—NO₂ | 23°C. 1.5111 | 72.86 | 72.93 | 9.41 | 9.60 | 6.54 | 6.49 |
| 490 | Oleic acid | NH₂CH(C₂H₅)—C₆H₄—NO₂ | 22°C. 1.5124 | 72.93 | 73.06 | 9.97 | 10.03 | 6.30 | 6.25 |
| 491 | Linolenic acid | NH₂CH(C₂H₅)—C₆H₄—NO₂ | 23°C. 1.5100 | 73.60 | 73.80 | 9.15 | 9.30 | 6.36 | 6.24 |
| 492 | Linoleic acid | NH₂CH(C₂H₅)—C₆H₄—NO₂ | 23°C. 1.5154 | 73.26 | 73.32 | 9.56 | 9.52 | 6.33 | 6.24 |
| 493 | Linoleic acid | NH₂CH(CH₃)—C₆H₄—NO₂ | 26°C. 1.5109 | 72.86 | 72.89 | 9.41 | 9.48 | 6.54 | 6.37 |
| 494 | Isostearic acid | NH₂CH(d)(CH₃)—C₆H₄—NO₂ | 27°C. 1.5156 | 72.18 | 72.24 | 10.25 | 10.40 | 6.48 | 6.34 |
| 495 | Isostearic acid | NH₂CH(l)(CH₃)—C₆H₄—NO₂ | 28°C. 1.5152 | 72.18 | 72.20 | 10.25 | 10.36 | 6.48 | 6.34 |
| 496 | Safflower oil acid | NH₂CH(CH₃)—C₆H₄—NO₂ | 22°C. 1.5139 | | | | | | |
| 497 | Soybean oil acid | NH₂CH(C₂H₅)—C₆H₄—NO₂ | 20°C. 1.5131 | | | | | | |
| 498 | Sesame oil acid | NH₂—C₆H₄(CH₃)(NO₂) | 22°C. 1.5107 | | | | | | |
| 499 | Castor oil acid | NH₂CH(CH₃)—C₆H₄—NO₂ | 22°C. 1.5122 | | | | | | |
| 500 | Corn oil acid | NH₂CH(C₃H₇)—C₆H₄—NO₂ | 24°C. 1.5123 | | | | | | |

-continued

| Example No. | Acid moiety | Amine moiety | n_D | | C % Theoretical | C % Analytical | H % Theoretical | H % Analytical | N % Theoretical | N % Analytical |
|---|---|---|---|---|---|---|---|---|---|---|
| 501 | Cottonseed oil acid | NH₂CH(CH₃)—C₆H₄—NO₂ | 23°C. | 1.5129 | | | | | | |
| 502 | Olive oil acid | NH₂CH(CH₃)—C₆H₄—NO₂ | 25°C. | 1.5138 | | | | | | |
| 503 | Linseed oil acid | NH₂CH(CH₃)—C₆H₄—NO₂ | 28°C. | 1.5119 | | | | | | |
| 504 | Rape-seed oil acid | NH₂CH(CH₃)—C₆H₄—NO₂ | 14.5°C. | 1.5139 | | | | | | |
| 505 | Rice bran oil acid | NH₂CH(CH₃)—C₆H₄—NO₂ | 18°C. | 1.5123 | | | | | | |
| 506 | Chrysalis oil acid | NH₂CH(CH₃)—C₆H₄—NO₂ | 23°C. | 1.5100 | | | | | | |
| 507 | Flatfish oil acid | NH₂CH(CH₃)—C₆H₄—NO₂ | 22°C. | 1.5122 | | | | | | |
| 508 | Shark oil acid | NH₂CH(C₂H₅)—C₆H₄—NO₂ | 20°C. | 1.5148 | | | | | | |
| 509 | Whale oil acid | NH₂CH(CH₃)—C₆H₄—NO₂ | 23°C. | 1.5134 | | | | | | |
| 510 | Cuttlefish oil acid | NH₂CH(CH₃)—C₆H₄—NO₂ | 28°C. | 1.5120 | | | | | | |
| 511 | Sardine oil acid | NH₂CH(CH₃)—C₆H₄—NO₂ | 23°C. | 1.5221 | | | | | | |
| 512 | Mackerel oil acid | NH₂CH(CH₃)—C₆H₄—NO₂ | 23°C. | 1.5145 | | | | | | |
| 513 | Saury pike oil acid | NH₂CH(CH₃)—C₆H₄—NO₂ | 28°C. | 1.5235 | | | | | | |
| 514 | Herring oil acid | NH₂CH(CH₃)—C₆H₄—NO₂ | 30°C. | 1.5114 | | | | | | |
| 515 | Saurel oil acid | NH₂(CH₃)—C₆H₄—NO₂ | 30°C. | 1.5138 | | | | | | |
| 516 | Menhaden oil acid | NH₂CH(CH₃)—C₆H₄—NO₂ | 32°C. | 1.5149 | | | | | | |
| 517 | Cod oil acid | NH₂CH(CH₃)—C₆H₄—NO₂ | 32°C. | 1.5130 | | | | | | |
| 518 | Liver oil acid | NH₂CH(CH₃)—C₆H₄—NO₂ | 25°C. | 1.5208 | | | | | | |

-continued

| Example No. | Acid moiety | Amine moiety | $n_D$ | C % Theoretical | C % Analytical | H % Theoretical | H % Analytical | N % Theoretical | N % Analytical |
|---|---|---|---|---|---|---|---|---|---|
| 519 | Menuke oil acid | $NH_2CH{-}\langle\rangle{-}NO_2$ ; $CH_3$ | 21.5°C. 1.5140 | | | | | | |
| 520 | Residual oil acid | $NH_2CH{-}\langle\rangle{-}NO_2$ ; $C_2H_5$ | 20.5°C. 1.5133 | | | | | | |

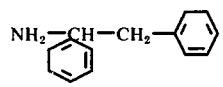

| Example No. | Acid moiety | Amine moiety | Properties | C % Theoretical | C % Analytical | H% Theoretical | H% Analytical | N% Theoretical | N% Analytical |
|---|---|---|---|---|---|---|---|---|---|
| 521 | Linoleic acid | d (+) | mp 45°–48°C. | 83.60 | 83.76 | 9.87 | 10.08 | 3.05 | 3.14 |
| 522 | Linoleic acid | l (−) | mp 45°–48°C. | 83.60 | 83.69 | 9.87 | 10.04 | 3.05 | 3.14 |
| 523 | Linoleic acid | dl (±) | mp 45°–48°C. | 83.60 | 83.67 | 9.87 | 10.00 | 3.05 | 3.13 |
| 524 | Oleic acid | dl (±) | Waxy semi solid | 83.24 | 83.35 | 10.26 | 10.32 | 3.03 | 3.14 |
| 525 | Isostearic acid | dl (±) | " | 82.88 | 83.04 | 10.65 | 10.44 | 3.02 | 3.18 |
| 526 | Isostearic acid | d (+) | " | 82.88 | 83.05 | 10.65 | 10.89 | 3.02 | 3.08 |
| 527 | Isostearic acid | l (−) | " | 82.88 | 83.06 | 10.65 | 10.67 | 3.02 | 3.08 |
| 528 | Linolenic aid | dl (±) | " | 83.97 | 84.12 | 9.47 | 9.73 | 3.06 | 3.22 |
| 529 | Linseed oil fatty acid | dl (±) | " | | | | | | |
| 530 | Safflower oil fatty acid | d (+) | " | | | | | | |
| 531 | Safflower oil fatty acid | l (−) | " | | | | | | |
| 532 | Safflower oil fatty acid | dl (±) | " | | | | | | |
| 533 | Soybean oil acid | dl (±) | " | | | | | | |
| 534 | Sunflower oil acid | dl (±) | " | | | | | | |
| 535 | Castor oil acid | " | " | | | | | | |
| 536 | Rape-seed oil acid | " | " | | | | | | |
| 537 | Cottonseed oil acid | " | " | | | | | | |
| 538 | Olive oil acid | " | " | | | | | | |
| 539 | Peanut oil acid | " | " | | | | | | |
| 540 | Locust oil acid | " | " | | | | | | |
| 541 | Chrysalis oil acid | " | " | | | | | | |
| 542 | Shark oil acid | " | " | | | | | | |
| 543 | Sardine oil acid | " | " | | | | | | |
| 544 | Mackerel oil acid | " | " | | | | | | |
| 545 | Herring oil acid | " | " | | | | | | |
| 546 | Saurel oil acid | " | " | | | | | | |
| 547 | Cod oil acid | " | " | | | | | | |
| 548 | Gray mullet oil acid | " | " | | | | | | |
| 549 | Menhaden oil acid | " | " | | | | | | |
| 550 | Flatfish oil acid | " | " | | | | | | |
| 551 | Residual oil acid | " | " | | | | | | |

EXAMPLE 552

A solution of 14 g. of linoleic acid in 30 ml. of ether, a solution of 7 g. of α,β-dimethylbenzylamine in 30 ml. of ether, and a solution of 11 g. of dicyclohexyl carbodiimide in 30 ml. of ether were mixed together at one time, and the mixed solution was allowed to stand overnight at room temperature.

Excess dicyclohexyl carbodiimide was decomposed with 2 cc. of acetic acid, and precipitated dicyclohexylurea was removed by filtration. Subsequently, the filtrate was dissolved in 100 ml. of ether, and the ether solution was washed with 5% hydrochloric acid water, 5% caustic soda water and water, and was then dried, concentrated and distilled to obtain 16.1 g. of a desired product, b.p. 198°–222° C./0.06 mmHg. Elementary analysis:

| | Theoretical | Analytical |
|---|---|---|
| C (%) | 81.55 | 81.76 |
| H (%) | 10.90 | 11.02 |
| N (%) | 3.52 | 3.82 |

Examples 553–607 are shown in the following table:

| Ex. No. | Acid | Amine | B BN=C=NB | Solvent | Reaction time (h) | b.p. °C./ mmHg | C % Theoretical | C % Analytical | H % Theoretical | H % Analytical | N % Theoretical | N % Analytical |
|---|---|---|---|---|---|---|---|---|---|---|---|---|
| 553 | Linoleic acid | NH₂CH(CH₃)-C₆H₄-CH₃ | cyclohexyl | Ether | 18 | 203–218/ 0.05 | 81.55 | 81.66 | 10.90 | 11.06 | 3.52 | 3.68 |
| 554 | Linoleic acid | (d) NH₂CH(CH₃)-C₆H₄-CH₃ | cyclohexyl | Ether | 18 | 208–221/ 0.04 | 81.55 | 81.76 | 10.90 | 11.23 | 3.52 | 3.71 |
| 555 | Linoleic acid | NH₂CH(C₂H₅)-C₆H₄-CH₃ | cyclohexyl | Toluene | 18 | 199–217/ 0.05 | 81.69 | 81.37 | 11.02 | 11.45 | 3.40 | 3.52 |
| 556 | Linoleic acid | NH₂CH(CH₃)-C₆H₄-Cl | cyclohexyl | Benzene | 18 | 220–223/ 0.08 | 74.69 | 74.79 | 9.65 | 9.91 | 3.35 | 3.47 |
| 557 | Linoleic acid | NH₂CH(CH₃)-C₆H₄-Cl | cyclohexyl | Benzene | 5 | 222–225/ 0.07 | 74.69 | 74.81 | 9.65 | 9.93 | 3.35 | 3.39 |
| 558 | Linoleic acid | NH₂CH(CH₃)-C₆H₄-Cl | cyclohexyl | Benzene | 18 | 220–225/ 0.08 | 74.69 | 74.38 | 9.65 | 9.90 | 3.35 | 3.59 |
| 559 | Linoleic acid | NH₂CH(CH₃)-C₆H₃-Cl₂ | cyclohexyl | Benzene | 5 | 225–240/ 0.08 | 69.01 | 69.88 | 8.69 | 8.79 | 3.10 | 3.52 |
| 560 | Linoleic acid | NH₂CH(CH₃)-C₆H₄-Br | —CH(CH₃)₂ | Toluene | 20 | 225–235/ 0.2 | 67.52 | 67.63 | 8.72 | 8.76 | 3.03 | 3.28 |
| 561 | Linoleic acid | NH₂CH(CH₃)-C₆H₄-Br | —CH(CH₃)₂ | Dioxane | 11 | 225–233/ 0.1 | 67.52 | 67.61 | 8.72 | 8.77 | 3.03 | 3.30 |
| 562 | Linoleic acid | NH₂CH(CH₃)-C₆H₄-Br | —CH(CH₃)₂ | Ether | 5 | 221–238/ 0.1 | 67.52 | 67.70 | 8.72 | 8.80 | 3.03 | 3.29 |
| 563 | Linoleic acid | NH₂CH(C₂H₅)-C₆H₄-Br | phenyl | Benzene | 20 | 222–238/ 0.09 | 68.06 | 68.29 | 8.82 | 8.94 | 2.94 | 3.06 |
| 564 | Linoleic acid | (l) NH₂CH(CH₃)-C₆H₄-CH₃ | cyclohexyl | Benzene | 18 | 208–221/ 0.04 | 81.55 | 81.55 | 10.90 | 10.74 | 3.52 | 3.68 |
| 565 | Linoleic acid | (l) NH₂CH(CH₃)-C₆H₄-Cl | cyclohexyl | Chloroform | 12 | 220–225/ 0.08 | 74.69 | 74.83 | 9.65 | 9.83 | 3.35 | 3.50 |
| 566 | Linoleic acid | (d) NH₂CH(CH₃)-C₆H₄-Cl | cyclohexyl | Chloroform | 12 | 221–227/ 0.08 | 74.69 | 74.83 | 9.65 | 9.90 | 3.35 | 3.25 |
| 567 | Linoleic acid | NH₂CH(CH₃)-C₆H₄-OCH₃ | cyclohexyl | Benzene | 5 | 220–225/ 0.09 | 78.40 | 78.09 | 10.48 | 10.31 | 3.39 | 3.28 |

-continued

| Ex. No. | Acid | Amine | B BN=C=NB | Solvent | Reaction time (h) | b.p. °C./ mmHg | C % Theoretical | C % Analytical | H % Theoretical | H % Analytical | N % Theoretical | N % Analytical |
|---|---|---|---|---|---|---|---|---|---|---|---|---|
| 568 | Linoleic acid | NH₂CH(CH₃)-C₆H₄-OCH₃ (o) | cyclohexyl | Toluene | 12 | 218–223/ 0.09 | 78.40 | 78.08 | 10.48 | 10.35 | 3.39 | 3.29 |
| 569 | Linoleic acid | NH₂CH(CH₃)-C₆H₄-OCH₃ (p) | cyclohexyl | Toluene | 12 | 220–225/ 0.1 | 78.40 | 78.07 | 10.48 | 10.31 | 3.39 | 3.26 |
| 570 | Oleic acid | NH₂CH(CH₃)-C₆H₄-C₂H₅ | cyclohexyl | Benzene | 6 | 212–222/ 0.08 | 81.29 | 81.41 | 11.45 | 11.44 | 3.39 | 3.51 |
| 571 | Oleic acid | NH₂CH(C₂H₅)-C₆H₄-C₂H₅ | cyclohexyl | Benzene | 3 | 213–223/ 0.09 | 81.44 | 81.65 | 11.55 | 11.69 | 3.28 | 3.50 |
| 572 | Oleic acid | NH₂CH(CH₃)-C₆H₄-Br | cyclohexyl | Toluene | 6 | 226/231/ 0.09 | 67.24 | 67.44 | 9.05 | 8.85 | 3.01 | 3.39 |
| 573 | Isostearic acid | NH₂CH(CH₃)-C₆H₄-CH₃ | cyclohexyl | Toluene | 8 | 200–217/ 0.08 | 80.73 | 80.91 | 11.83 | 12.03 | 3.49 | 3.62 |
| 574 | Isostearic acid | NH₂CH(C₂H₅)-C₆H₄-C(CH₃)₃ | cyclohexyl | Ether | 10 | 209–231/ 0.1 | 81.33 | 81.52 | 12.11 | 12.32 | 3.06 | 3.28 |
| 575 | Isostearic acid | NH₂CH(CH₃)-C₆H₄-Cl | cyclohexyl | Dioxane | 10 | 221–228/ 0.09 | 74.02 | 74.33 | 10.43 | 10.66 | 3.32 | 3.61 |
| 576 | Isostearic acid | NH₂CH(CH₃)-C₆H₄-Br | cyclohexyl | Ether | 6 | 223–241/ 0.1 | 66.95 | 67.06 | 9.44 | 9.58 | 3.00 | 3.21 |
| 577 | Isostearic acid | NH₂CH(CH₃)-C₆H₄-OCH₃ | phenyl | Dioxane | 12 | 221–226/ 0.05 | 77.64 | 77.74 | 11.34 | 11.65 | 3.35 | 3.15 |
| 578 | Isostearic acid | NH₂CH(C₂H₅)-C₆H₄-OC₂H₅ | cyclohexyl | Cyclohexane | 12 | 222–231/ 0.09 | 78.14 | 78.32 | 11.53 | 11.58 | 3.14 | 3.08 |
| 579 | Linolenic acid | NH₂CH(CH₃)-C₆H₄-OC₂H₅ (o) | cyclohexyl | Ether | 12 | 220–239/ 0.08 | 79.61 | 79.93 | 10.18 | 10.31 | 3.29 | 3.31 |
| 580 | Linolenic acid | NH₂CH(C₂H₅)-C₆H₄-OCH₃ | cyclohexyl | Tetrahydrofuran | 18 | 218–238/ 0.1 | 79.61 | 79.78 | 10.18 | 10.32 | 3.29 | 3.40 |
| 581 | Linolenic acid | NH₂CH(CH₃)-C₆H₄-CH₃ | cyclohexyl | Benzene | 6 | 221–240/ 0.09 | 81.97 | 82.06 | 10.45 | 10.65 | 3.54 | 3.28 |
| 582 | Linolenic acid | NH₂CH(CH₃)-C₆H₄-Cl (o) | cyclohexyl | Benzene | 10 | 219–239/ 0.2 | 75.09 | 75.19 | 9.14 | 10.09 | 3.36 | 3.67 |

-continued

| Ex. No. | Acid | Amine | B BN=C=NB | Solvent | Reaction time (h) | b.p. °C./ mmHg | C % Theoretical | C % Analytical | H % Theoretical | H % Analytical | N % Theoretical | N % Analytical |
|---|---|---|---|---|---|---|---|---|---|---|---|---|
| 583 | Linseed oil acid | NH$_2$CH(CH$_3$)—C$_6$H$_4$—CH$_3$ | cyclohexyl | Benzene | 10 | 199–219/ 0.09 | | | | | | |
| 584 | Linseed oil acid | NH$_2$CH(CH$_3$)—C$_6$H$_4$—Cl | cyclohexyl | Benzene | 10 | 220–230/ 0.08 | | | | | | |
| 585 | Safflower oil acid | NH$_2$CH(CH$_3$)—C$_6$H$_4$—CH$_3$ | cyclohexyl | Benzene | 5 | 203–209/ 0.06 | | | | | | |
| 586 | Safflower oil acid | NH$_2$CH(C$_2$H$_5$)—C$_6$H$_4$—CH$_3$ | cyclohexyl | Benzene | 10 | 203–211/ 0.06 | | | | | | |
| 587 | Safflower oil acid | NH$_2$CH(CH$_3$)—C$_6$H$_4$—OC$_2$H$_5$ | cyclohexyl | Ether | 10 | 219–228/ 0.06 | | | | | | |
| 588 | Safflower oil acid | NH$_2$CH(C$_2$H$_5$)—C$_6$H$_4$—Br | cyclohexyl | Ether | 4 | 220–226/ 0.1 | | | | | | |
| 589 | Soybean oil acid | NH$_2$CH(C$_3$H$_7$)—C$_6$H$_4$—C$_3$H$_7$ | cyclohexyl | Ether | 4 | 219–237/ 0.06 | | | | | | |
| 590 | Sunflower oil acid | NH$_2$CH(C$_3$H$_7$)—C$_6$H$_4$—OC$_4$H$_9$ | cyclohexyl | Toluene | 4 | 222–241/ 0.05 | | | | | | |
| 591 | Castor oil acid | NH$_2$CH(CH$_3$)—C$_6$H$_3$(Cl)(Cl) | cyclohexyl | Benzene | 5 | 218–228/ 0.01 | | | | | | |
| 592 | Rape seed oil | NH$_2$CH(CH$_3$)—C$_6$H$_4$—OC$_2$H$_5$ | cyclohexyl | Toluene | 8 | 221–228/ 0.04 | | | | | | |
| 593 | Cottonseed oil acid | NH$_2$CH(C$_3$H$_7$)—C$_6$H$_4$—OCH$_3$ | cyclohexyl | Ether | 10 | 223–231/ 0.05 | | | | | | |
| 594 | Olive oil acid | NH$_2$CH(CH$_3$)—C$_6$H$_4$—C$_2$H$_5$ | cyclohexyl | Benzene | 10 | 214–229/ 0.05 | | | | | | |
| 595 | Peanut oil acid | NH$_2$CH(l)(CH$_3$)—C$_6$H$_4$—OCH$_3$ | cyclohexyl | Benzene | 12 | 220–227/ 0.06 | | | | | | |
| 596 | Locust oil acid | NH$_2$CH(d)(CH$_3$)—C$_6$H$_4$—OCH$_3$ | cyclohexyl | Dioxane | 12 | 223–227/ 0.06 | | | | | | |
| 597 | Chrysalis oil acid | NH$_2$CH(C$_2$H$_5$)—C$_6$H$_3$(CH$_3$)(Cl) | cyclohexyl | Chloroform | 18 | 233–242/ 0.05 | | | | | | |

-continued

| Ex. No. | Acid | Amine | B BN=C=NB | Solvent | Reaction time (h) | b.p. °C./ mmHg | C % Theoretical | C % Analytical | H % Theoretical | H % Analytical | N % Theoretical | N % Analytical |
|---|---|---|---|---|---|---|---|---|---|---|---|---|
| 598 | Shark oil acid | NH₂CH(CH₃)–C₆H₃(OCH₃)(CH₃) | cyclohexyl | Toluene | 10 | 225–241/ 0.05 | | | | | | |
| 599 | Sardine oil acid | NH₂CH(CH₃)–C₆H₄–C₂H₅ | cyclohexyl | Tetrahydrofuran | 5 | 218–232/ 0.05 | | | | | | |
| 600 | Mackerel oil acid | NH₂CH(CH₃)–C₆H₄–Br | cyclohexyl | Dioxane | 18 | 221–227/ 0.06 | | | | | | |
| 601 | Herring oil acid | NH₂CH(CH₃)–C₆H₄–CH₃ | phenyl | Acetone | 5 | 193–223/ 0.07 | | | | | | |
| 602 | Saurel oil acid | NH₂CH(CH₃)–C₆H₄–C₄H₉ | cyclohexyl | Ether | 10 | 202–231/ 0.06 | | | | | | |
| 603 | Cod oil acid | NH₂CH(C₄H₉)–C₆H₄–CH₃ | cyclohexyl | Benzene | 20 | 199–227/ 0.05 | | | | | | |
| 604 | Gray mullet oil acid | NH₂CH(CH₃)–C₆H₄–OCH₃ | cyclohexyl | Acetone | 5 | 194–237/ 0.06 | | | | | | |
| 605 | Menhaden oil acid | NH₂CH(CH₃)–C₆H₄(OCH₃) | cyclohexyl | Ether | 5 | 181–241/ 0.06 | | | | | | |
| 606 | Flatfish oil acid | NH₂CH(C₂H₅)–C₆H₄–Cl | cyclohexyl | Toluene | 18 | 186–241/ 0.08 | | | | | | |
| 607 | Residual oil acid | NH₂CH(CH₃)–C₆H₄–OC₂H₅ | cyclohexyl | Benzene | 4 | 201–235/ 0.06 | | | | | | |

EXAMPLE 608

A mixture of 28 g. of linoleic acid and 14 g. of α,p-dimethylbenzylamine, was heated at 180° C. for 20 hours. After separating water the reaction mixture was distilled to obtain 33.3 g. of a desired product, b.p. 119°–219° C./0.05 mmHg. Elementary analysis:

| | Theoretical | Analytical |
|---|---|---|
| C (%) | 81.55 | 81.77 |
| H (%) | 10.90 | 11.04 |
| N (%) | 3.52 | 3.49 |

Examples 609–663 are shown in the following table:

| Ex. No. | Acid Moiety | Amine Moiety | Reaction temperature (° C.) | Reaction time (hr.) | b.p. ° C./mmHg | C % Theoretical | C % Analytical | H % Theoretical | H % Analytical | N % Theoretical | N % Analytical |
|---|---|---|---|---|---|---|---|---|---|---|---|
| 609 | Linoleic acid | NH₂CH(CH₃)–C₆H₄–CH₃ | 200 | 12 | 202–219/0.05 | 81.55 | 81.61 | 10.90 | 11.02 | 3.52 | 3.48 |

-continued

| Ex. No. | Acid Moiety | Amine Moiety | Reaction temperature (° C.) | Reaction time (hr.) | b.p. ° C./mmHg | C % Theoretical | C % Analytical | H % Theoretical | H % Analytical | N % Theoretical | N % Analytical |
|---|---|---|---|---|---|---|---|---|---|---|---|
| 610 | Linoleic acid | 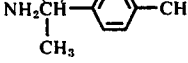 | 200 | 12 | 208–220/0.05 | 81.55 | 81.63 | 10.90 | 11.03 | 3.52 | 3.48 |
| 611 | Linoleic acid | 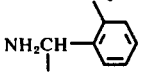 | 180 | 12 | 197–209/0.03 | 81.69 | 81.79 | 11.02 | 11.05 | 3.40 | 3.31 |
| 612 | Linoleic acid | 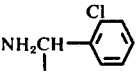 | 180 | 20 | 220–223/0.07 | 74.69 | 74.81 | 9.65 | 9.88 | 3.33 | 3.27 |
| 613 | Linoleic acid | 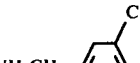 | 180 | 24 | 222–225/0.05 | 74.69 | 74.83 | 9.65 | 9.89 | 3.35 | 3.19 |
| 614 | Linoleic acid | 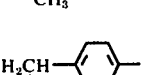 | 175 | 21 | 219–224/0.05 | 74.69 | 74.84 | 9.65 | 9.84 | 3.35 | 3.28 |
| 615 | Linoleic acidi | 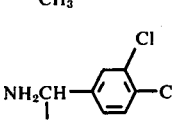 | 200 | 20 | 223–241/0.08 | 69.01 | 69.23 | 8.69 | 8.74 | 3.10 | 3.30 |
| 616 | Linoleic acid | 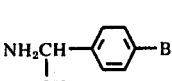 | 175 | 21 | 225–240/0.2 | 67.52 | 67.77 | 8.72 | 8.79 | 3.03 | 3.45 |
| 617 | Linoleic acid | 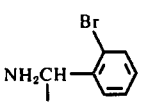 | 200 | 12 | 222–238/0.1 | 67.52 | 67.71 | 8.72 | 8.83 | 3.03 | 3.40 |
| 618 | Linoleic acid | 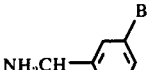 | 200 | 12 | 220–237/0.09 | 67.52 | 67.74 | 8.72 | 8.85 | 3.03 | 3.21 |
| 619 | Linoleic acid | 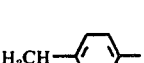 | 175 | 21 | 222–234/0.08 | 68.06 | 68.31 | 8.82 | 8.90 | 2.94 | 3.08 |
| 620 | Linoleic acid | 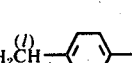 | 180 | 12 | 208–224/0.05 | 81.55 | 81.69 | 10.90 | 10.98 | 3.52 | 3.72 |
| 621 | Linoleic acid | 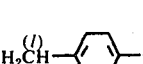 | 175 | 12 | 220–225/0.06 | 74.69 | 74.81 | 9.65 | 9.92 | 3.35 | 3.45 |
| 622 | Linoleic acid | 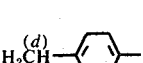 | 180 | 12 | 221–225/0.08 | 74.69 | 74.83 | 9.65 | 9.90 | 3.35 | 3.61 |
| 623 | Linoleic acid | 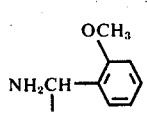 | 175 | 21 | 220–224/0.08 | 78.40 | 78.85 | 10.48 | 10.63 | 3.39 | 3.29 |

-continued

| Ex. No. | Acid Moiety | Amine Moiety | Reaction temperature (°C.) | Reaction time (hr.) | b.p. °C./mmHg | C % Theoretical | C % Analytical | H % Theoretical | H % Analytical | N % Theoretical | N % Analytical |
|---|---|---|---|---|---|---|---|---|---|---|---|
| 624 | Linoleic acid | 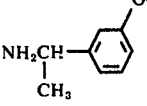 | 180 | 18 | 218–230/0.1 | 78.40 | 78.59 | 10.48 | 10.61 | 3.39 | 3.71 |
| 625 | Linoleic acid | 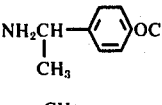 | 180 | 13 | 218–223/0.09 | 78.40 | 78.58 | 10.48 | 10.61 | 3.39 | 3.48 |
| 626 | Oleic acid | 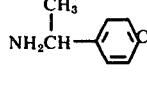 | 200 | 12 | 208–220/0.08 | 81.29 | 81.41 | 11.45 | 11.35 | 3.39 | 3.09 |
| 627 | Oleic acid | 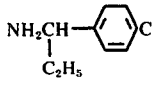 | 200 | 12 | 210–225/0.09 | 81.44 | 81.62 | 11.55 | 11.36 | 3.28 | 3.19 |
| 628 | Oleic acid | 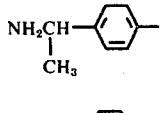 | 175 | 20 | 224–232/0.09 | 67.24 | 67.41 | 9.05 | 9.15 | 3.01 | 3.12 |
| 629 | Isostearic acid | 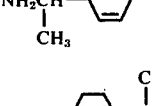 | 175 | 18 | 200–215/0.08 | 80.73 | 80.90 | 11.83 | 11.94 | 3.49 | 3.29 |
| 630 | Isostearic acid | 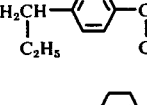 | 180 | 18 | 209–230/0.09 | 81.33 | 81.47 | 12.11 | 12.22 | 3.06 | 3.15 |
| 631 | Isostearic acid | 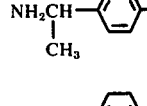 | 175 | 18 | 221–228/0.08 | 74.02 | 74.33 | 10.43 | 10.33 | 3.32 | 3.46 |
| 632 | Isostearic acid | 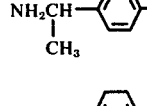 | 200 | 12 | 222–243/0.09 | 66.95 | 67.06 | 9.44 | 9.60 | 3.00 | 3.06 |
| 633 | Isostearic acid | 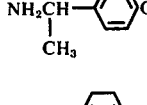 | 175 | 18 | 222–226/0.05 | 77.64 | 77.84 | 11.34 | 11.58 | 3.35 | 3.39 |
| 634 | Isostearic acid | 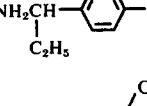 | 175 | 18 | 222–233/0.09 | 78.14 | 78.20 | 11.53 | 11.51 | 3.14 | 3.33 |
| 635 | Linolenic acid | 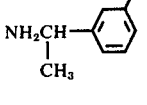 | 175 | 18 | 218–241/0.08 | 79.61 | 79.60 | 10.18 | 10.36 | 3.29 | 3.45 |
| 636 | Linolenic acid | 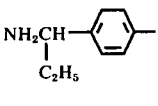 | 180 | 18 | 216–237/0.1 | 79.61 | 79.49 | 10.18 | 10.37 | 3.29 | 3.45 |
| 637 | Linolenic acid | 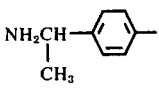 | 175 | 21 | 218–241/0.09 | 81.97 | 82.08 | 10.45 | 10.59 | 3.54 | 3.68 |
| 638 | Linolenic acid | 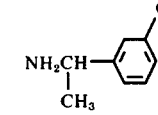 | 150 | 23 | 212–222/0.08 | 75.09 | 84.98 | 9.14 | 9.34 | 3.36 | 3.47 |

-continued

| Ex. No. | Acid Moiety | Amine Moiety | Reaction temperature (° C.) | Reaction time (hr.) | b.p. °C./mmHg | C % Theoretical | C % Analytical | H % Theoretical | H % Analytical | N % Theoretical | N % Analytical |
|---|---|---|---|---|---|---|---|---|---|---|---|
| 639 | Linseed oil acid | 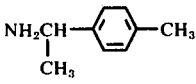 | 220 | 12 | 198–228/0.08 | | | | | | |
| 640 | Linseed oil acid | 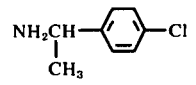 | 150 | 24 | 203–209/0.06 | | | | | | |
| 641 | Safflower oil acid | 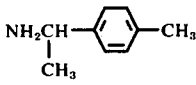 | 150 | 24 | 203–215/0.07 | | | | | | |
| 642 | Safflower oil acid | 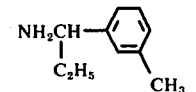 | 175 | 18 | 219–228/0.06 | | | | | | |
| 643 | Safflower oil acid | 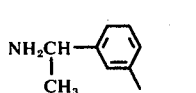 | 200 | 12 | 218–224/0.05 | | | | | | |
| 644 | Safflower oil acid | 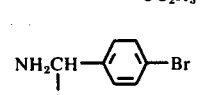 | 150 | 18 | 220–225/0.1 | | | | | | |
| 645 | Soybean oil acid | 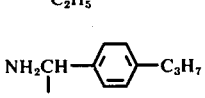 | 200 | 12 | 218–234/0.05 | | | | | | |
| 646 | Sunflower oil acid | 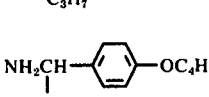 | 170 | 18 | 218–225/0.05 | | | | | | |
| 647 | Castor oil acid | 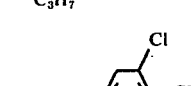 | 170 | 18 | 218–225/0.05 | | | | | | |
| 648 | Rapeseed oil acid | 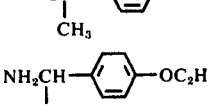 | 200 | 20 | 220–228/0.06 | | | | | | |
| 649 | Cottonseed oil acid | 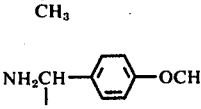 | 175 | 18 | 223–231/0.05 | | | | | | |
| 650 | Olive oil acid | 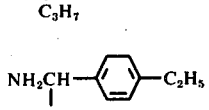 | 150 | 12 | 214–229/0.05 | | | | | | |
| 651 | Peanut oil acid | 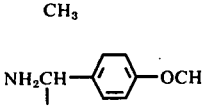 | 175 | 12 | 220–226/0.06 | | | | | | |
| 652 | Locust oil acid | 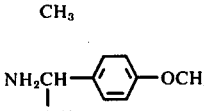 | 200 | 12 | 218–229/0.05 | | | | | | |
| 653 | Chrysalis oil acid | 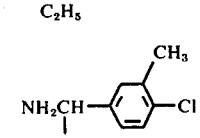 | 180 | 12 | 233–242/0.05 | | | | | | |

-continued

| Ex. No. | Acid Moiety | Amine Moiety | Reaction temperature (° C.) | Reaction time (hr.) | b.p. ° C./mmHg | C % Theoretical | C % Analytical | H % Theoretical | H % Analytical | N % Theoretical | N % Analytical |
|---|---|---|---|---|---|---|---|---|---|---|---|
| 654 | Shark oil acid | NH₂CH(CH₃)-C₆H₃(OCH₃)(CH₃) | 180 | 21 | 225–243/0.05 | | | | | | |
| 655 | Sardine oil acid | NH₂CH(CH₃)-C₆H₄-OC₂H₅ | 175 | 20 | 209–228/0.05 | | | | | | |
| 656 | Mackerel oil acid | NH₂CH(CH₃)-C₆H₄-Br | 175 | 20 | 218–224/0.05 | | | | | | |
| 657 | Herring oil acid | NH₂CH(CH₃)-C₆H₄-CH₃ | 200 | 18 | 194–218/0.06 | | | | | | |
| 658 | Saurel oil acid | NH₂CH(CH₃)-C₆H₄-C₄H₉ | 180 | 18 | 197–230/0.06 | | | | | | |
| 659 | Cod oil acid | NH₂CH(C₄H₉)-C₆H₄-CH₃ | 175 | 18 | 198–219/0.05 | | | | | | |
| 660 | Gray mullet oil acid | NH₂CH(CH₃)-C₆H₄-OCH₃ | 175 | 18 | 193–240/0.07 | | | | | | |
| 661 | Menhaden oil acid | NH₂CH(CH₃)-C₆H₄(OCH₃) | 180 | 18 | 183–239/0.06 | | | | | | |
| 662 | Flatfish oil acid | NH₂CH(C₂H₅)-C₆H₄-Cl | 175 | 18 | 194–237/0.08 | | | | | | |
| 663 | Residual oil acid | NH₂CH(CH₃)-C₆H₄-OC₂H₅ | 200 | 18 | 201–230/0.06 | | | | | | |

EXAMPLE 664

To a mixture of 13.5 g. of α,p-dimethylbenzylamine, 7 g. of trimethylamine and 100 ml. of anhydrous ether was added a solution of 29.9 g. of linoleic acid chloride in 50 ml. of anhydrous ether under cooling and stirring at 0° – 5° C. After addition, the reaction mixture was boiled for 2 hours and the ether solution was washed with acid, alkoli and water, and was then dried, concentrated and distilled to obtain 38 g. of a desired product. Elementary analysis:

|  | Theoretical | Analytical |
|---|---|---|
| C (%) | 81.55 | 81.69 |
| H (%) | 10.90 | 11.12 |
| N (%) | 3.52 | 3.44 |

Examples 665–719 are shown in the following table, in which:

Solvent:
a. Ether
b. Dioxane
c. Tetrahydrofuran
d. Acetone
e. Methylisobutylketone
f. Benzene
g. Toluene
h. Chloroform
i. Dimethylformamide
k. Water

| Ex. | Acid Moiety | Amine Moiety | Condensing agent | Solvent | b.p. °C/mmHg | C % Theoretical | C % Analytical | H % Theoretical | H % Analytical | N % Theoretical | N % Analytical |
|---|---|---|---|---|---|---|---|---|---|---|---|
| 665 | Linoleic acid chloride | NH$_2$CH(CH$_3$)-C$_6$H$_4$-CH$_3$ (m) | K$_2$CO$_3$ | d | 200–216/0.02 | 81.55 | 81.67 | 10.90 | 10.99 | 3.52 | 3.40 |
| 666 | Linoleic acid chloride | (d) NH$_2$CH(CH$_3$)-C$_6$H$_4$-CH$_3$ | NaOH | k,d | 208–221/0.05 | 81.55 | 81.71 | 10.90 | 11.13 | 3.52 | 3.42 |
| 667 | Linoleic acid chloride | NH$_2$CH(C$_2$H$_5$)-C$_6$H$_4$-CH$_3$ | K$_2$CO$_3$ | d | 200–209/0.03 | 81.69 | 81.90 | 11.02 | 11.25 | 3.40 | 3.19 |
| 668 | Linoleic acid chloride | NH$_2$CH(CH$_3$)-C$_6$H$_4$-Cl (o) | Na$_2$CO$_3$ | e | 215–221/0.06 | 74.69 | 74.82 | 9.65 | 9.83 | 3.35 | 3.09 |
| 669 | Linoleic acid chloride | NH$_2$CH(CH$_3$)-C$_6$H$_4$-Cl (m) | N(CH$_3$)$_3$ | a | 220–228/0.05 | 74.69 | 74.85 | 9.65 | 9.84 | 3.35 | 3.12 |
| 670 | Linoleic acid chloride | NH$_2$CH(CH$_3$)-C$_6$H$_4$-Cl (p) | N(C$_2$H$_5$)$_3$ | a | 216–223/0.06 | 74.69 | 74.84 | 9.65 | 9.87 | 3.35 | 3.11 |
| 671 | Linoleic acid chloride | NH$_2$CH(CH$_3$)-C$_6$H$_3$-Cl$_2$ | NaOH | k,b | 218–239/0.06 | 69.01 | 69.22 | 8.69 | 8.81 | 3.10 | 2.94 |
| 672 | Linoleic acid chloride | NH$_2$CH(CH$_3$)-C$_6$H$_4$-Br | NaOH | d | 221–236/0.08 | 67.52 | 67.78 | 8.72 | 8.90 | 3.03 | 2.90 |
| 673 | Linoleic acid chloride | NH$_2$CH(CH$_3$)-C$_6$H$_4$-Br (o) | (CH$_3$)$_2$N-C$_6$H$_5$ | f | 218–229/0.09 | 67.52 | 67.76 | 8.72 | 8.92 | 3.03 | 2.87 |
| 674 | Linoleic acid chloride | NH$_2$CH(CH$_3$)-C$_6$H$_4$-Br (m) | K$_2$CO$_3$ | d | 218–235/0.08 | 67.52 | 67.71 | 8.72 | 8.97 | 3.03 | 2.88 |
| 675 | Linoleic acid chloride | NH$_2$CH(C$_2$H$_5$)-C$_6$H$_4$-Br | (C$_2$H$_5$)$_2$N-C$_6$H$_5$ | f | 216–233/0.07 | 68.06 | 68.31 | 8.82 | 8.99 | 2.94 | 2.67 |
| 676 | Linoleic acid chloride | (l) NH$_2$CH(CH$_3$)-C$_6$H$_4$-CH$_3$ | NaOH | k,c | 208–222/0.05 | 81.55 | 81.70 | 10.90 | 11.05 | 3.52 | 3.42 |
| 677 | Linoleic acid chloride | (l) NH$_2$CH(CH$_3$)-C$_6$H$_4$-Cl | K$_2$CO$_3$ | e | 218–223/0.06 | 74.69 | 74.75 | 9.65 | 9.78 | 3.55 | 3.02 |
| 678 | Linoleic acid chloride | (d) NH$_2$CH(CH$_3$)-C$_6$H$_4$-Cl | NaOH | k,b | 217–227/0.05 | 74.69 | 74.82 | 9.65 | 9.92 | 3.35 | 3.11 |

-continued

| Ex. | Acid Moiety | Amine Moiety | Condensing agent | Solvent | b.p. °C/mmHg | C % Theoretical | C % Analytical | H % Theoretical | H % Analytical | N % Theoretical | N % Analytical |
|---|---|---|---|---|---|---|---|---|---|---|---|
| 679 | Linoleic acid chloride | 2-OCH$_3$-C$_6$H$_4$-CH(CH$_3$)-NH$_2$ | pyridine | e | 219–229/0.05 | 78.40 | 78.70 | 10.48 | 10.72 | 3.39 | 3.18 |
| 680 | Linoleic acid chloride | 3-OCH$_3$-C$_6$H$_4$-CH(CH$_3$)-NH$_2$ | 2-methylpyridine | e | 218–232/0.08 | 78.40 | 78.62 | 10.48 | 10.74 | 3.39 | 3.29 |
| 681 | Linoleic acid chloride | 4-OCH$_3$-C$_6$H$_4$-CH(CH$_3$)-NH$_2$ | NaOH | k,i | 216–229/0.07 | 78.40 | 78.62 | 10.48 | 10.69 | 3.39 | 3.19 |
| 682 | Oleic acid | 4-C$_2$H$_5$-C$_6$H$_4$-CH(CH$_3$)-NH$_2$ | NaOH | k,b | 206–221/0.06 | 81.29 | 81.42 | 11.45 | 11.65 | 3.39 | 3.19 |
| 683 | Oleic acid chloride | 4-C$_2$H$_5$-C$_6$H$_4$-CH(C$_2$H$_5$)-NH$_2$ | NaOH | k,b | 208–225/0.08 | 81.44 | 81.51 | 11.55 | 11.62 | 3.28 | 3.08 |
| 684 | Oleic acid chloride | 4-Br-C$_6$H$_4$-CH(CH$_3$)-NH$_2$ | K$_2$CO$_3$ | d | 223–235/0.06 | 67.24 | 67.39 | 9.05 | 9.23 | 3.01 | 2.89 |
| 685 | Isostearic acid chloride | 4-CH$_3$-C$_6$H$_4$-CH(CH$_3$)-NH$_2$ | NaOH | k,d | 200–215/0.08 | 80.73 | 80.88 | 11.83 | 11.96 | 3.49 | 3.29 |
| 686 | Isostearic acid chloride | 4-C(CH$_3$)$_3$-C$_6$H$_4$-CH(C$_2$H$_5$)-NH$_2$ | N(CH$_3$)$_3$ | f | 209–230/0.08 | 81.33 | 81.42 | 12.11 | 12.35 | 3.06 | 2.94 |
| 687 | Isostearic acid chloride | 4-Cl-C$_6$H$_4$-CH(CH$_3$)-NH$_2$ | N(CH$_3$)$_3$ | f | 220–227/0.05 | 74.02 | 74.22 | 10.43 | 10.65 | 3.32 | 3.16 |
| 688 | Isostearic acid chloride | 4-Br-C$_6$H$_4$-CH(CH$_3$)-NH$_2$ | N(CH$_3$)$_3$ | a | 218–242/0.07 | 66.95 | 66.99 | 9.44 | 9.61 | 3.00 | 2.93 |
| 689 | Isostearic acid chloride | 4-OCH$_3$-C$_6$H$_4$-CH(CH$_3$)-NH$_2$ | NaOH | k,d | 217–227/0.05 | 77.64 | 77.81 | 11.34 | 11.51 | 3.35 | 3.16 |
| 690 | Isostearic acid chloride | 4-OC$_2$H$_5$-C$_6$H$_4$-CH(C$_2$H$_5$)-NH$_2$ | N(CH$_3$)$_3$ | a | 219–231/0.08 | 78.14 | 78.32 | 11.53 | 11.68 | 3.14 | 3.07 |
| 691 | Linolenic acid chloride | 4-OC$_2$H$_5$-C$_6$H$_4$-CH(CH$_3$)-NH$_2$ | N(CH$_3$)$_3$ | a | 218–240/0.07 | 79.61 | 79.79 | 10.18 | 10.31 | 3.29 | 3.08 |
| 692 | Linolenic acid chloride | 4-OCH$_3$-C$_6$H$_4$-CH(C$_2$H$_5$)-NH$_2$ | pyridine | d | 212–225/0.07 | 79.61 | 79.77 | 10.18 | 10.30 | 3.29 | 3.08 |

-continued

| Ex. | Acid Moiety | Amine Moiety | Condensing agent | Solvent | b.p. °C/mmHg | C % Theoretical | C % Analytical | H % Theoretical | H % Analytical | N % Theoretical | N % Analytical |
|---|---|---|---|---|---|---|---|---|---|---|---|
| 693 | Linolenic acid chloride | NH₂-CH(CH₃)-C₆H₄-CH₃ (p) | pyridine | a | 200–225/0.05 | 81.97 | 82.23 | 10.45 | 10.58 | 3.54 | 3.19 |
| 694 | Linolenic acid chloride | NH₂-CH(CH₃)-C₆H₄-Cl (m) | pyridine | e | 201–212/0.03 | 75.05 | 75.24 | 9.14 | 9.32 | 3.36 | 3.26 |
| 695 | Linseed oil acid chloride | NH₂-CH(CH₃)-C₆H₄-CH₃ | NaOH | a | 203–215/0.07 | | | | | | |
| 696 | Linseed oil acid chloride | NH₂-CH(CH₃)-C₆H₄-Cl | NaOH | k,b | 219–228/0.05 | | | | | | |
| 697 | Safflower oil acid chloride | NH₂-CH(CH₃)-C₆H₄-CH₃ | NaOH | k,i | 218–233/0.05 | | | | | | |
| 698 | Safflower oil acid chloride | NH₂-CH(C₂H₅)-C₆H₄-CH₃ | NaOH | k,b | 218–228/0.05 | | | | | | |
| 699 | Safflower oil acid chloride | NH₂-CH(CH₃)-C₆H₄-OC₂H₅ | K₂CO₃ | e | 218–226/0.05 | | | | | | |
| 700 | Safflower oil acid chloride | NH₂-CH(C₂H₅)-C₆H₄-Br | K₂CO₃ | e | 220–231/0.08 | | | | | | |
| 701 | Soybean oil acid chloride | NH₂-CH(C₃H₇)-C₆H₄-C₃H₇ | pyridine | f | 216–233/0.05 | | | | | | |
| 702 | Sunflower oil acid chloride | NH₂-CH(C₃H₇)-C₆H₄-OC₄H₉ | pyridine | f | 215–236/0.05 | | | | | | |
| 703 | Castor oil acid chloride | NH₂-CH(CH₃)-C₆H₃(Cl)(Cl) | NaOH | k,c | 214–226/0.05 | | | | | | |
| 704 | Rapeseed oil acid chloride | NH₂-CH(CH₃)-C₆H₄-OC₂H₅ | NaOH | k,b | 219–229/0.05 | | | | | | |
| 705 | Cottonseed oil acid chloride | NH₂-CH(C₃H₇)-C₆H₄-OCH₃ | K₂CO₃ | k,d | 223–234/0.05 | | | | | | |
| 706 | Olive oil acid chloride | NH₂-CH(CH₃)-C₆H₄-C₂H₅ | K₂CO₃ | d | 215–232/0.05 | | | | | | |

-continued

| Ex. | Acid Moiety | Amine Moiety | Condensing agent | Solvent | b.p. °C/mmHg | C % Theoretical | C % Analytical | H % Theoretical | H % Analytical | N % Theoretical | N % Analytical |
|---|---|---|---|---|---|---|---|---|---|---|---|
| 707 | Peanut oil acid chloride | NH₂CH(CH₃)–C₆H₄–OCH₃ | N(CH₃)₃ | g | 219–227/0.06 | | | | | | |
| 708 | Locust oil acid chloride | NH₂CH(C₂H₅)–C₆H₄–OCH₃ | N(CH₃)₃ | a | 218–227/0.06 | | | | | | |
| 709 | Chrysalis oil acid chloride | NH₂CH(C₂H₅)–C₆H₃(CH₃)(Cl) | pyridine | c | 233–245/0.06 | | | | | | |
| 710 | Shark oil acid chloride | NH₂CH(CH₃)–C₆H₃(OCH₃)(CH₃) | pyridine | i | 228–241/0.05 | | | | | | |
| 711 | Sardine oil acid chloride | NH₂CH(CH₃)–C₆H₄–OC₂H₅ | K₂CO₃ | d | 209–228/0.05 | | | | | | |
| 712 | Mackerel oil acid chloride | NH₂CH(CH₃)–C₆H₄–Br | KOH | k,b | 218–224/0.05 | | | | | | |
| 713 | Herring oil acid chloride | NH₂CH(CH₃)–C₆H₄–CH₃ | KOH | k,c | 194–219/0.05 | | | | | | |
| 714 | Saurel oil acid chloride | NH₂CH(CH₃)–C₆H₄–C₄H₉ | pyridine | h | 199–238/0.05 | | | | | | |
| 715 | Cod oil acid chloride | NH₂CH(C₄H₉)–C₆H₄–CH₃ | pyridine | g | 198–224/0.05 | | | | | | |
| 716 | Gray mullet oil acid chloride | NH₂CH(CH₃)–C₆H₄–OCH₃ | pyridine | f | 193–242/0.05 | | | | | | |
| 717 | Menhaden oil acid chloride | NH₂CH(CH₃)–C₆H₄–OCH₃ | K₂CO₃ | e | 183–239/0.05 | | | | | | |
| 718 | Flatfish oil acid chloride | NH₂CH(C₂H₅)–C₆H₄–Cl | K₂CO₃ | e | 199–235/0.05 | | | | | | |
| 719 | Residual oil acid chloride | NH₂CH(CH₃)–C₆H₄–OC₂H₅ | NaOH | d | 200–233/0.05 | | | | | | |

EXAMPLE 720

A mixture of 14.9 g. of methyl linoleate and 10 g. of α,p-dimethylbenzylamine was heated at 180° C. for 12 hours removing methanol during the reaction. After completion of the reaction, the reaction mixture was dissolved in 200 ml. of ether and was washed with 5% hydrochloric acid aqueous solution to recover about 2 g. of excess amine. The ether layer washed with water, dried and distilled to obtain 18.9 g. of a desired product. Elementary analysis:

|  | Theoretical | Analytical |
|---|---|---|
| C (%) | 81.55 | 81.58 |
| H (%) | 10.90 | 10.99 |
| N (%) | 3.52 | 3.49 |

Examples 721–800 are shown in the following table:

| Example | Ester or glyceride | RCOOA A | Amine Moiety | Catalyst | Reaction temperature °C | Reaction time (hr) | °C/mmHg. |
|---|---|---|---|---|---|---|---|
| 721 | Linoleic acid | CH₃ | 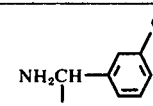 | NaOCH₃ | 150 | 4 | 200–215/0.02 |
| 722 | Linoleic acid | CH₃ | 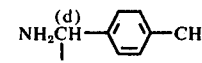 | — | 175 | 18 | 208–223/0.05 |
| 723 | Linoleic acid | CH₃ | 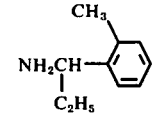 | — | 180 | 12 | 201–209/0.03 |
| 724 | Linoleic acid | CH₃ | 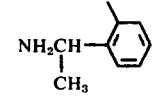 | — | 180 | 12 | 213–221/0.06 |
| 725 | Linoleic acid | C₂H₅ | 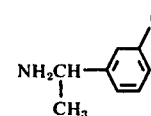 | — | 180 | 12 | 221–227/0.05 |
| 726 | Linoleic acid | CH₃ | 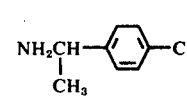 | — | 180 | 12 | 217–231/0.06 |
| 727 | Linoleic acid | CH₃ | 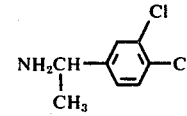 | — | 180 | 12 | 218–239/0.06 |
| 728 | Linoleic acid | CH₃ | 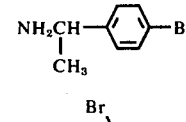 | — | 175 | 14 | 218–233/0.07 |
| 729 | Linoleic acid | CH₃ | 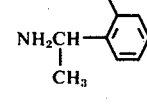 | — | 175 | 14 | 216–229/0.07 |
| 730 | Linoleic acid | CH₃ | 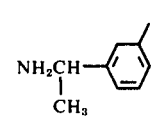 | — | 175 | 14 | 216–232/0.08 |
| 731 | Linoleic acid | CH₃ | 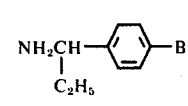 | — | 175 | 14 | 214–234/0.07 |

| | | | | | | | |
|---|---|---|---|---|---|---|---|
| 732 | Linoleic acid | $C_2H_5$ | $NH_2\overset{(l)}{\underset{CH_3}{C}H}$—⟨⟩—$CH_3$ | — | 175 | 14 | 205–224/0.05 |
| 733 | Linoleic acid | $CH_3$ | $NH_2\overset{(l)}{\underset{CH_3}{C}H}$—⟨⟩—Cl | — | 175 | 14 | 216–229/0.06 |
| 734 | Linoleic acid | $CH_3$ | $NH_2\overset{(d)}{\underset{CH_3}{C}H}$—⟨⟩—Cl | — | 175 | 14 | 215–227/0.05 |
| 735 | Linoleic acid | $CH_3$ | $NH_2\underset{CH_3}{C}H$—⟨⟩ with $OCH_3$ (ortho) | $NaOCH_3$ | 140 | 4 | 219–231/0.05 |
| 736 | Linoleic acid | $CH_3$ | $NH_2\underset{CH_3}{C}H$—⟨⟩ with $OCH_3$ (meta) | — | 175 | 12 | 217–232/0.08 |
| 737 | Linoleic acid | $CH_3$ | $NH_2\underset{CH_3}{C}H$—⟨⟩—$OCH_3$ | $KOCH_3$ | 150 | 4 | 216–229/0.07 |
| 738 | Oleic acid | $CH_3$ | $NH_2\underset{CH_3}{C}H$—⟨⟩—$C_2H_5$ | — | 145 | 21 | 205–221/0.06 |
| 739 | Oleic acid | $CH_3$ | $NH_2\underset{C_2H_5}{C}H$—⟨⟩—$C_2H_5$ | NaOEt | 135 | 4 | 207–222/0.07 |
| 740 | Oleic acid | $CH_3$ | $NH_2\underset{CH_3}{C}H$—⟨⟩—Br | — | 160 | 20 | 219–233/0.06 |
| 741 | Isostearic acid | $CH_3$ | $NH_2\underset{CH_3}{C}H$—⟨⟩—$CH_3$ | — | 165 | 18 | 199–221/0.07 |
| 742 | Isostearic acid | $CH_3$ | $NH_2\underset{C_2H_5}{C}H$—⟨⟩—$C(CH_3)_3$ | — | 175 | 18 | 205–230/0.07 |
| 743 | Isostearic acid | $CH_3$ | $NH_2\underset{CH_3}{C}H$—⟨⟩—Cl | — | 175 | 16 | 230–234/0.05 |
| 744 | Isostearic acid | $CH_3$ | $NH_2\underset{CH_3}{C}H$—⟨⟩—Br | — | 175 | 16 | 218–238/0.05 |
| 745 | Isostearic acid | $CH_3$ | $NH_2\underset{CH_3}{C}H$—⟨⟩—$OCH_3$ | — | 175 | 16 | 217–228/0.05 |
| 746 | Isostearic acid | $C_2H_5$ | $NH_2\underset{C_2H_5}{C}H$—⟨⟩—$OC_2H_5$ | — | 175 | 16 | 219–233/0.06 |
| 747 | Linolenic acid | $CH_3$ | $NH_2\underset{CH_3}{C}H$—⟨⟩ with $OC_2H_5$ (meta) | — | 180 | 16 | 218–238/0.06 |

| | | | | | | | |
|---|---|---|---|---|---|---|---|
| 748 | Linolenic acid | CH₃ | 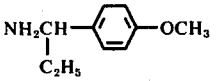 | — | 180 | 16 | 210–225/0.06 |
| 749 | Linolenic acid | CH₃ | 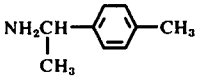 | — | 180 | 16 | 202–222/0.05 |
| 750 | Linolenic acid | CH₃ | 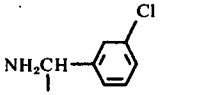 | — | 160 | 21 | 200–212/0.03 |
| 751 | Linseed oil acid | CH₃ | 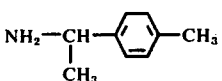 | — | 155 | 21 | 203–216/0.06 |
| 752 | Linseed oil acid | CH₃ | 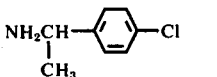 | — | 160 | 20 | 218–232/0.05 |
| 753 | Safflower oil acid | CH₃ | 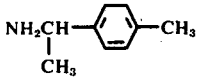 | — | 160 | 20 | 218–241/0.05 |
| 754 | Safflower oil acid | CH₃ | 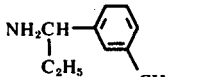 | — | 160 | 18 | 215–229/0.05 |
| 755 | Safflower oils acid | CH₃ | 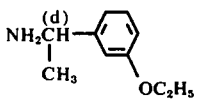 | — | 160 | 18 | 215–230/0.05 |
| 756 | Safflower oil acid | CH₃ | 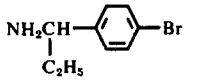 | — | 160 | 18 | 220–241/0.05 |
| 757 | Soybean oil acid | CH₃ | 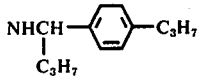 | — | 175 | 18 | 215–231/0.05 |
| 758 | Sunflower oil acid | CH₃ | 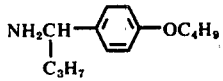 | — | 180 | 12 | 209–233/0.05 |
| 759 | Castor oil acid | CH₃ | 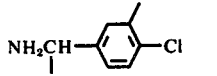 | — | 180 | 14 | 212–228/0.05 |
| 760 | Rape-seed oil acid | CH₃ | 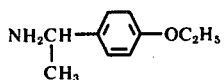 | KOtBu | 145 | 4 | 213–228/0.05 |
| 761 | Cottonseed oil acid | CH₃ | 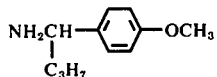 | — | 180 | 12 | 220–234/0.05 |
| 762 | Olive oil acid | CH₃ | 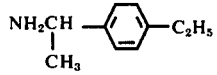 | — | 180 | 12 | 215–236/0.05 |
| 763 | Peanut oil acid | CH₃ | 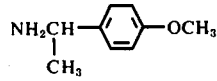 | — | 180 | 12 | 219–229/0.03 |

| | | | | | | | |
|---|---|---|---|---|---|---|---|
| 764 | Locust oil acid | CH₃ | 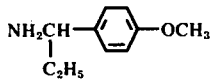 | — | 180 | 12 | 219–231/0.06 |
| 765 | Chrysalis oil acid | CH₃ | 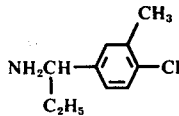 | — | 175 | 14 | 229–245/0.06 |
| 766 | Shark oil acid | CH₃ | 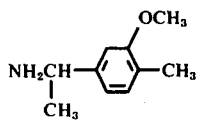 | — | 180 | 12 | 228–241/0.05 |
| 767 | Sardine oil acid | CH₃ | 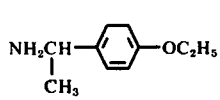 | — | 175 | 14 | 209–231/0.05 |
| 768 | Mackerel oil acid | CH₃ | 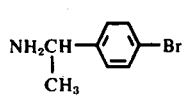 | — | 180 | 12 | 216–227/0.05 |
| 769 | Herring oil acid | CH₃ | 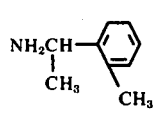 | NaOEt | 135 | 5 | 194–219/0.05 |
| 770 | Saurel oil acid | CH₃ | 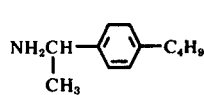 | — | 200 | 10 | 201–241/0.05 |
| 771 | Cod oil acid | CH₃ | 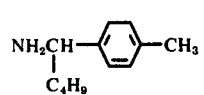 | — | 210 | 8 | 199–225/0.05 |
| 772 | Gray mullet oil acid | CH₃ | 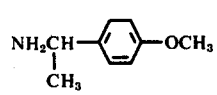 | — | 165 | 16 | 195–240/0.05 |
| 773 | Menhaden oil acid | CH₃ | 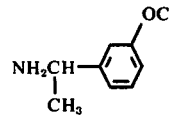 | — | 160 | 18 | 183–239/0.05 |
| 774 | Flatfish oil acid | CH₃ | 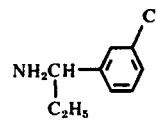 | — | 150 | 18 | 202–240/0.05 |
| 775 | Residual oil acid | CH₃ | 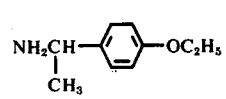 | — | 145 | 20 | 200–235/0.05 |
| 776 | Linseed oil | | 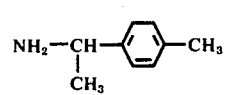 | — | 180 | 16 | 194–218/0.06 |
| 777 | Linseed oil | | 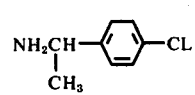 | — | 180 | 16 | 200–232/0.05 |
| 778 | Safflower oil | | 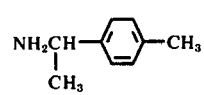 | NaOCH₃ | 140 | 4 | 199–239/0.04 |
| 779 | Safflower oil | | 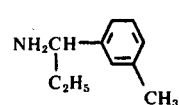 | H₃BO₄ | 145 | 10 | 202–231/0.05 |

| No. | Oil | Amine | Catalyst | Temp | Time | BP/Pressure |
|---|---|---|---|---|---|---|
| 780 | Safflower oil | NH₂CH(CH₃)–C₆H₄–OC₂H₅ | — | 175 | 10 | 200–240/0.05 |
| 781 | Safflower oil | NH₂CH(C₂H₅)–C₆H₄–Br | — | 175 | 12 | 203–235/0.05 |
| 782 | Soybean oil | NH₂CH(C₃H₇)–C₆H₄–C₃H₇ | — | 170 | 21 | 198–233/0.05 |
| 783 | Sunflower oil | NH₂CH(C₃H₇)–C₆H₄–OC₄H₉ | — | 175 | 21 | 199–235/0.05 |
| 784 | Castor oil | NH₂CH(CH₃)–C₆H₃(Cl)(Cl) | — | 175 | 21 | 202–239/0.05 |
| 785 | Rape-seed oil | NH₂CH(CH₃)–C₆H₄–OC₂H₅ | — | 175 | 22 | 200–228/0.05 |
| 786 | Cottonseed oil | NH₂CH(C₃H₇)–C₆H₄–OCH₃ | — | 175 | 23 | 208–235/0.05 |
| 787 | Olive oil | NH₂CH(CH₃)–C₆H₄–C₂H₅ | — | 175 | 21 | 200–236/0.04 |
| 788 | Peanut oil | NH₂CH(CH₃)–C₆H₄–OCH₃ | — | 180 | 22 | 200–234/0.05 |
| 789 | Locust oil | NH₂CH(C₂H₅)–C₆H₄–OCH₃ | — | 160 | 22 | 200–233/0.06 |
| 790 | Chrysalis oil | NH₂CH(C₂H₅)–C₆H₃(CH₃)(Cl) | — | 145 | 21 | 198–244/0.05 |
| 791 | Shark oil | NH₂CH(CH₃)–C₆H₃(CH₃)(CH₃) | — | 155 | 20 | 212–242/0.05 |
| 792 | Sardine oil | NH₂CH(CH₃)–C₆H₄–OC₂H₅ | H₃BO₄ | 150 | 4 | 200–233/0.05 |
| 793 | Mackerel oil | NH₂CH(CH₃)–C₆H₄–Br | — | 160 | 20 | 198–232/0.04 |
| 794 | Herring oil | NH₂CH(CH₃)–C₆H₄–CH₃ | NaOCH₃ | 150 | 4 | 190–220/0.05 |
| 795 | Saurel oil | NH₂CH(CH₃)–C₆H₄–C₄H₉ | — | 150 | 24 | 194–241/0.04 |

| | | | | | |
|---|---|---|---|---|---|
| 796 | Cod oil | 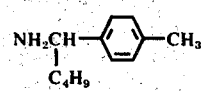 | — | 150 | 24 | 193–225/0.05 |
| 797 | Gray mullet oil | 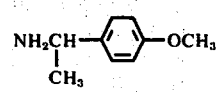 | — | 180 | 12 | 195–242/0.05 |
| 798 | Menhaden oil | 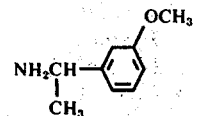 | — | 210 | 10 | 183–241/0.05 |
| 799 | Flatfish oil | 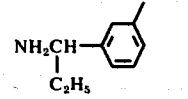 | — | 200 | 10 | 189–242/0.05 |
| 800 | Residual oil | 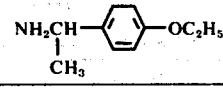 | — | 180 | 10 | 200–235/0.05 |
| Example | C % Theoretical | C % Analytical | H % Theoretical | H % Analytical | N % Theoretical | N % Analytical |
|---|---|---|---|---|---|---|
| 721 | 81.55 | 81.71 | 10.98 | 10.38 | 3.52 | 3.48 |
| 722 | 81.55 | 81.77 | 10.90 | 11.05 | 3.52 | 3.46 |
| 723 | 81.69 | 81.82 | 11.02 | 11.40 | 3.40 | 3.19 |
| 724 | 74.69 | 74.82 | 9.65 | 9.68 | 3.35 | 3.19 |
| 725 | 74.69 | 74.81 | 9.65 | 9.70 | 3.35 | 3.25 |
| 726 | 74.69 | 74.83 | 9.65 | 9.77 | 3.35 | 3.26 |
| 727 | 69.01 | 69.31 | 8.69 | 8.81 | 3.10 | 3.08 |
| 728 | 67.52 | 67.72 | 8.72 | 8.92 | 3.03 | 3.00 |
| 729 | 67.52 | 67.77 | 8.72 | 8.89 | 3.03 | 2.98 |
| 730 | 67.52 | 67.70 | 8.72 | 8.83 | 3.03 | 2.87 |
| 731 | 68.06 | 68.31 | 8.82 | 8.93 | 3.94 | 2.79 |
| 732 | 81.55 | 81.61 | 10.90 | 10.94 | 3.52 | 3.32 |
| 733 | 74.69 | 74.81 | 9.65 | 9.81 | 3.35 | 3.30 |
| 734 | 74.65 | 74.79 | 9.65 | 9.82 | 3.35 | 3.15 |
| 735 | 78.40 | 78.62 | 10.48 | 10.62 | 3.39 | 3.19 |
| 736 | 78.40 | 78.51 | 10.48 | 10.61 | 3.39 | 3.24 |
| 737 | 78.40 | 78.51 | 10.48 | 10.66 | 3.39 | 3.27 |
| 738 | 81.29 | 81.43 | 11.45 | 11.64 | 3.39 | 3.36 |
| 739 | 81.44 | 81.61 | 11.55 | 11.59 | 3.28 | 3.18 |
| 740 | 67.24 | 67.44 | 9.05 | 9.23 | 3.01 | 2.95 |
| 741 | 80.73 | 80.89 | 11.83 | 11.93 | 3.49 | 3.34 |
| 742 | 81.33 | 81.51 | 12.11 | 12.34 | 3.06 | 2.95 |
| 743 | 74.02 | 74.11 | 10.43 | 10.51 | 3.32 | 3.30 |
| 744 | 66.95 | 67.09 | 9.44 | 9.61 | 3.00 | 3.01 |
| 745 | 77.64 | 77.77 | 11.34 | 11.54 | 3.35 | 3.17 |
| 746 | 78.14 | 78.31 | 11.53 | 11.61 | 3.14 | 3.06 |
| 747 | 79.61 | 79.68 | 10.18 | 10.31 | 3.29 | 3.20 |
| 748 | 79.61 | 79.67 | 10.18 | 10.31 | 3.29 | 3.22 |
| 749 | 81.97 | 82.03 | 10.45 | 10.54 | 3.54 | 3.31 |
| 750 | 75.09 | 75.19 | 9.14 | 9.23 | 3.36 | 3.08 |

EXAMPLE 801

A solution of 14 g. of linoleic acid, 7 g. of α,p-dimethylbenzylamine and 0.5 g. of p-toluenesulfonic acid in 100 ml. of toluene, was refluxed for 8 hours using a water separator. The reaction mixture was washed with 5% NaOH aqueous solution, 5% HCl aqueous solution and water and was concentrated, and the residue was distilled to obtain 16.1 g. of a desired product, b.p. 203°–216° C./0.06 mmHg. Elementary analysis:

|  | Theoretical | Analytical |
|---|---|---|
| C (%) | 81.55 | 81.71 |
| H (%) | 10.90 | 10.99 |
| N (%) | 3.52 | 3.42 |

Examples 802–856 are shown in the following table, in which:

Condensing agent:
A. p-Toluenesulfonic acid.
B. p-Toluenesulfonic acid chloride.
C. Sulfuric acid.
D. Phenolsulfonic acid.
E. IRA-400.
F. Amberlist - 15.

Solvent:
a. Toluene.
b. Pyridine.
c. Benzene.
d. Chloroform.
e. Xylene.
f. Tetrachlorocarbon.

| Ex. | Acid | Amine | Agent | Solvent | Reaction time | b.p. °C/mmHg. | C % Theoretical | C % Analytical | H % Theoretical | H % Analytical | N % Theoretical | N % Analytical |
|---|---|---|---|---|---|---|---|---|---|---|---|---|
| 802 | Linoleic acid | [structure] | A | a | 8 | 199–214/0.05 | 81.55 | 81.67 | 10.90 | 11.11 | 3.52 | 3.46 |
| 803 | Lineoleic acid | [structure] | A | a | 12 | 203–209/0.04 | 81.55 | 81.66 | 10.90 | 11.09 | 3.52 | 3.48 |
| 804 | Linoleic acid | [structure] | A | c | 12 | 199–207/0.04 | 81.69 | 81.79 | 11.02 | 11.12 | 3.40 | 3.22 |
| 805 | Linoleic acid | [structure] | A | a | 12 | 220–224/0.07 | 74.69 | 74.82 | 9.65 | 9.88 | 3.35 | 3.16 |
| 806 | Linoleic acid | [structure] | A | d | 12 | 219–224/0.06 | 74.69 | 74.77 | 9.65 | 9.75 | 3.35 | 3.25 |
| 807 | Linoleic acid | [structure] | B | b | 18 | 216–221/0.05 | 74.69 | 74.79 | 9.65 | 9.70 | 3.35 | 3.19 |
| 808 | Linoleic acid | [structure] | A | e | 12 | 220–238/0.06 | 69.01 | 69.22 | 8.69 | 8.82 | 3.10 | 3.01 |
| 809 | Linoleic acid | [structure] | D | f | 12 | 215–238/0.09 | 67.52 | 67.74 | 8.72 | 8.93 | 3.03 | 2.98 |
| 810 | Linoleic acid | [structure] | C | a | 16 | 222–236/0.1 | 67.52 | 67.82 | 8.72 | 8.90 | 3.03 | 2.94 |

-continued

| Ex. | Acid | Amine | Agent | Solvent | Reaction time | b.p. °C/mmHg. | C % Theoretical | C % Analytical | H % Theoretical | H % Analytical | N % Theoretical | N % Analytical |
|---|---|---|---|---|---|---|---|---|---|---|---|---|
| 811 | Linoleic acid | NH₂—CH(CH₃)—C₆H₄—Br | A | a | 16 | 217–229/0.04 | 67.52 | 67.62 | 8.72 | 8.90 | 3.03 | 2.98 |
| 812 | Linoleic acid | NH₂CH(C₂H₅)—C₆H₄—Br | F | d | 16 | 220–239/0.06 | 68.06 | 68.17 | 8.82 | 8.93 | 2.94 | 2.78 |
| 813 | Linoleic acid | NH₂CH(CH₃)—C₆H₄—CH₃ | B | b | 20 | 212–223/0.05 | 81.55 | 81.75 | 10.90 | 11.08 | 3.52 | 3.40 |
| 814 | Linoleic acid | NH₂CH(l)(CH₃)—C₆H₄—Cl | A | e | 16 | 218–222/0.07 | 74.69 | 74.88 | 9.65 | 9.76 | 3.35 | 3.18 |
| 815 | Linoleic acid | NH₂CH(d)(CH₃)—C₆H₄—Cl | E | a | 18 | 220–218/0.06 | 74.69 | 74.81 | 9.65 | 9.82 | 3.35 | 3.19 |
| 816 | Linoleic acid | NH₂CH(CH₃)—C₆H₄(o-OCH₃) | A | a | 12 | 216–218/0.04 | 78.40 | 78.60 | 10.48 | 10.59 | 3.39 | 3.21 |
| 817 | Linoleic acid | NH₂CH(CH₃)—C₆H₄(m-OCH₃) | A | a | 10 | 218–229/0.03 | 78.40 | 78.46 | 10.48 | 10.53 | 3.39 | 3.19 |
| 818 | Linoleic acid | NH₂CH(CH₃)—C₆H₄—OCH₃ | B | b | 16 | 215–226/0.03 | 78.40 | 78.52 | 10.48 | 10.62 | 3.39 | 3.20 |
| 819 | Oleic acid | NH₂CH(CH₃)—C₆H₄—C₂H₅ | A | a | 10 | 205–220/0.07 | 81.29 | 81.41 | 11.45 | 11.56 | 3.39 | 3.29 |
| 820 | Oleic acid | NH₂CH(C₂H₅)—C₆H₄—C₂H₅ | A | a | 10 | 211–223/0.07 | 81.44 | 81.62 | 11.55 | 11.71 | 3.28 | 3.09 |
| 821 | Oleic acid | NH₂CH(CH₃)—C₆H₄—Br | B | b | 18 | 224–238/0.07 | 67.24 | 67.51 | 9.05 | 9.11 | 3.01 | 2.89 |
| 822 | Isostearic acid | NH₂CH(CH₃)—C₆H₄—CH₃ | A | c | 12 | 200–215/0.08 | 80.73 | 80.91 | 11.83 | 11.94 | 3.40 | 3.33 |
| 823 | Isostearic acid | NH₂CH(C₂H₅)—C₆H₄—C(CH₃)₃ | A | d | 16 | 206–224/0.07 | 81.33 | 81.52 | 12.11 | 12.42 | 3.06 | 3.00 |
| 824 | Isostearic acid | NH₂CH(CH₃)—C₆H₄—Cl | C | e | 14 | 218–239/0.06 | 74.02 | 74.21 | 10.43 | 10.56 | 3.32 | 3.06 |
| 825 | Isostearic acid | NH₂CH(CH₃)—C₆H₄—Br | D | d | 14 | 215–226/0.05 | 66.95 | 67.13 | 9.44 | 9.57 | 3.00 | 3.05 |

-continued

| Ex. | Acid | Amine | Agent | Solvent | Reaction time | b.p. °C/mmHg. | C % Theoretical | C % Analytical | H % Theoretical | H % Analytical | N % Theoretical | N % Analytical |
|---|---|---|---|---|---|---|---|---|---|---|---|---|
| 826 | Isostearic acid | NH$_2$CH(CH$_3$)—C$_6$H$_4$—OCH$_3$ | E | a | 14 | 218–230/0.05 | 77.64 | 77.74 | 11.34 | 11.43 | 3.35 | 3.14 |
| 827 | Isostearic acid | NH$_2$CH(C$_2$H$_5$)—C$_6$H$_4$—OC$_2$H$_5$ | B | b | 20 | 218–224/0.05 | 78.14 | 78.37 | 11.53 | 11.68 | 3.14 | 3.02 |
| 828 | Linolenic acid | NH$_2$CH(CH$_3$)—C$_6$H$_4$—OC$_2$H$_5$ | A | e | 14 | 216–230/0.05 | 79.61 | 79.76 | 10.18 | 10.35 | 3.29 | 3.14 |
| 829 | Linolenic acid | NH$_2$CH(C$_2$H$_5$)—C$_6$H$_4$—OCH$_3$ | C | e | 8 | 215–227/0.05 | 79.61 | 79.75 | 10.18 | 10.30 | 3.29 | 3.11 |
| 830 | Linolenic acid | NH$_2$—CH(CH$_3$)—C$_6$H$_4$—CH$_3$ | E | a | 16 | 212–220/0.05 | 81.97 | 82.18 | 10.45 | 10.50 | 3.54 | 3.47 |
| 831 | Linolenic acid | NH$_2$CH(CH$_3$)—C$_6$H$_4$—Cl | A | f | 10 | 198–218/0.03 | 75.09 | 75.21 | 9.14 | 9.34 | 3.36 | 3.33 |
| 832 | Linseed oil acid | NH$_2$—CH(CH$_3$)—C$_6$H$_4$—CH$_3$ | F | a | 18 | 203–203/0.03 | | | | | | |
| 833 | Linseed oil acid | NH$_2$CH(CH$_3$)—C$_6$H$_4$—Cl | B | b | 20 | 200–218/0.03 | | | | | | |
| 834 | Safflower oil acid | NH$_2$CH(CH$_3$)—C$_6$H$_4$—CH$_3$ | A | a | 12 | 203–215/0.03 | | | | | | |
| 835 | Safflower oil acid | NH$_2$CH(C$_2$H$_5$)—C$_6$H$_4$—CH$_3$ | A | a | 12 | 209–224/0.05 | | | | | | |
| 836 | Safflower oil acid | NH$_2$CH$^{(d)}$(CH$_3$)—C$_6$H$_4$—OC$_2$H$_5$ | A | f | 12 | 208–220/0.05 | | | | | | |
| 837 | Safflower oil acid | NH$_2$CH(C$_2$H$_5$)—C$_6$H$_4$—Br | F | e | 14 | 220–225/0.03 | | | | | | |
| 838 | Soybean oil acid | NH$_2$CH(C$_3$H$_7$)—C$_6$H$_4$—C$_3$H$_7$ | A | a | 12 | 210–232/0.05 | | | | | | |
| 839 | Sunflower oil acid | NH$_2$CH(C$_3$H$_7$)—C$_6$H$_4$—OC$_4$H$_9$ | A | a | 10 | 208–232/0.05 | | | | | | |
| 840 | Castor oil acid | NH$_2$CH(CH$_3$)—C$_6$H$_3$(Cl)—Cl | A | c | 10 | 205–225/0.05 | | | | | | |

-continued

| Ex. | Acid | Amine | Agent | Solvent | Reaction time | b.p. °C/mmHg. | C % Theoretical | C % Analytical | H % Theoretical | H % Analytical | N % Theoretical | N % Analytical |
|---|---|---|---|---|---|---|---|---|---|---|---|---|
| 841 | Rape-seed oil acid | $NH_2CH(CH_3)$-C$_6$H$_4$-OC$_2$H$_5$ | C | d | 12 | 220–229/0.05 | | | | | | |
| 842 | Cottonseed oil acid | $NH_2CH(C_3H_7)$-C$_6$H$_4$-OCH$_3$ | D | e | 12 | 218–233/0.05 | | | | | | |
| 843 | Olive oil acid | $NH_2CH(CH_3)$-C$_6$H$_4$-C$_2$H$_5$ | E | a | 14 | 204–226/0.05 | | | | | | |
| 844 | Peanut oil acid | $NH_2CH(CH_3)$-C$_6$H$_4$-OCH$_3$ | A | e | 10 | 218–228/0.05 | | | | | | |
| 845 | Locust oil acid | $NH_2CH(C_2H_5)$-C$_6$H$_4$-OCH$_3$ | A | e | 10 | 215–225/0.05 | | | | | | |
| 846 | Chrysalis oil acid | $NH_2CH(C_2H_5)$-C$_6$H$_3$(CH$_3$)-Cl | B | b | 20 | 232–241/0.05 | | | | | | |
| 847 | Shark oil acid | $NH_2CH(CH_3)$-C$_6$H$_3$(OCH$_3$)(CH$_3$) | A | e | 10 | 225–244/0.05 | | | | | | |
| 848 | Sardine oil acid | $NH_2CH(CH_3)$-C$_6$H$_4$-OC$_2$H$_5$ | F | e | 10 | 206–220/0.06 | | | | | | |
| 849 | Mackerel oil acid | $NH_2CH(CH_3)$-C$_6$H$_4$-Br | A | a | 12 | 214–231/0.05 | | | | | | |
| 850 | Herring oil acid | $NH_2CH(CH_3)$-C$_6$H$_4$-CH$_3$ | C | a | 12 | 194–228/0.05 | | | | | | |
| 851 | Saurel oil acid | $NH_2CH(CH_3)$-C$_6$H$_4$-C$_4$H$_9$ | A | a | 10 | 197–229/0.07 | | | | | | |
| 852 | God oil acid | $NH_2CH(C_4H_9)$-C$_6$H$_4$-CH$_3$ | F | e | 12 | 198–228/0.05 | | | | | | |
| 853 | Gray mullet oil acid | $NH_2CH(CH_3)$-C$_6$H$_4$-OCH$_3$ | A | f | 8 | 193–238/0.06 | | | | | | |
| 854 | Menhaden oil acid | $NH_2CH(CH_3)$-C$_6$H$_4$-OCH$_3$ | A | d | 12 | 188–238/0.05 | | | | | | |
| 855 | Flatfish oil acid | $NH_2CH(C_2H_5)$-C$_6$H$_4$-Cl | A | c | 12 | 194–237/0.05 | | | | | | |

-continued

| Ex. | Acid | Amine | Agent | Solvent | Reaction time | b.p. °C/mmHg | C % Theoretical | C % Analytical | H % Theoretical | H % Analytical | N % Theoretical | N % Analytical |
|---|---|---|---|---|---|---|---|---|---|---|---|---|
| 856 | Residual oil acid | 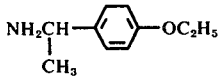 | A | a | 12 | 200–228/0.05 | | | | | | |

EXAMPLE 857

A mixture of 28 g. of linoleic acid, 21 g. of α-benzylbenzylamine, 300 ml. of toluene and 0.4 g. of p-toluenesulfonic acid was refluxed for 8 hrs. using water separator. The toluene layer was washed with acid, alkali and water, and was then dried, concentrated and purified by chromatography on an alumina column whereby 29.2 g. of a semisolid was obtained. Elementary analysis:

| | Theoretical | Analytical |
|---|---|---|
| C (%) | 83.60 | 83.70 |
| H (%) | 9.87 | 10.08 |
| N (%) | 3.05 | 3.08 |

Examples 858–888 are shown in the following table, in which:

Dehydrating agent:
A. p-Toluenesulfonic acid.
B. p-Toluenesulfonic acid chloride.
C. Sulfuric acid.
D. Phenolsulfonic acid.
E. IRA-400.
F. Amberlist - 15.

Solvent:
a. Toluene.
b. Pyridine.
c. Benzene.
d. Chloroform.
e. Xylene.
f. Tetrachlorocarbon.

| Example | Acid | Amine | Agent | Solvent | Reaction time (hr) | Property | C % Theoretical | C % Analytical | H % Theoretical | H % Analytical | N % Theoretical | N % Analytical |
|---|---|---|---|---|---|---|---|---|---|---|---|---|
| 858 | Linoleic acid | d (+) [α]$_D$ +26.6 | B | b | 20 | 45°–50° | 83.60 | 83.77 | 9.87 | 10.04 | 3.05 | 3.15 |
| 859 | Linoleic acid | l (−) [α]$_D$ −27.1 | E | e | 12 | " | 83.60 | 83.79 | 9.87 | 10.01 | 3.05 | 3.14 |
| 860 | Oleic acid | dl (±) | A | c | 10 | Semi-solid | 83.24 | 83.36 | 10.26 | 10.32 | 3.03 | 3.14 |
| 861 | Isostearic acid | dl (±) | A | e | 10 | " | 82.88 | 83.02 | 10.65 | 10.41 | 3.02 | 3.10 |
| 862 | Isostearic acid | d (+) | C | e | 10 | " | 82.88 | 83.05 | 10.65 | 10.87 | 3.02 | 3.09 |
| 863 | Isostearic acid | l (−) | A | a | 10 | " | 82.88 | 83.06 | 10.65 | 10.69 | 3.02 | 3.07 |
| 864 | Linolenic acid | dl (±) | A | a | 10 | " | 83.97 | 84.12 | 9.47 | 9.72 | 3.06 | 3.12 |
| 865 | Linseed oil fatty acid | dl (±) | A | a | 10 | " | | | | | | |
| 866 | Safflower oil fatty acid | d (+) | A | a | 10 | " | | | | | | |
| 867 | Safflower oil fatty acid | l (−) | A | a | 10 | " | | | | | | |
| 868 | Safflower oil fatty acid | dl (±) | F | f | 10 | " | | | | | | |
| 869 | Soybean oil acid | dl (±) | A | a | 12 | " | | | | | | |
| 870 | Sunflower oil acid | dl (±) | A | a | 12 | " | | | | | | |
| 871 | Castor oil acid | dl (±) | A | a | 12 | " | | | | | | |
| 872 | Rape-seed oil acid | dl (±) | A | a | 12 | " | | | | | | |
| 873 | Cottonseed oil acid | " | D | a | 12 | " | | | | | | |
| 874 | Olive oil acid | " | A | a | 12 | " | | | | | | |
| 875 | Peanut oil acid | " | A | a | 12 | " | | | | | | |
| 876 | Locust oil acid | " | A | a | 12 | " | | | | | | |
| 877 | Chrysalis oil acid | " | A | a | 12 | " | | | | | | |
| 878 | Shark oil acid | " | A | e | 12 | " | | | | | | |
| 879 | Sardine oil acid | " | A | a | 12 | " | | | | | | |
| 880 | Mackerel oil acid | " | A | a | 12 | " | | | | | | |
| 881 | Herring oil acid | " | A | a | 12 | " | | | | | | |
| 882 | Saurel oil acid | " | A | a | 12 | " | | | | | | |
| 883 | Cod oil acid | " | A | a | 12 | " | | | | | | |
| 884 | Gray mullet oil acid | " | A | a | 12 | " | | | | | | |
| 885 | Menhaden oil acid | " | A | a | 12 | " | | | | | | |
| 886 | Flatfish oil acid | " | A | a | 12 | " | | | | | | |
| 887 | Residual oil acid | " | A | a | 12 | " | | | | | | |

EXAMPLE 888

Linoleic acid (28 g.), 21 g. of α-benzylbenzylamine and 23.2 g. of dicyclohexyl carbodiimide were individually dissolved in 50 ml. of toluene. The solutions were mixed together in one portion, and the mixed solution was allowed to stand at room temperature for 8 hours. After filtering the solution, the filtrate was washed with acid alkali and water, and was dried, concentrated and purified chromatographically to obtain 22.5 g. of a semi-solid, desired product. Elementary analysis:

| | Theoretical | Analytical |
|---|---|---|
| C (%) | 83.60 | 84.01 |
| H (%) | 9.87 | 10.08 |
| N (%) | 3.05 | 3.21 |

Examples 889–918 are shown in the following table:

| Ex. No. | Acid | Amine | B<br>BN=C=NB | Solvent | $\alpha_D$ | Property | C % Theoretical | C % Analytical | H % Theoretical | H % Analytical | N % Theoretical | N % Analytical |
|---|---|---|---|---|---|---|---|---|---|---|---|---|
| 889 | Linoleic acid | d (+) | cyclohexyl | Ether | +26.7 | 45°–50° | 83.60 | 83.80 | 9.87 | 10.04 | 3.05 | 3.14 |
| 890 | Linoleic acid | l (−) | cyclohexyl | Dioxane | −26.9 | " | 83.60 | 83.71 | 9.87 | 9.99 | 3.05 | 3.25 |
| 891 | Oleic acid | dl (±) | CH$_3$–CH–CH$_3$ | Tetrahydrofuran | | Semi-solid | 83.24 | 83.50 | 10.26 | 10.42 | 3.05 | 3.19 |
| 892 | Isostearic acid | dl (±) | phenyl | Ether | | " | 82.88 | 83.01 | 10.65 | 10.79 | 3.02 | 3.17 |
| 893 | Isostearic acid | d (+) | cyclohexyl | Benzene | | " | 82.88 | 83.05 | 10.65 | 10.79 | 3.02 | 3.17 |
| 894 | Isostearic acid | l (−) | cyclohexyl | Toluene | | " | 82.88 | 83.12 | 10.65 | 10.83 | 3.02 | 3.25 |
| 895 | Linolenic acid | dl (±) | cyclohexyl | Toluene | | " | 83.97 | 84.12 | 9.47 | 9.71 | 3.06 | 3.16 |
| 896 | Linseed oil | dl (±) | cyclohexyl | Benzene | | " | | | | | | |
| 897 | Safflower oil | d (+) | cyclohexyl | Benzene | | " | | | | | | |
| 898 | Safflower oil | l (−) | cyclohexyl | Toluene | | " | | | | | | |
| 899 | Safflower oil | dl (±) | cyclohexyl | Toluene | | " | | | | | | |
| 900 | Soybean oil acid | | cyclohexyl | Chloroform | | " | | | | | | |
| 901 | Sunflower oil acid | | cyclohexyl | Chloroform | | " | | | | | | |
| 902 | Castor oil acid | | cyclohexyl | Toluene | | " | | | | | | |
| 903 | Rape-seed oil acid | | cyclohexyl | Toluene | | " | | | | | | |
| 904 | Cottonseed oil acid | | cyclohexyl | Toluene | | " | | | | | | |
| 905 | Olive oil acid | | cyclohexyl | Toluene | | " | | | | | | |
| 906 | Peanut oil acid | | cyclohexyl | Benzene | | " | | | | | | |
| 907 | Locust oil acid | | cyclohexyl | Benzene | | " | | | | | | |
| 908 | Chrysalis oil acid | | cyclohexyl | Tetrachlorocarbon | | " | | | | | | |
| 909 | Shark oil acid | | cyclohexyl | Pyridine | | " | | | | | | |
| 910 | Sardine oil acid | | cyclohexyl | Benzene | | " | | | | | | |
| 911 | Mackerel oil acid | | cyclohexyl | Ether | | " | | | | | | |
| 912 | Herring oil acid | | cyclohexyl | Ether | | " | | | | | | |
| 913 | Saurel oil acid | | cyclohexyl | Ether | | " | | | | | | |

| Ex. No. | Acid | Amine | B BN=C=NB | Solvent | $\alpha_D$ | Property | C % Theoretical | C % Analytical | H % Theoretical | H % Analytical | N % Theoretical | N % Analytical |
|---|---|---|---|---|---|---|---|---|---|---|---|---|
| 914 | Cod oil acid | | —⟨⟩ | Toluene | | " | | | | | | |
| 915 | Gray mullet oil acid | | —⟨⟩ | Toluene | | " | | | | | | |
| 916 | Menhaden oil acid | | —⟨⟩ | Toluene | | " | | | | | | |
| 917 | Flatfish oil acid | | —⟨⟩ | Toluene | | " | | | | | | |
| 918 | Residual oil acid | | —⟨⟩ | Toluene | | " | | | | | | |

EXAMPLE 919

Examples 920–942 are shown in the following tables:

| Example No. | Acid moiety | Amine | Agent | Reaction temperature °C. | Reaction time (hr) | Property | C % Theoretical | C % Analytical | H % Theoretical | H % Analytical | N % Theoretical | N % Analytical |
|---|---|---|---|---|---|---|---|---|---|---|---|---|
| 920 | Linoleic acid | d (+) | | 140 | 36 | 45°–50° | 83.60 | 83.72 | 9.87 | 9.98 | 3.05 | 3.21 |
| 921 | Linoleic acid | l (−) | | 140 | 36 | " | 83.60 | 83.69 | 9.87 | 9.98 | 3.05 | 3.22 |
| 922 | Oleic acid | dl (±) | | 140 | 40 | " | 83.24 | 83.34 | 10.26 | 10.41 | 3.03 | 3.06 |
| 923 | Isostearic acid | dl (±) | | 150 | 40 | " | 82.88 | 83.05 | 10.65 | 10.77 | 3.02 | 3.05 |
| 924 | Isostearic acid | d (+) | | 150 | 40 | " | 82.88 | 83.06 | 10.65 | 10.71 | 3.02 | 3.13 |
| 925 | Isostearic acid | l (−) | | 180 | 36 | " | 82.88 | 83.00 | 10.65 | 10.82 | 3.02 | 3.09 |
| 926 | Linolenic acid | dl (±) | | 150 | 40 | " | 83.97 | 84.12 | 9.47 | 9.63 | 3.06 | 2.99 |
| 927 | Linseed oil | dl (±) | | 150 | 40 | " | | | | | | |
| 928 | Safflower oil | d (+) | | 180 | 40 | " | | | | | | |
| 929 | Safflower oil | l (−) | | 180 | 36 | " | | | | | | |
| 930 | Safflower oil | dl (±) | Boric acid | 180 | 16 | " | | | | | | |

| Example No. | Acid moiety | Agent | Reaction temperature ° C. | Reaction time (hr.) | Property |
|---|---|---|---|---|---|
| 931 | Soybean oil acid | | 140 | 40 | Semi-solid |
| 932 | Sunflower oil acid | | 150 | 40 | " |
| 933 | Castor oil acid | Boric acid | 150 | 20 | " |
| 934 | Rape-seed oil acid | | 150 | 40 | " |
| 935 | Cottonseed oil acid | | 160 | 40 | " |
| 936 | Olive oil acid | | 150 | 40 | " |
| 937 | Peanut oil acid | | 150 | 40 | " |
| 938 | Chrysalis oil acid | | 150 | 40 | " |
| 939 | Shark oil acid | | 150 | 40 | " |
| 940 | Sardine oil acid | | 150 | 40 | " |
| 941 | Mackerel oil acid | | 150 | 40 | " |
| 942 | Herring oil acid | | 150 | 40 | " |

A mixture of 10 g. of linoleic acid and 11 g. of α-benzylbenzylamine was heated at 180° C. for 24 hours. The reaction mixture was purified chromatographically to obtain 14.2 g. of a 45°–48° C. desired product. Elementary analysis:

| | Theoretical | Analytical |
|---|---|---|
| C (%) | 83.60 | 83.76 |
| H (%) | 9.87 | 10.02 |
| N (%) | 3.05 | 3.30 |

EXAMPLE 943

A mixture of 10 g. of methyl linoleate and 11.2 g. of α-benzyl-benzylamine was heated in a nitrogen atmosphere at 180° C. for 50 hours removing methanol out of the reaction system. The reaction mixture was purified chromatographically to obtain 15.3 g. desired product up 46°–49° C. Elementary analysis:

| | Theoretical | Analytical |
|---|---|---|
| C (%) | 83.60 | 83.61 |
| H (%) | 9.87 | 10.09 |

|   | Theoretical | Analytical |
|---|---|---|
| N (%) | 3.05 | 3.25 |

EXAMPLE 944

A mixture of 10 g. of methyl isostearate, 11.2 g. of α-benzyl-benzylamine and 1 g. of sodium methylate. The mixture was reacted at 150° C. for 3 hours, removing methanol during the reaction. Subsequently, the reaction product was dissolved in ether and the ether solution was washed with acid, alkali and water according to ordinary procedures and was then dried and purified chromatographically to obtain 15.8 g. of a semi-solid desired compound. Elementary analysis:

|   | Theoretical | Analytical |
|---|---|---|
| C (%) | 82.88 | 83.78 |
| H (%) | 10.65 | 10.21 |
| N (%) | 3.02 | 3.16 |

EXAMPLE 945

A mixture of 10 g. of ethyl oleate, 11 g. of α-benzyl-benzylamine 0.5 g. of sodium and 8 ml. of ethyl alcohol was heated at 160° C. for about 2 hours removing ethyl alcohol. Thereafter, the same treatments as in Example 857 were effected to obtain 14.0 g. of a desired product. Elementary analysis:

|   | Theoretical | Analytical |
|---|---|---|
| C (%) | 83.24 | 83.66 |
| H (%) | 10.26 | 9.91 |
| N (%) | 3.03 | 3.21 |

EXAMPLE 946

A mixture of 10 g. of safflower oil and 11 g. of α-benzyl-benzylamine was heated in an autoclave at 200° C. for 22 hours. Immediately thereafter, the same treatments as in Example 857 were effected to obtain 15.0 g. of a desired product.

Examples 947–987 are shown in the following tables:

| Example No. | Acid moiety | Amine | Agent | Reaction temperature ° C. | Reaction time (hr) | Property | C % Theoretical | C % Analytical | H % Theoretical | H % Analytical | N % Theoretical | N % Analytical |
|---|---|---|---|---|---|---|---|---|---|---|---|---|
| 947 | Methyl linoleate | d (+) |  | 160 | 49 | 45°–50° | 83.60 | 83.72 | 9.87 | 10.11 | 3.05 | 2.94 |
| 948 | Methyl linoleate | l (−) |  | 160 | 48 | " | 83.60 | 83.74 | 9.87 | 10.06 | 3.05 | 2.87 |
| 949 | Ethyl oleate | d (+) |  | 140 | 48 | Semi-solid | 83.24 | 83.34 | 10.26 | 10.41 | 3.03 | 2.90 |
| 950 | Methyl isostearate | dl (±) | NaOCH₃ | 140 | 4 | " | 82.88 | 83.10 | 10.65 | 10.88 | 3.02 | 2.88 |
| 951 | Methyl isostearate | d (+) |  | 140 | 49 | " | 82.88 | 83.09 | 10.65 | 10.82 | 3.02 | 2.91 |
| 952 | Methyl isostearate | l (−) |  | 160 | 56 | " | 82.88 | 83.11 | 10.65 | 10.72 | 3.02 | 2.84 |
| 953 | Methyl linolenate | d (+) |  | 180 | 50 | " | 83.97 | 84.21 | 9.47 | 9.63 | 3.06 | 2.87 |
| 954 | Linseed oil | dl (±) |  | 180 | 50 | " |  |  |  |  |  |  |
| 955 | Safflower oil | d (+) |  | 180 | 50 | " |  |  |  |  |  |  |
| 956 | Safflower oil | l (−) |  | 170 | 50 | " |  |  |  |  |  |  |
| 957 | Safflower oil methyl ester | d (+) |  | 170 | 60 | " |  |  |  |  |  |  |

| Example No. | Acid moiety | Agent | Reaction temperature. ° C. | Reaction time (hr) | Property |
|---|---|---|---|---|---|
| 958 | Soybean oil acid methyl ester | Boric acid | 160 | 50 | Semi-solid |
| 959 | Castor oil acid methyl ester |  | 160 | 50 | " |
| 960 | Cottonseed oil acid methyl ester |  | 160 | 50 | " |
| 961 | Olive oil acid methyl ester |  | 160 | 50 | " |
| 962 | Peanut oil acid methyl ester |  | 140 | 50 | " |
| 963 | Shark oil acid methyl ester |  | 180 | 66 | " |
| 964 | Sardine oil acid methyl ester |  | 180 | 66 | " |
| 965 | Mackerel oil acid methyl ester |  | 180 | 56 | " |
| 966 | Herring oil acid methyl ester |  | 180 | 66 | " |
| 967 | Cod oil acid methyl ester |  | 200 | 65 | " |
| 968 | Flatfish acid methyl ester |  | 140 | 80 | " |
| 969 | Soybean oil |  | 140 | 60 | " |
| 970 | Sunflower oil |  | 140 | 60 | " |
| 971 | Castor oil |  | 160 | 60 | " |
| 972 | Rape-seed oil |  | 160 | 60 | " |
| 973 | Cottonseed oil |  | 180 | 60 | " |
| 974 | Olive oil |  | 160 | 60 | " |
| 975 | Peanut oil |  | 160 | 60 | " |
| 976 | Locust oil |  | 160 | 60 | " |
| 977 | Chrysalic oil |  | 160 | 60 | " |
| 978 | Shark oil |  | 160 | 60 | " |
| 979 | Sardine oil |  | 160 | 60 | " |
| 980 | Mackerel oil |  | 160 | 60 | " |
| 981 | Herring oil | Boric acid | 160 | 60 | " |
| 982 | Saurel oil |  | 140 | 60 | " |

| | | | | | |
|---|---|---|---|---|---|
| 983 | Cod oil | | 140 | 60 | " |
| 984 | Gray mullet oil | | 140 | 50 | " |
| 985 | Menhaden oil | | 140 | 50 | " |
| 986 | Flatfish oil | | 140 | 40 | " |
| 987 | Residual oil | | 140 | 50 | " |

EXAMPLE 988

A solution of 30 g. of linoleic acid chloride in 50 ml. of anhydrous ether was added to a solution of 22.5 g. of α-benzyl-benzylamine and 8 g. of trimethylamine in 100 ml. of anhydrous ether. The reaction mixture was boiled for 2 hours after addition. Subsequently, the ether solution was washed with acid, alkali and water, and was dried, concentrated and purified chromatographically in the same manner as in Example 857 to obtain 48 g. of a desired product. Elementary analysis:

| | Theoretical | Analytical |
|---|---|---|
| C (%) | 83.60 | 83.79 |
| H (%) | 9.87 | 10.04 |
| N (%) | 3.05 | 3.27 |

Examples 989–1019 are shown in the following tables:

| Example No. | Acid | Amine | Agent | Solvent | $\alpha_0$ | Property | C % Theoretical | C % Analytical | H % Theoretical | H % Analytical | N % Theoretical | N % Analytical |
|---|---|---|---|---|---|---|---|---|---|---|---|---|
| 989 | Linoleic acid Cl | dl (±) | Triethylamine | Ether $[\alpha]_D$ | +27.0 | 47–50° | 83.60 | 83.88 | 9.87 | 9.99 | 3.05 | 3.12 |
| 990 | Linoleic acid Cl | d (+) | NaOH | Acetone $[\alpha]_D$ | +27.0 | " | 83.60 | 83.79 | 9.87 | 9.91 | 3.05 | 2.88 |
| 991 | Linoleic acid Cl | l (−) | Pyridine | Toluene $[\alpha]_D$ | −27.5 | " | 83.60 | 83.71 | 9.87 | 10.21 | 3.05 | 2.79 |
| 992 | Oleic acid Cl | dl (±) | Pyridine | Benzene | | Semi-solid | 83.24 | 83.51 | 10.26 | 10.34 | 3.03 | 3.00 |
| 993 | Isostearic acid Cl | dl (±) | $K_2CO_3$ | M I B K | | " | 82.88 | 83.09 | 10.65 | 10.91 | 3.02 | 2.81 |
| 994 | Isostearic acid Cl | d (+) | NaOH | Acetone-water | | " | 82.88 | 83.09 | 10.65 | 10.90 | 3.02 | 2.79 |
| 995 | Isotearic acid Cl | l (−) | KOH | Dioxane-water | | " | 82.88 | 83.01 | 10.65 | 10.87 | 3.02 | 2.99 |
| 996 | Linolenic acid Cl | dl (±) | Dimethylaniline | Ether | | " | 83.97 | 84.12 | 9.47 | 9.67 | 3.06 | 2.95 |
| 997 | Linseed oil Cl | dl (±) | Triethylamine | Toluene | | " | | | | | | |
| 998 | Safflower oil Cl | d (+) | Triethylamine | Toluene | | " | | | | | | |
| 999 | Safflower oil Cl | l (−) | Triethylamine | Toluene | | " | | | | | | |
| 1000 | Safflower oil Cl | dl (±) | Triethylamine | Toluene | | " | | | | | | |

| Example No. | Acid | | Agent | Solvent | Property |
|---|---|---|---|---|---|
| 1001 | Soybean oil acid | Cl | Pyridine | Toluene | Semi-solid |
| 1002 | Sunflower oil acid | Cl | $K_2CO_3$ | M I B K | " |
| 1003 | Castor oil acid | Cl | Dimethylaniline | Toluene | " |
| 1004 | Rape seed oil acid | Cl | Trimethylamine | Ether | " |
| 1005 | Cottonseed oil acid | Cl | Pyridine | Ether | " |
| 1006 | Olive oil acid | Cl | $K_2CO_3$ | Acetone-water | " |
| 1007 | Peanut oil acid | Cl | NaOH | Tetrahydrofuran-water | " |
| 1008 | Locust oil acid | Cl | KOH | Dioxane-water | " |
| 1009 | Chrysalis oil acid | Cl | $K_2CO_3$ | M I B K | " |
| 1010 | Shark oil acid | Cl | $Na_2CO_3$ | Acetone | " |
| 1011 | Sardine oil acid | Cl | Triethylamine | Toluene | " |
| 1012 | Mackerel oil acid | Cl | Triethylamine | Toluene | " |
| 1013 | Herring oil acid | Cl | Triethylamine | Ether | " |
| 1014 | Saurel oil acid | Cl | Triethylamine | Ether | " |
| 1015 | Cod oil acid | Cl | Triethylamine | Ether | " |
| 1016 | Gray mullet oil acid | Cl | NaOH | Acetone-water | " |
| 1017 | Menhaden oil acid | Cl | Pyridine | Ether | " |
| 1018 | Flatfish oil acid | Cl | Pyridine | Toluene | " |
| 1019 | Residual oil acid | Cl | Pyridine | Ether | " |

EXAMPLE 1020

A solution of 20 g. of linoleic acid, 17 g. of α-methyl-p-nitrobenzylamine 0.5 g. of p-toluenesulfonic acid in 300 ml. of toluene was refluxed using a water-separator for 8 hours. The toluene layer was washed with acid, alkali and water, and was then dried and concentrated to obtain 22.3 g. of a desired product, $n_D^{23}$ 1.5111. Elementary analysis:

|  | Theoretical | Analytical |
|---|---|---|
| C (%) | 72.86 | 72.67 |
| H (%) | 9.41 | 9.21 |
| N (%) | 6.54 | 6.66 |

Examples 1021–1051 are shown in the following tables, in which:

Dehydration assistant:
A. p-Toluenesulfonic acid.
B. p-Toluenesulfonic acid chloride.
C. Sulfuric acid.
D. Phenolsulfonic acid.
E. IRA-400.
F. Amberlist-15.

Solvent:
a. Toluene.
b. Pyridine.
c. Benzene.
d. Chloroform.
e. Xylene.
f. Tetrachlorocarbon.

| Ex. No. | Acid | Amine | Agent | Solvent | Reaction time (hr) | $n_D$ | C % Theoretical | C % Analytical | H % Theoretical | H % Analytical | N % Theoretical | N % Analytical |
|---|---|---|---|---|---|---|---|---|---|---|---|---|
| 1021 | Oleic acid | NH₂CH(C₂H₅)-C₆H₄-NO₂ | A | a | 8 | 23° C 1.5123 | 72.93 | 73.16 | 9.97 | 10.13 | 6.30 | 6.05 |
| 1022 | Linolenic acid | NH₂CH(C₂H₅)-C₆H₄-NO₂ | B | b | 20 | 23° C 1.5100 | 73.60 | 73.90 | 9.15 | 9.32 | 6.36 | 6.12 |
| 1023 | Linoleic acid | NH₂CH(C₂H₅)-C₆H₄-NO₂ | A | e | 10 | 22.5° C 1.5133 | 73.26 | 73.52 | 9.56 | 9.72 | 6.33 | 6.14 |
| 1024 | Linoleic acid | NH₂CH(CH₃)-C₆H₄-NO₂ | D | c | 10 | 26° C 1.5109 | 72.86 | 72.99 | 9.41 | 9.58 | 6.54 | 6.37 |
| 1025 | Isostearic acid | (d) NH₂CH(CH₃)-C₆H₄-NO₂ | C | a | 14 | 28° C 1.5155 | 72.18 | 72.32 | 10.25 | 10.50 | 6.48 | 6.21 |
| 1026 | Isostearic acid | (l) NH₂CH(CH₃)-C₆H₄-NO₂ | E | e | 12 | 28° C 1.3152 | 72.18 | 72.22 | 10.25 | 10.45 | 6.48 | 6.11 |
| 1027 | Safflower oil acid | NH₂CH(CH₃)-C₆H₄-NO₂ | F | f | 12 | 23° C 1.5138 |  |  |  |  |  |  |
| 1028 | Soybean oil acid | NH₂CH(C₂H₅)-C₆H₄-NO₂ | A | e | 12 | 20° C 1.5131 |  |  |  |  |  |  |
| 1029 | Sesame oil acid | NH₂CH(CH₃)-C₆H₄-NO₂ | A | e | 12 | 19° C 1.5114 |  |  |  |  |  |  |
| 1030 | Castor oil acid | NH₂CH(CH₃)-C₆H₄-NO₂ | C | a | 12 | 22° C 1.5122 |  |  |  |  |  |  |
| 1031 | Corn oil acid | NH₂CH(C₃H₇)-C₆H₄-NO₂ | A | a | 12 | 20° C 1.5133 |  |  |  |  |  |  |

| Example No. | Acid | Amine | Agent | Solvent | Reaction time | $n_D$ |
|---|---|---|---|---|---|---|
| 1032 | Cottonseed oil acid | NH₂CH(CH₃)-C₆H₄-NO₂ | A | a | 12 | 23° C 1.5129 |
| 1033 | Olive oil acid | NH₂CH(CH₃)-C₆H₄-NO₂ | D | a | 8 | 25° C 1.5139 |

-continued

| Example No. | Acid | Amine | Agent | Solvent | Reaction time | $n_D$ | |
|---|---|---|---|---|---|---|---|
| 1034 | Linseed oil acid | 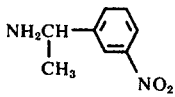 | A | d | 12 | 28.5° C | 1.5119 |
| 1035 | Rape-seed oil acid | 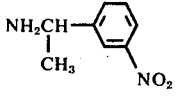 | A | f | 10 | 145 C | 1.5139 |
| 1036 | Rice bran oil acid | 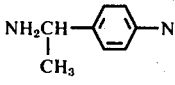 | A | a | 10 | 18° C | 1.5123 |
| 1037 | Chrysalis oil acid | 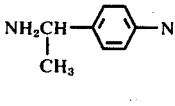 | D | a | 10 | 23° C | 1.5100 |
| 1038 | Flatfish oil acid | 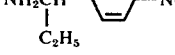 | C | a | 12 | 22° C | 1.5123 |
| 1039 | Shark oil acid | 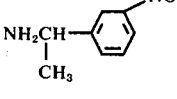 | E | e | 12 | 22° C | 1.5144 |
| 1040 | Whale oil acid | 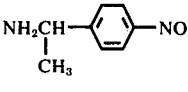 | A | d | 12 | 23° C | 1.5134 |
| 1041 | Cuttlefish oil acid | 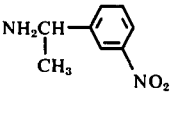 | B | b | 20 | 24.5° C | 1.5127 |
| 1042 | Sardine oil acid | 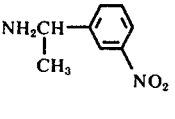 | F | e | 12 | 23° C | 1.5221 |
| 1043 | Mackerel oil acid | 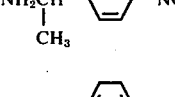 | B | b | 20 | 22.5° C | 1.5147 |
| 1044 | Saury pike oil acid | 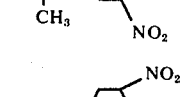 | A | d | 14 | 26.5° C | 1.5237 |
| 1045 | Herring oil acid | 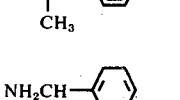 | A | a | 10 | 30° C | 1.5114 |
| 1046 | Saurel oil acid | 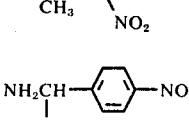 | C | e | 14 | 30° C | 1.5138 |
| 1047 | Menhaden oil acid | 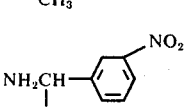 | D | a | 12 | 32° C | 1.5149 |
| 1048 | Cod oil acid |  | E | f | 12 | 30.5° C | 1.5139 |

-continued

| Example No. | Acid | Amine | Agent | Solvent | Reaction time | $n_D$ | |
|---|---|---|---|---|---|---|---|
| 1049 | Liver oil acid | NH₂CH(CH₃)-C₆H₄-NO₂ | F | e | 12 | 24.5° C | 1.5210 |
| 1050 | Menuke oil acid | NH₂CH(CH₃)-C₆H₄-NO₂ | A | a | 12 | 21.5° C | 1.5140 |
| 1051 | Residual oil acid | NH₂CH(C₂H₅)-C₆H₄-NO₂ | A | a | 12 | 20.3° C | 1.5133 |

EXAMPLE 1052

Linoleic acid (20 g.), 17 g. of α-methyl-o-nitrobenzylamine and 20 g. of dicyclohexyl carbodiimdie were individually dissolved in 100 ml. of toluene. The solutions were mixed together at one portion, and the mixed solution was allowed to stand at room temperature for 8 hours. After filtering the solution, the filtrate was washed with acid, alkali and water, and was then dried, concentrated and distilled to obtain 11.1 g. of a desired product, $n_D^{23}$ 1.5140. Elementary analysis:

|  | Theoretical | Analytical |
|---|---|---|
| C (%) | 72.86 | 72.68 |
| H (%) | 9.41 | 9.03 |
| N (%) | 6.54 | 7.01 |

Examples 1053–1073 are shown in the following table:

| Ex. No. | Acid | Amine | Agent B—N=C=N—B | Solvent | °C $n_D$ | | C % Theoretical | C % Analytical | H % Theoretical | H % Analytical | N % Theoretical | N % Analytical |
|---|---|---|---|---|---|---|---|---|---|---|---|---|
| 1053 | Oleic acid | NH₂CH(C₂H₅)-C₆H₄-NO₂ | cyclohexyl | Ether | 25°C | 1.5120 | 72.93 | 73.22 | 9.97 | 10.12 | 6.30 | 6.05 |
| 1054 | Linolenic acid | NH₂CH(C₂H₅)-C₆H₄-NO₂ | cyclohexyl | Toluene | 23°C | 1.5106 | 73.60 | 73.88 | 9.15 | 9.43 | 6.36 | 6.12 |
| 1055 | Linoleic acid | NH₂CH(C₂H₅)-C₆H₄-NO₂ | cyclohexyl | Benzene | 22°C | 1.5155 | 73.26 | 73.61 | 9.56 | 9.72 | 6.33 | 6.28 |
| 1056 | Linoleic acid | NH₂CH(CH₃)-C₆H₄-NO₂ | cyclohexyl | Benzene | 28°C | 1.5106 | 72.86 | 73.05 | 9.41 | 9.66 | 6.54 | 6.39 |
| 1057 | Isostearic acid | (d) NH₂CH(CH₃)-C₆H₄-NO₂ | cyclohexyl | Cyclohexane | 29°C | 1.5153 | 72.18 | 72.32 | 10.25 | 10.48 | 6.48 | 6.39 |
| 1058 | Isostearic acid | (l) NH₂CH(CH₃)-C₆H₄-NO₂ | CH₃-CH(CH₃)- | Benzene | 28°C | 1.5153 | 72.18 | 72.38 | 10.25 | 10.47 | 6.48 | 6.36 |
| 1059 | Safflower oil acid | NH₂CH(C₃...)-C₆H₄-NO₂ | cyclohexyl | Chloroform | 24°C | 1.5137 | | | | | | |
| 1060 | Soybean oil acid | NH₂CH(C₂H₅)-C₆H₄-NO₂ | CH₃-CH(C₃)- | Tetrachlorocarbon | 24°C | 1.5131 | | | | | | |

-continued

| Ex. No. | Acid | Amine | Agent B—N=C=N—B B | Solvent | °C $n_D$ | | C % Theoretical | C % Analytical | H % Theoretical | H % Analytical | N % Theoretical | N % Analytical |
|---|---|---|---|---|---|---|---|---|---|---|---|---|
| 1061 | Sesame oil acid | NH₂CH(CH₃)—C₆H₄—NO₂ (o) | cyclohexyl | Benzene | 22°C | 1.5115 | | | | | | |
| 1062 | Castor oil acid | NH₂CH(CH₃)—C₆H₄—NO₂ (p) | cyclohexyl | Ether | 22°C | 1.5122 | | | | | | |
| 1063 | Corn oil acid | NH₂CH(C₃H₇)—C₆H₄—NO₂ (p) | cyclohexyl | Benzene | 20°C | 1.5132 | | | | | | |
| 1064 | Cottonseed oil acid | NH₂CH(CH₃)—C₆H₄—NO₂ (m) | cyclohexyl | Benzene | 24°C | 1.5127 | | | | | | |
| 1065 | Olive oil acid | NH₂CH(CH₃)—C₆H₄—NO₂ (p) | cyclohexyl | Benzene | 22°C | 1.5142 | | | | | | |
| 1066 | Linseed oil acid | NH₂CH(CH₃)—C₆H₄—NO₂ (m) | cyclohexyl | Toluene | 24°C | 1.5122 | | | | | | |
| 1067 | Flatfish oil acid | NH₂CH(C₂H₅)—C₆H₄—NO₂ (p) | cyclohexyl | Pyridine | 22°C | 1.5124 | | | | | | |
| 1068 | Whale oil acid | NH₂CH(CH₃)—C₆H₄—NO₂ (p) | cyclohexyl | Dioxane | 23°C | 1.5133 | | | | | | |
| 1069 | Cuttlefish oil acid | NH₂CH(CH₃)—C₆H₄—NO₂ (m) | cyclohexyl | Tetrahydrofuran | 25°C | 1.5130 | | | | | | |
| 1070 | Sardine oil acid | NH₂CH(CH₃)—C₆H₄—NO₂ (m) | cyclohexyl | Pyridine | 24°C | 1.5145 | | | | | | |
| 1071 | Saurel oil acid | NH₂CH(CH₃)—C₆H₄—NO₂ (m) | cyclohexyl | Benzene | 24°C | 1.5141 | | | | | | |
| 1072 | Liver oil acid | NH₂C(CH₃)—C₆H₄—NO₂ (m) | cyclohexyl | Ether | 22°C | 1.5214 | | | | | | |
| 1073 | Residual oil acid | NH₂CH(C₂H₅)—C₆H₄—NO₂ (p) | cyclohexyl | Toluene | 20°C | 1.5136 | | | | | | |

EXAMPLE 1074

A mixture of 10 g. of linoleic acid and 9 g. of α-methyl-m-nitrobenzylamine was heated at 180° C. for 24 hours removing water during the reaction. The reaction product was dissolved in ether, and the ether solution was washed with acid, alkali and water and was then dried and concentrated to obtain 11.1 g. of a desired product, $n_D^{28}$ 1.5138. Elementary analysis:

| | Theoretical | Analytical |
|---|---|---|
| C (%) | 72.86 | 72.68 |
| H (%) | 9.41 | 9.24 |

-continued

| | Theoretical | Analytical |
|---|---|---|
| N (%) | 6.54 | 6.86 |

Examples 1075–1105 are shown in the following table:

| Ex. No. | Acid | Amine | Agent | Reaction temperature °C. | Reaction time (hr) | $n_D$ | C% Theoretical | C% Analytical | H% Theoretical | H% Analytical | N% Theoretical | N% Analytical |
|---|---|---|---|---|---|---|---|---|---|---|---|---|
| 1075 | Oleic acid | 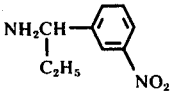 | | 180 | 24 | 22° C 1.5122 | 72.93 | 73.20 | 9.97 | 10.17 | 6.30 | 6.12 |
| 1076 | Linolenic acid | 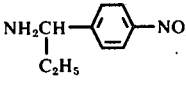 | | 180 | 24 | 24 " 1.5004 | 73.60 | 73.81 | 9.15 | 9.32 | 6.36 | 6.16 |
| 1077 | Linoleic acid | 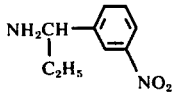 | | 180 | 24 | 25 " 1.5155 | 73.26 | 73.55 | 9.56 | 9.70 | 6.33 | 6.17 |
| 1078 | Linoleic acid | 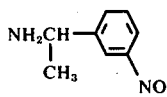 | Boric acid 5% | 160 | 12 | 23 " 1.5111 | 72.86 | 73.06 | 9.41 | 9.68 | 6.54 | 6.31 |
| 1079 | Isostearic acid | 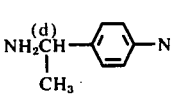 | | 160 | 37 | 23.5" 1.5158 | 72.18 | 72.40 | 10.25 | 10.33 | 6.48 | 6.40 |
| 1080 | Isostearic acid | 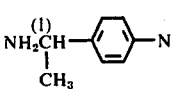 | | 145 | 39 | 24.5" 1.5156 | 72.18 | 72.39 | 10.25 | 10.46 | 6.48 | 6.41 |
| 1081 | Safflower oil acid | 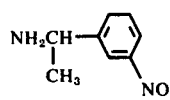 | | 160 | 36 | 24° C 1.5137 | | | | | | |
| 1082 | Soybean oil acid | 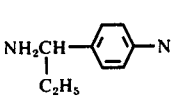 | | 180 | 28 | 26 " 1.5124 | | | | | | |
| 1083 | Sesame oil acid | 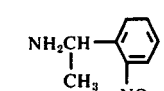 | | 180 | 24 | 26 " 1.5104 | | | | | | |
| 1084 | Castor oil acid | 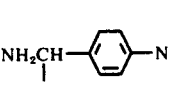 | | 170 | 24 | 25.5" 1.5119 | | | | | | |
| 1085 | Corn oil acid | 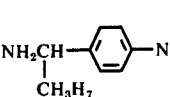 | | 165 | 34 | 23.5" 1.5114 | | | | | | |
| 1086 | Cottonseed oil acid | 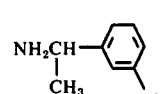 | | 160 | 34 | 24.5" 1.5128 | | | | | | |
| 1087 | Olive oil acid | 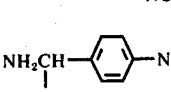 | | 160 | 36 | 23.5" 1.5129 | | | | | | |
| 1088 | Linseed oil acid | 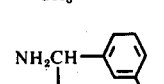 | | 160 | 34 | 22.5" 1.5120 | | | | | | |

-continued

| Ex. No. | Acid | Amine | Agent | Reaction temperature °C. | Reaction time (hr) | $n_D$ | C% Theoretical | C% Analytical | H% Theoretical | H% Analytical | N% Theoretical | N% Analytical |
|---|---|---|---|---|---|---|---|---|---|---|---|---|
| 1089 | Rapeseed oil acid | NH₂CH(CH₃)-C₆H₄-NO₂ (m) | Boric acid 5% | 160 | 10 | 23" 1.5140 | | | | | | |
| 1090 | Rice bran oil acid | NH₂CH(CH₃)-C₆H₄-NO₂ (p) | | 160 | 32 | 23" 1.5122 | | | | | | |
| 1091 | Chrysalis oil acid | NH₂CH(CH₃)-C₆H₄-NO₂ (p) | | 160 | 32 | 23" 1.5110 | | | | | | |
| 1092 | Flatfish oil acid | NH₂CH(C₂H₅)-C₆H₄-NO₂ (p) | | 160 | 32 | 21" 1.5122 | | | | | | |
| 1093 | Sark oil acid | NH₂CH(CH₃)-C₆H₄-NO₂ (m) | | 160 | 32 | 22" 1.5140 | | | | | | |
| 1094 | Whale oil acid | NH₂CH(CH₃)-C₆H₄-NO₂ (p) | | 160 | 37 | 21" 1.5131 | | | | | | |
| 1095 | Cuttlefish oil acid | NH₂CH(CH₃)-C₆H₄-NO₂ (m) | | 160 | 32 | 23.5" 1.5130 | | | | | | |
| 1096 | Sardine oil acid | NH₂CH(CH₃)-C₆H₄-NO₂ (m) | | 160 | 32 | 21.5" 1.5222 | | | | | | |
| 1097 | Mackerel oil acid | NH₂CH(CH₃)-C₆H₄-NO₂ (p) | | 145 | 37 | 18.5" 1.5152 | | | | | | |
| 1098 | Saurypike oil acid | NH₂CH(CH₃)-C₆H₄-NO₂ (m) | | 145 | 34 | 19" 1.5157 | | | | | | |
| 1099 | Herring oil acid | NH₂CH(CH₃)-C₆H₄-NO₂ (m) | | 145 | 34 | 20" 1.5120 | | | | | | |
| 1100 | Saurel oil acid | NH₂CH(CH₃)-C₆H₄-NO₂ (o) | | 160 | 34 | 20.5" 1.5150 | | | | | | |
| 1101 | Menhaden oil acid | NH₂CH(CH₃)-C₆H₄-NO₂ (p) | | 145 | 35 | 22.5" 1.5160 | | | | | | |
| 1102 | Cod oil acid | NH₂CH(CH₃)-C₆H₄-NO₂ (m) | | 145 | 37 | 20" 1.5150 | | | | | | |

| Ex. No. | Acid | Amine | Agent | Reaction temperature °C. | Reaction time (hr) | $n_D$ | C% Theoretical | C% Analytical | H% Theoretical | H% Analytical | N% Theoretical | N% Analytical |
|---|---|---|---|---|---|---|---|---|---|---|---|---|
| 1103 | Liver oil acid | NH₂CH(CH₃)–C₆H₄–NO₂ | | 160 | 37 | 20″ 1.5210 | | | | | | |
| 1104 | Menuke oil acid | NH₂CH(CH₃)–C₆H₄–NO₂ | | 160 | 37 | 19″ 1.5133 | | | | | | |
| 1105 | Residual oil acid | NH₂CH(CH₃)–C₆H₄–NO₂ | Boric acid 10% | 160 | 10 | 18.5″ 1.5142 | | | | | | |

EXAMPLE 1106

A mixture of 10 g. of methyl linoleate and 10 g. of α-methyl-p-nitrobenzylamine was heated in a nitrogen atmosphere at 180° C. for 30 hours removing methanol. The same treatments as in Example 857 were effected to obtain 12.8 g. of a desired product, $n_D^{28}$ 1.5106. Elementary analysis:

| | Theoretical | Analytical |
|---|---|---|
| C (%) | 72.86 | 73.06 |
| H (%) | 9.41 | 9.62 |
| N (%) | 6.54 | 6.30 |

EXAMPLE 1107

A mixture of 10 g. of methyl isostearate, 10 g. of α-methyl-p-nitrobenzylamine and 1 g. of sodium methylate was heated at 150° for 3 hours removing methanol. The reaction product was washed with acid, alkali and water according to ordinary procedures and was then dried to obtain 12.3 g. of a desired product, $n_D^{28}$ 1.5063. Elementary analysis:

| | Theoretical | Analytical |
|---|---|---|
| C (%) | 72.18 | 72.24 |
| H (%) | 10.25 | 10.28 |

-continued

| | Theoretical | Analytical |
|---|---|---|
| N (%) | 6.48 | 6.52 |

EXAMPLE 1108

To a mixture of 10 g. of ethyl oleate and 9 g. of α-methyl-p-nitrobenzylamine was added a solution of 0.5 g. of sodium in 8 ml. of ethyl alcohol. The mixture was heated at 160° for about 2 hours removing ethyl alcohol. Thereafter, the same treatments as in Example 857 were effected to obtain 12.8 g. of a desired product, $n_D^{22}$ 1.5150. Elementary analysis:

| | Theoretical | Analytical |
|---|---|---|
| C (%) | 72.52 | 72.77 |
| H (%) | 9.83 | 9.99 |
| N (%) | 6.51 | 6.30 |

EXAMPLE 1109

A mixture of 10 g. of safflower oil and 10 g. of α-methyl-p-nitrobenzylamine was heated in an autoclave at 200° C. for 12 hours, and 13.0 g. of a desired product, $n_D^{28}$ 1.5140 was obtained.

Examples 1110–1164 are shown in the following table:

| Ex. No. | RCOA (A) Acid | Amine | Agent | Reaction temperature °C. | Reaction time (hr) | $n_D$ | C% Theoretical | C% Analytical | H% Theoretical | H% Analytical | N% Theoretical | N% Analytical |
|---|---|---|---|---|---|---|---|---|---|---|---|---|
| 1110 | Oleic acid (OCH₃) | NH₂CH(C₂H₅)–C₆H₄–NO₂ | t-C₄H₉OK | 180 | 4 | 22° C 1.5122 | 72.93 | 73.21 | 9.97 | 10.05 | 6.30 | 6.11 |
| 1111 | Linolenic acid (OCH₃) | NH₂CH(C₂H₅)–C₆H₄–NO₂ | | 160 | 37 | 22° C 1.5000 | 73.60 | 73.88 | 9.15 | 9.41 | 6.36 | 6.24 |

-continued

| Ex. No. | RCOA (A) Acid | Amine | Agent | Reaction temperature °C. | Reaction time (hr) | Reaction $n_D$ | C % Theoretical | C % Analytical | H % Theoretical | H % Analytical | N % Theoretical | N % Analytical |
|---|---|---|---|---|---|---|---|---|---|---|---|---|
| 1112 | Linoleic acid (OCH₃) | 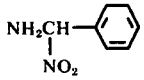 | | 160 | 37 | 23.5° C 1.5157 | 73.26 | 73.61 | 9.56 | 9.76 | 6.33 | 6.19 |
| 1113 | Linoleic acid (OCH₃) | 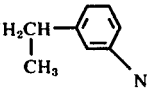 | Boric-acid 5 % | 160 | 12 | 22° C 1.5114 | 72.86 | 73.04 | 9.41 | 9.60 | 6.54 | 6.47 |
| 1114 | Isostearic acid (OCH₃) | 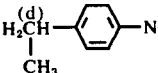 | | 160 | 40 | 24° C 1.5149 | 72.18 | 72.33 | 10.25 | 10.50 | 6.48 | 6.43 |
| 1115 | Isostearic acid (OCH₃) | 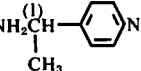 | | 160 | 40 | 24° C 1.5156 | 72.18 | 72.41 | 10.25 | 10.54 | 6.48 | 6.41 |
| 1116 | Safflower oil acid (OCH₃) | 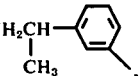 | | 160 | 40 | 24° C 1.5135 | | | | | | |
| 1117 | Soybean oil acid (OCH₃) | 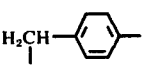 | | 180 | 40 | 24° C 1.5122 | | | | | | |
| 1118 | Sesame oil acid (OC₂H₅) | 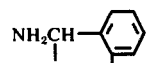 | | 170 | 35 | 24° C 1.5096 | | | | | | |
| 1119 | Castor oil acid (OCH₃) | 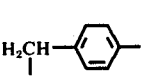 | | 180 | 35 | 24° C 1.5120 | | | | | | |
| 1120 | Corn oil acid (OCH₃) | 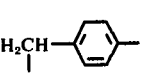 | | 180 | 35 | 25.5° C 1.5116 | | | | | | |
| 1121 | Cottonseed oil acid (OCH₃) | 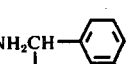 | | 180 | 35 | 26° C 1.5126 | | | | | | |
| 1122 | Olive oil acid (OCH₃) | 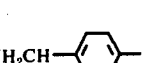 | | 180 | 35 | 26° C 1.5122 | | | | | | |
| 1123 | Linseed oil acid (OC₂H₅) | 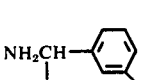 | | 160 | 42 | 24° C 1.5120 | | | | | | |
| 1124 | Rapeseed oil acid (OCH₃) | 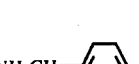 | | 160 | 42 | 24° C 1.5134 | | | | | | |
| 1125 | Rice bran oil acid (OCH₃) | 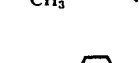 | | 160 | 42 | 24° C 1.5120 | | | | | | |
| 1126 | Chrysalis oil acid (OCH₃) | 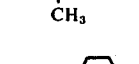 | | 160 | 42 | 24.5° C 1.5116 | | | | | | |

-continued

| Ex. No. | RCOA (A) Acid | Amine | Agent | Reaction temperature °C. | Reaction time (hr) | Reac- $n_D$ | C % Theoretical | C % Analytical | H % Theoretical | H % Analytical | N % Theoretical | N % Analytical |
|---|---|---|---|---|---|---|---|---|---|---|---|---|
| 1127 | Flatfish oil acid (OCH₃) | NH₂CH(C₂H₅)−C₆H₄−NO₂ | | 160 | 40 | 22° C 1.5123 | | | | | | |
| 1128 | Shark oil acid (OCH₃) | NH₂CH(CH₃)−C₆H₄−NO₂ (m) | | 160 | 37 | 23° C 1.5142 | | | | | | |
| 1129 | Whale oil acid (OCH₃) | NH₂CH(CH₃)−C₆H₄−NO₂ | | 160 | 37 | 23° C 1.5132 | | | | | | |
| 1130 | Cuttlefish oil acid (OCH₃) | NH₂CH(CH₃)−C₆H₄−NO₂ | | 160 | 37 | 23° C 1.5129 | | | | | | |
| 1131 | Sardine oil acid (OCH₃) | NH₂CH(CH₃)−C₆H₄−NO₂ | | 160 | 40 | 25° C 1.5220 | | | | | | |
| 1132 | Maclerel oil acid (OCH₃) | NH₂CH(CH₃)−C₆H₄−NO₃ | | 160 | 40 | 23.5° C 1.5144 | | | | | | |
| 1133 | Saury pike oil acid (OCH₃) | NH₂CH(CH₃)−C₆H₄−NO₂ | | 160 | 40 | 23° C 1.5147 | | | | | | |
| 1134 | Herring oil acid (OCH₃) | NH₂CH(CH₃)−C₆H₄−NO₂ | | 160 | 40 | 23° C 1.5120 | | | | | | |
| 1135 | Saurel oil acid (OCH₃) | NH₂CH(CH₃)−C₆H₄−NO₂ | Boric-acid | 160 | 12 | 23° C 1.5146 | | | | | | |
| 1136 | Menhaden oil acid (OCH₃) | NH₂CH(CH₃)−C₆H₄−NO₂ | | 160 | 40 | 23° C 1.5157 | | | | | | |
| 1137 | Cod oil acid (OCH₃) | NH₂CH(CH₃)−C₆H₄−NO₂ | | 160 | 40 | 22.5° C 1.5141 | | | | | | |
| 1138 | Liver oil acid (OCH₃) | NH₂CH(CH₃)−C₆H₄−NO₂ | | 160 | 40 | 23° C 1.5218 | | | | | | |
| 1139 | Menuke oil acid (OCH₃) | NH₂CH(CH₃)−C₆H₄−NO₂ | | 160 | 40 | 24° C 1.5129 | | | | | | |
| 1140 | Residual oil acid (OCH₃) | NH₂CH(C₂H₅)−C₆H₄−NO₂ | | 160 | 40 | 25° C 1.5133 | | | | | | |

-continued

| Ex. No. | RCOA (A) Acid | Amine | Agent | Reaction temperature °C. | Reaction time (hr) | Reaction $n_D$ | C % Theoretical | C % Analytical | H % Theoretical | H % Analytical | N % Theoretical | N % Analytical |
|---|---|---|---|---|---|---|---|---|---|---|---|---|
| 1141 | Soybean oil | 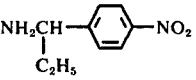 | | 160 | 42 | 23° C 1.5129 | | | | | | |
| 1142 | Sesame oil | 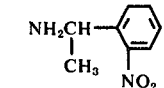 | | 160 | 40 | 23° C 1.5109 | | | | | | |
| 1143 | Castor oil | 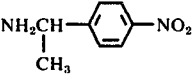 | Boric-acid 5 % | 170 | 40 | 24° C 1.5122 | | | | | | |
| 1144 | Corn oil | 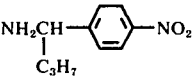 | | 180 | 30 | 23° C 1.5120 | | | | | | |
| 1145 | Cottonseed oil | 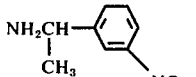 | | 160 | 40 | 24° C 1.5128 | | | | | | |
| 1146 | Olive oil | 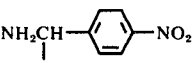 | | 160 | 40 | 23° C 1.5124 | | | | | | |
| 1147 | Linseed oil | 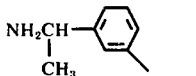 | | 160 | 40 | 23° C 1.5123 | | | | | | |
| 1148 | Rapeseed oil | 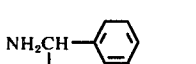 | * | 200 | 20 | 24° C 1.5122 | | | | | | |
| 1149 | Rice bran oil | 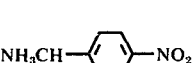 | | 160 | 36 | 23° C 1.5133 | | | | | | |
| 1150 | Chrysalis oil | 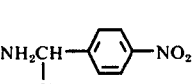 | | 160 | 36 | 23° C 1.5120 | | | | | | |
| 1151 | Flatfish oil | 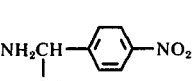 | | 160 | 40 | 23° C 1.5122 | | | | | | |
| 1152 | Shark oil | 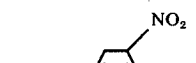 | | 160 | 40 | 22° C 1.5139 | | | | | | |
| 1153 | Whale oil |  | | 170 | 40 | 22° C 1.5128 | | | | | | |
| 1154 | Cuttlefish oil |  | * | 200 | 8 | 23° C 1.5133 | | | | | | |
| 1155 | Sardine oil | 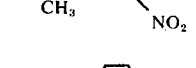 | | 170 | 40 | 23° C 1.5232 | | | | | | |

| Ex. No. | RCOA (A) Acid | Amine | Agent | Reaction temperature °C. | Reaction time (hr) | Reac- nD | C % Theoretical | C % Analytical | H % Theoretical | H % Analytical | N % Theoretical | N % Analytical |
|---|---|---|---|---|---|---|---|---|---|---|---|---|
| 1156 | Mackerel oil | 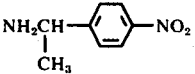 | | 170 | 40 | 24° C 1.5139 | | | | | | |
| 1157 | Saury-pike oil | 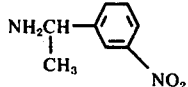 | | 170 | 40 | 24° C 1.5146 | | | | | | |
| 1158 | Herring oil | 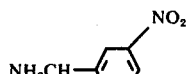 | | 170 | 37 | 24° C 1.5120 | | | | | | |
| 1159 | Saurel oil | 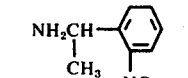 | | 170 | 36 | 25° C 1.5145 | | | | | | |
| 1160 | Menhaden oil | 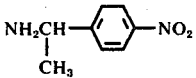 | | 170 | 37 | 25° C 1.5155 | | | | | | |
| 1161 | Cod oil | 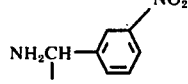 | | 160 | 40 | 23° C 1.5140 | | | | | | |
| 1162 | Liver oil | 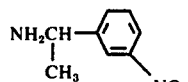 | | 160 | 40 | 24° C 1.5220 | | | | | | |
| 1163 | Menuke oil | 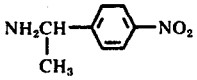 | | 170 | 35 | 25° C 1.5127 | | | | | | |
| 1164 | Residual oil | 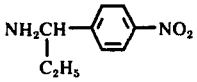 | | 170 | 35 | 24° C 1.5130 | | | | | | |

*In an autoclave

EXAMPLE 1165

To a mixture of 150 g. of α-methyl-p-nitrobenzylamine, 100 ml. of anhydrous ether and 8 g. of trimethylamine was added a solution of 30 g. of linoleic acid chloride in 50 ml. of anhydrous ether, under stirring at 0°–5° C. The reaction mixture was boiled for 2 hours after addition. Subsequently, the ether solution of the reaction product was washed with acid, alkali and water to obtain 38.2 g. of a desired product, b.p. 209°–218° C./0.05 mmHg, $n_D^{26}$ 1.5120. Elementary analysis:

| | Theoretical | Analytical |
|---|---|---|
| C (%) | 72.86 | 73.06 |
| H (%) | 9.41 | 9.66 |
| N (%) | 6.54 | 6.28 |

Examples 1166–1196 are shown in the following table:

| Ex. No. | RCOA (A) Acid | | Amine | Agent | Solvent | $n_D$ | C % Theoretical | C % Analytical | H % Theoretical | H % Analytical | N % Theoretical | N % Analytical |
|---|---|---|---|---|---|---|---|---|---|---|---|---|
| 1166 | Oleic acid | (Cl) |  | Sodium-carbonate | Water-acetone | 23° C 1.5120 | 72.93 | 73.20 | 9.97 | 10.01 | 6.30 | 6.19 |
| 1167 | Linolenic acid | (Cl) |  | Pyridine | Tetrahydrofuran | 23" 1.5005 | 73.60 | 73.79 | 9.15 | 9.40 | 6.36 | 6.23 |
| 1168 | Linoleic acid | (Cl) |  | Sodium-carbonate | Water-tetrahydrofuran | 21.5" 1.5155 | 73.26 | 73.56 | 9.56 | 9.72 | 6.33 | 6.19 |
| 1169 | Linoleic acid | (Cl) |  | Sodium hydroxide | Water-dioxane | 21" 1.5116 | 72.86 | 72.94 | 9.41 | 9.63 | 6.54 | 6.47 |
| 1170 | Isostearic acid | (Cl) |  | Pyridine | Ether | 20" 1.5152 | 72.18 | 72.32 | 10.25 | 10.51 | 6.48 | 6.46 |
| 1171 | Isostearic acid | (Cl) |  | Picoline | Benzene | 23" 1.5160 | 72.18 | 72.31 | 10.25 | 10.49 | 6.48 | 6.32 |
| 1172 | Safflower oil acid | (Cl) |  | Trimethylamine | Benzene | 24" 1.5137 | | | | | | |
| 1173 | Soybean oil acid | (Cl) |  | Triethylamine | Ether | 20" 1.5123 | | | | | | |
| 1174 | Sesame oil acid | (Cl) |  | Dimethylamine | Benzene | 24" 1.5094 | | | | | | |
| 1175 | Castor oil acid | (Cl) |  | Potassium hydroxide | Water-tetrahydrofuran | 23" 1.5121 | | | | | | |
| 1176 | Corn oil acid | (Cl) |  | Potassium hydroxide | Water-dioxane | 22" 1.5115 | | | | | | |
| 1177 | Cottonseed oil acid | (Cl) |  | Sodium carbonate | Water-acetone | 22" 1.5130 | | | | | | |
| 1178 | Olive oil acid | (Cl) |  | Sodium carbonate | Methylisobutylketone | 23" 1.5123 | | | | | | |
| 1179 | Linseed oil acid | (Cl) |  | Pyridine | Ether | 24" 1.5119 | | | | | | |
| 1180 | Rapeseed oil acid | (Cl) |  | Trimethylamine | Ether | 23" 1.5134 | | | | | | |

-continued

| Ex. No. | RCOA (A) Acid | Amine | Agent | Solvent | $n_D$ | C % Theoretical | C % Analytical | H % Theoretical | H % Analytical | N % Theoretical | N % Analytical |
|---|---|---|---|---|---|---|---|---|---|---|---|
| 1181 | Rice bran oil acid (Cl) | NH₂CH(CH₃)-C₆H₄-NO₂ | Trimethylamine | Benzene | 24″ 1.5119 | | | | | | |
| 1182 | Chrysalis oil acid (Cl) | NH₂CH(CH₃)-C₆H₄-NO₂ | Pyridine | Benzene | 22″ 1.5118 | | | | | | |
| 1183 | Flatfish oil acid (Cl) | NH₂CH(C₂H₅)-C₆H₄-NO₂ | Pyridine | Tetrahydrofuran | 22″ 1.5120 | | | | | | |
| 1184 | Shark oil acid (Cl) | NH₂CH(CH₃)-C₆H₄-NO₂ | Picoline | Benzene | 20″ 1.5138 | | | | | | |
| 1185 | Whale oil acid (Cl) | NH₂CH(CH₃)-C₆H₄-NO₂ | Lutidine | Toluene | 21″ 1.5128 | | | | | | |
| 1186 | Cuttlefish oil acid (Cl) | NH₂CH(CH₃)-C₆H₄-NO₂ | Trimethylamine | Ether | 22° C 1.5130 | | | | | | |
| 1187 | Sardine oil acid (Cl) | NH₂CH(CH₃)-C₆H₄-NO₂ | Potassium carbonate | Acetone | 23″ 1.5221 | | | | | | |
| 1188 | Mackerel oil acid (Cl) | NH₂CH(CH₃)-C₆H₄-NO₂ | Pyridine | Benzene | 24″ 1.5146 | | | | | | |
| 1189 | Saury-pike oil acid (Cl) | NH₂CH(CH₃)-C₆H₄-NO₂ | Pyridine | Acetone | 22″ 1.5149 | | | | | | |
| 1190 | Herring oil acid (Cl) | NH₂CH(CH₃)-C₆H₄-NO₂ | Potassium carbonate | Acetone | 24″ 1.5118 | | | | | | |
| 1191 | Saurel oil acid (Cl) | NH₂CH(CH₃)-C₆H₄-NO₂ | Pyridine | Benzene | 24″ 1.5139 | | | | | | |
| 1192 | Menhaden oil acid (Cl) | NH₂CH(CH₃)-C₆H₄-NO₂ | Potassium carbonate | Acetone | 23″ 1.5159 | | | | | | |
| 1193 | Cod oil acid (Cl) | NH₂CH(CH₃)-C₆H₄-NO₂ | Trimethylamine | Toluene | 22″ 1.5139 | | | | | | |
| 1194 | Liver oil acid (Cl) | NH₂CH(CH₃)-C₆H₄-NO₂ | Sodium hydroxide | Water-dioxane | 23″ 1.5220 | | | | | | |
| 1195 | Menuke oil acid (Cl) | NH₂CH(CH₃)-C₆H₄-NO₂ | Potassium carbonate | Methylisobutyl-ketone | 22″ 1.5130 | | | | | | |

| Ex. No. | RCOA (A) Acid | Amine | Agent | Solvent | $n_D$ | C % Theoretical | C % Analytical | H % Theoretical | H % Analytical | N % Theoretical | N % Analytical |
|---|---|---|---|---|---|---|---|---|---|---|---|
| 1196 | Residual oil acid (Cl) | NH₂CH(CH₃)-C₆H₄-NO₂ | | Pyridine Ether | 24″ 1.5135 | | | | | | |

EXAMPLE 1196

Isostearic acid (34.4 g.) and 9.9 g. of cyclohexylamine were individually dissolved in 30 ml. of dioxane. The solutions were added with stirring at room temperature to a solution of 26.1 g. of dicyclohexyl carbodiimide in 30 ml. of dioxane, and the mixed solution was allowed to stand at room temperature for 8 hours. The solution was charged with 5 ml. of acetic acid and was again allowed to stand for additional 2 hours. Thereafter, dicyclohexylurea was separated by filtration and the filtrate was concentrated. The residue was dissolved in 100 ml. of ether and the ether solution was washed with 5% HCl, 5% NaOH and water, and was then dried over anhydrous sodium sulfate and concentrated and distilled to obtain 36.2 g. of a desired product, b.p. 200°–207° C./0.07 mmHg. Elementary analysis:

|  | Theoretical | Analytical |
|---|---|---|
| C (%) | 78.84 | 79.04 |
| H (%) | 12.96 | 12.63 |
| N (%) | 3.83 | 3.79 |

Examples 1197–1238 are shown in the following table:

| Example No. | Amine | B Condensing Agent BB=C=NB | Solvent | C % Theoretical | C % Analytical | H % Theoretical | H % Analytical | N % Theoretical | N % Analytical |
|---|---|---|---|---|---|---|---|---|---|
| 1197 | NH₂—CH(CH₃)₂ | cyclohexyl | Ether | 77.48 | 77.29 | 13.32 | 13.09 | 4.30 | 4.35 |
| 1198 | NH(CH₃)₂ | cyclohexyl | Ether | 77.10 | 76.83 | 13.27 | 13.08 | 4.50 | 4.48 |
| 1199 | NH₂CH₂CH=CH₂ | cyclohexyl | Ether | 77.95 | 77.77 | 12.77 | 12.57 | 4.33 | 4.16 |
| 1200 | NH(CH₂CH=CH₂)₂ | cyclohexyl | Tetrahydrofuran | 79.27 | 78.94 | 12.47 | 12.09 | 3.85 | 3.67 |
| 1201 | NH₂-cyclopentyl | cyclohexyl | Dioxane | 78.56 | 78.31 | 12.90 | 12.76 | 3.98 | 3.79 |
| 1202 | NH₂-cycloheptyl | cyclohexyl | Dioxane | 79.09 | 78.73 | 13.01 | 12.84 | 3.69 | 3.44 |
| 1203 | NH₂-(2-methylcyclohexyl) | cyclohexenyl | Benzene | 79.09 | 79.41 | 13.01 | 12.76 | 3.69 | 3.87 |
| 1204 | NH₂-C₆H₁₀-OH | cyclohexyl | Ligroin | 75.53 | 75.04 | 12.41 | 12.26 | 3.67 | 3.65 |
| 1205 | NH₂-C₆H₁₀-OCH₃ | cyclohexyl | Toluene | 75.89 | 75.53 | 12.48 | 12.28 | 3.54 | 3.16 |

-continued

| Example No. | Amine | B Condensing Agent BB=C=NB | Solvent | C % Theoretical | C % Analytical | H % Theoretical | H % Analytical | N % Theoretical | N % Analytical |
|---|---|---|---|---|---|---|---|---|---|
| 1206 | (C6H5)2NH | cyclohexyl | Dioxane | 82.70 | 82.98 | 10.41 | 10.33 | 3.22 | 3.09 |
| 1207 | 2-CH3-C6H4-NH2 | —CH(CH3)2 | Benzene | 80.37 | 80.17 | 11.60 | 11.49 | 3.75 | 3.48 |
| 1208 | 4-(C(CH3)3)-C6H4-NH2 | cyclohexyl | Dioxane-Pyridine | 80.90 | 81.05 | 11.88 | 11.56 | 3.37 | 3.02 |
| 1209 | 4-HO-C6H4-NH2 | cyclohexyl | Dioxane | 80.15 | 79.78 | 11.49 | 11.22 | 3.90 | 3.77 |
| 1210 | 2-CH3-6-Cl-C6H3-NH2 | cyclohexyl | Ligroin | 73.61 | 72.30 | 10.30 | 10.08 | 3.43 | 3.40 |
| 1211 | 4-F-C6H4-NH2 | cyclohexyl | Acetone | 76.39 | 76.59 | 10.61 | 10.23 | 3.71 | 3.69 |
| 1212 | 4-Br-C6H4-NH2 | cyclohexyl | Benzene | 65.75 | 65.49 | 9.13 | 9.06 | 3.19 | 3.00 |
| 1213 | 4-CF3-C6H4-NH2 | cyclohexyl | Tetrahydrofuran | 70.25 | 70.06 | 9.36 | 9.08 | 3.27 | 3.06 |
| 1214 | 4-CH3O-C6H10-NH2 | cyclohexyl | Dioxane | 77.07 | 76.83 | 11.13 | 11.00 | 3.60 | 3.33 |
| 1215 | 2-OEt-C6H4-NH2 | cyclohexyl | Toluene | 77.36 | 77.14 | 11.24 | 10.98 | 3.47 | 3.09 |
| 1216 | pyrrolidine | —CH(CH3)2 | Ether | 78.27 | 78.00 | 12.84 | 12.73 | 4.15 | 4.07 |
| 1217 | piperidine | —CH(CH3)2 | Dioxane | 78.56 | 78.24 | 12.90 | 12.71 | 3.98 | 3.78 |
| 1218 | morpholine | cyclohexyl | Tetrahydrofuran | 74.73 | 74.99 | 12.26 | 12.05 | 3.96 | 3.74 |
| 1219 | hexamethyleneimine | cyclohexyl | Benzene | 78.84 | 78.82 | 12.96 | 13.15 | 3.83 | 3.58 |
| 1220 | C6H5-CH2-NH2 | cyclohexyl | Dioxane | 80.37 | 80.05 | 11.60 | 11.40 | 3.75 | 3.36 |

-continued

| Example No. | Amine | B Condensing Agent BB=C=NB | Solvent | C % Theoretical | C % Analytical | H % Theoretical | H % Analytical | N % Theoretical | N % Analytical |
|---|---|---|---|---|---|---|---|---|---|
| 1221 | NH$_2$(CH$_2$—C$_6$H$_5$)$_2$ | cyclohexyl | Chloroform | 82.88 | 83.09 | 10.65 | 10.33 | 3.02 | 3.20 |
| 1222 | NH(—C$_6$H$_{11}$)$_2$ | cyclohexyl | Chloroform | 80.47 | 80.22 | 12.83 | 12.49 | 3.13 | 3.03 |
| 1223 | NH$_2$CH(CH$_3$)—C$_6$H$_5$ | cyclohexyl | Dioxane | 80.56 | 80.19 | 11.70 | 11.46 | 3.61 | 3.39 |
| 1224 | NH$_2$CH(C$_2$H$_5$)—C$_6$H$_5$ | cyclohexyl | Chloroform | 81.14 | 81.04 | 11.35 | 11.05 | 3.51 | 3.46 |
| 1225 | NH$_2$CH$_2$—C$_6$H$_4$—OH | cyclohexyl | Dioxane | 77.07 | 76.87 | 11.13 | 11.02 | 3.60 | 3.48 |
| 1226 | NH$_2$CH$_2$—C$_6$H$_4$(o-CH$_3$) | cyclohexyl | Chloroform | 80.56 | 80.34 | 11.70 | 11.44 | 3.61 | 3.49 |
| 1227 | NH$_2$CH$_2$—C$_6$H$_4$—CH$_3$ | cyclohexyl | Ether | 80.56 | 80.44 | 11.70 | 11.49 | 3.61 | 3.50 |
| 1228 | NH$_2$CH$_2$—C$_6$H$_4$—OCH$_3$ | cyclohexyl | Dioxane | 77.36 | 77.08 | 11.24 | 11.05 | 3.47 | 3.30 |
| 1229 | NH$_2$CH$_2$—C$_6$H$_4$(o-OCH$_3$) | cyclohexyl | Tetrahydrofuran | 77.36 | 77.00 | 11.24 | 11.04 | 3.47 | 3.59 |
| 1230 | NH$_2$—C$_6$H$_{10}$—OC$_2$H$_5$ | cyclohexyl | Toluene | 76.22 | 76.49 | 12.55 | 12.33 | 3.42 | 3.62 |
| 1231 | NH$_2$C$_{12}$H$_{25}$ | cyclohexyl | Benzene | 80.11 | 79.87 | 13.22 | 13.04 | 3.11 | 3.00 |
| 1232 | NH$_2$—C$_6$H$_{10}$—OCH$_3$ | cyclohexyl | Ether | 75.89 | 75.59 | 12.48 | 12.06 | 3.54 | 3.62 |
| 1233 | NH$_2$—C$_6$H$_4$—CF$_3$ | cyclohexyl | Ether | 70.25 | 69.93 | 9.36 | 8.99 | 3.27 | 3.49 |
| 1234 | NH$_2$—CH$_2$—C$_6$H$_4$(o-CH$_3$) | cyclohexyl | Toluene | 80.56 | 80.28 | 11.70 | 11.56 | 3.61 | 3.38 |
| 1235 | NH$_2$CH$_2$—C$_6$H$_4$(o-OH) | cyclohexyl | Tetrahydrofuran | 77.07 | 76.85 | 11.13 | 10.78 | 3.60 | 3.29 |
| 1236 | NH$_2$—C$_6$H$_3$(CH$_3$)(Cl) | cyclohexyl | Benzene | 73.61 | 73.49 | 10.30 | 10.06 | 3.43 | 3.06 |

-continued

| Example No. | Amine | B Condensing Agent BB=C=NB | Solvent | C % Theoretical | C % Analytical | H % Theoretical | H % Analytical | N % Theoretical | N % Analytical |
|---|---|---|---|---|---|---|---|---|---|
| 1237 | NH$_2$—⟨⟩—Cl | ⟨⟩ | Dioxane | 73.18 | 72.94 | 10.16 | 10.00 | 3.55 | 3.50 |

EXAMPLE 1238

A mixture of 10 g. of isostearic acid, 5 g. of cyclohexylamine, 0.2 g. of p-toluenesulfonic acid and 100 ml. of toluene was heated for 8 hours using a water separator. The reaction product was treated according to ordinary procedures to obtain 12.3 g. of a desired product, b.p. 200°–204° C./0.06 mmHg. Elementary analysis:

|  | Theoretical | Analytical |
|---|---|---|
| C (%) | 78.84 | 79.06 |
| H (%) | 12.96 | 12.83 |
| N (%) | 3.83 | 3.78 |

EXAMPLE 1239

To a solution of 14.2 g. of isostearic acid and 5.5 g. of triethylamine in 100 cc. of tetrahydrofuran was added 5.9 g. of ethyl chloroformate under stirring at −10° to −5° C. The stirring was continued at −5° C. for additional 20 minutes. Subsequently, 6.0 g. of α-methylbenzylamine was added dropwise with stirring at −5° C. After the addition, the cooling both was removed and the temperature was gradually elevated and the stirring was continued. Thereafter, the temperature was gradually increased and the reaction mixture was stirred at 40° C. for 20 minutes. After cooling, the tetrahydrofuran was distilled off in vacuo and the residue was dissolved in ether. The ether solution was washed with cold dilute hydrochloric acid, cold sodium carbonate water and water, and was then dried with anhydrous sodium carbonate. The ether was removed by distillation and the residue was distilled in vacuo to obtain 15.5 g. of a desired product, b.p. 200°–207° C./0.02 mmHg. Elementary analysis:

|  | Theoretical | Analytical |
|---|---|---|
| C (%) | 80.56 | 80.71 |
| H (%) | 11.70 | 11.70 |
| N (%) | 3.61 | 3.58 |

Examples 1240–1307 are shown in the following table:

| Example No. | Amine | b.p. °C./mmHg. | Theoretical | Analytical | Theoretical | Analytical | Theoretical | Analytical |
|---|---|---|---|---|---|---|---|---|
| 1240 | NH$_2$CH(CH$_3$)$_2$ (CH$_3$, CH$_3$) | 190–205/0.03 | 77.48 | 77.57 | 13.32 | 13.64 | 4.30 | 4.25 |
| 1241 | NH$_2$C$_{12}$H$_{25}$ | Semi-solid | 60.11 | 80.25 | 13.22 | 13.42 | 3.11 | 3.05 |
| 1242 | NH$_2$CH$_2$—CH=CH$_2$ | 192–199/0.04 | 77.95 | 78.20 | 12.77 | 12.89 | 4.33 | 4.07 |
| 1243 | NH(CH$_3$)$_2$ | 188–194/0.04 | 77.10 | 77.25 | 13.27 | 13.42 | 4.50 | 4.46 |
| 1244 | NH(CH$_2$—CH=CH$_2$)$_2$ | 192–203/0.02 | 79.27 | 79.44 | 12.47 | 12.54 | 3.85 | 3.68 |
| 1245 | NH$_2$—⟨cyclopentyl⟩ | 200–208/0.06 | 78.58 | 78.63 | 12.90 | 13.00 | 3.98 | 3.89 |
| 1246 | NH$_2$—⟨cyclohexyl⟩ | 200–204/0.06 | 78.84 | 78.95 | 12.96 | 13.04 | 5.83 | 3.89 |
| 1247 | NH$_2$—⟨cycloheptyl, 7⟩ | 202–207/0.05 | 79.09 | 79.20 | 13.01 | 13.43 | 3.69 | 3.52 |
| 1255 | CH$_3$O—⟨⟩—NH$_2$ | 202–210/0.04 | 75.89 | 75.94 | 12.48 | 12.55 | 3.54 | 3.54 |
| 1256 | NH$_2$—⟨⟩—OCH$_3$ (ortho) | 203–212/0.05 | 75.89 | 75.95 | 12.48 | 12.58 | 3.54 | 3.45 |
| 1257 | NH$_2$—⟨⟩—OCH$_3$ | 202–209/0.05 | 75.89 | 76.04 | 12.48 | 12.64 | 3.54 | 3.49 |
| 1258 | NH$_2$—⟨⟩—OC$_2$H$_5$ | 200–214/0.07 | 76.22 | 76.14 | 12.55 | 12.63 | 3.42 | 3.40 |

-continued

| Example No. | Amine | b.p. °C./mmHg. | Theoretical | Analytical | Theoretical | Analytical | Theoretical | Analytical |
|---|---|---|---|---|---|---|---|---|
| 1259 | CH₃-cyclohexyl-NH₂ (2-methyl) | 204–210/0.06 | 80.37 | 80.42 | 11.60 | 11.58 | 3.75 | 3.52 |
| 1260 | CH₃-cyclohexyl-NH₂ (3-methyl) | 202–218/0.05 | 80.37 | 80.53 | 11.60 | 11.69 | 3.75 | 3.73 |
| 1261 | NH₂-cyclohexyl-CH₃ | 202–207/0.05 | 80.37 | 80.38 | 11.60 | 11.78 | 3.75 | 3.55 |
| 1262 | NH₂-cyclohexyl-C(CH₃)₃ | 205–214/0.06 | 80.90 | 81.16 | 11.88 | 11.98 | 3.37 | 3.38 |
| 1263 | HO-phenyl-NH₂ | 210–215/0.06 | 80.15 | 80.29 | 11.49 | 11.64 | 3.90 | 3.84 |
| 1264 | NH₂-phenyl-OH | 211–217/0.05 | 80.15 | 80.37 | 11.49 | 11.58 | 3.90 | 3.88 |
| 1265 | Cl-phenyl-NH₂ | 205–214/0.07 | 73.18 | 73.44 | 10.16 | 10.27 | 3.55 | 3.49 |
| 1266 | Cl-phenyl-NH₂ | 204–218/0.06 | 73.18 | 73.07 | 10.16 | 10.32 | 3.55 | 3.46 |
| 1267 | NH₂-phenyl-Cl | 202–214/0.06 | 73.18 | 73.21 | 10.16 | 10.54 | 3.55 | 3.39 |
| 1268 | Br-phenyl-NH₂ | 204–208/0.06 | 65.75 | 65.85 | 9.13 | 9.29 | 3.19 | 3.08 |
| 1269 | NH₂-phenyl-F | 199–204/0.04 | 76.39 | 76.48 | 10.61 | 10.88 | 3.71 | 3.52 |
| 1270 | Cl-phenyl-NH₂-CH₃ | 204–214/0.05 | 73.61 | 73.80 | 10.30 | 10.52 | 3.43 | 3.36 |
| 1271 | NH₂-phenyl-CF₃ | 202–208/0.04 | 70.25 | 70.45 | 9.36 | 9.62 | 3.27 | 3.19 |
| 1272 | NH₂-phenyl-CF₃ | 208–214/0.03 | 70.25 | 70.40 | 9.36 | 9.48 | 3.25 | 3.05 |
| 1273 | NH₂-phenyl-Cl | 206–214/0.06 | 73.61 | 73.87 | 10.30 | 10.45 | 3.43 | 3.38 |
| 1274 | cyclohexyl-NH-CH₃ | 200–213/0.05 | 79.09 | 79.30 | 13.01 | 13.07 | 3.69 | 3.56 |
| 1275 | phenyl-NH-phenyl | 204–223/0.05 | 82.70 | 82.65 | 10.41 | 10.65 | 3.22 | 3.18 |
| 1276 | CH₃O-phenyl-NH₂ | 203–208/0.05 | 77.07 | 77.14 | 11.13 | 11.24 | 3.63 | 5.58 |

-continued

| Example No. | Amine | b.p. °C./mmHg. | Theoretical | Analytical | Theoretical | Analytical | Theoretical | Analytical |
|---|---|---|---|---|---|---|---|---|
| 1277 | 3-methoxyaniline (NH₂-C₆H₄-OCH₃) | 201–209/0.05 | 77.07 | 77.18 | 11.13 | 11.28 | 3.60 | 3.42 |
| 1278 | 4-methoxyaniline (NH₂-C₆H₄-OCH₃) | 200–212/0.05 | 77.07 | 77.35 | 11.13 | 11.26 | 3.60 | 3.49 |
| 1279 | 2-ethoxyaniline (OC₂H₅, NH₂) | 204–214/0.04 | 77.36 | 77.41 | 11.24 | 11.65 | 3.47 | 3.46 |
| 1280 | 3-ethoxyaniline (OC₂H₅, NH₂) | 200–220/0.08 | 77.36 | 77.48 | 11.24 | 11.36 | 3.47 | 3.38 |
| 1281 | 4-ethoxyaniline (NH₂-C₆H₄-OC₂H₅) | 199–209/0.08 | 77.36 | 77.45 | 11.24 | 11.28 | 3.47 | 3.24 |
| 1282 | pyrrolidine (HN ring) | 203–208/0.04 | 78.27 | 78.50 | 12.84 | 12.99 | 4.15 | 3.98 |
| 1283 | piperidine (HN ring) | 200–208/0.05 | 78.56 | 78.74 | 12.90 | 13.08 | 3.98 | 3.89 |
| 1284 | hexamethyleneimine (HN 7-ring) | 200–215/0.05 | 78.84 | 78.82 | 12.96 | 13.08 | 3.83 | 3.45 |
| 1285 | morpholine (HN-O ring) | 206–214/0.06 | 74.73 | 74.92 | 12.26 | 12.57 | 3.96 | 3.64 |
| 1286 | benzylamine (NH₂CH₂-C₆H₅) | 201–208/0.05 | 80.37 | 80.64 | 11.60 | 11.84 | 3.75 | 3.50 |
| 1287 | dibenzylamine (NH(CH₂-C₆H₅)₂) | 218–225/0.06 | 82.88 | 82.98 | 10.65 | 10.90 | 3.02 | 3.00 |
| 1288 | α-methylbenzylamine (NH₂CH(CH₃)-C₆H₅) | 201–212/0.05 | 80.56 | 80.75 | 11.70 | 11.92 | 3.61 | 3.38 |
| 1289 | α-ethylbenzylamine (NH₂CH(C₂H₅)-C₆H₅) | 203–208/0.05 | 81.14 | 81.24 | 11.35 | 11.48 | 3.51 | 3.58 |
| 1290 | 2-hydroxybenzylamine (OH, NH₂CH₂-) | 214–219/0.04 | 77.07 | 77.26 | 11.13 | 11.25 | 3.60 | 3.47 |
| 1291 | 4-hydroxybenzylamine (NH₂CH₂-C₆H₄-OH) | 209–219/0.05 | 77.07 | 77.26 | 11.13 | 11.34 | 3.60 | 3.45 |
| 1292 | 2-methoxybenzylamine (OCH₃, NH₂CH-) | 205–217/0.05 | 77.36 | 77.49 | 11.24 | 11.26 | 3.47 | 3.38 |
| 1293 | 3-methoxybenzylamine (OCH₃, NH₂CH₂-) | 205–214/0.04 | 77.36 | 77.50 | 11.24 | 11.37 | 3.47 | 3.37 |
| 1294 | 4-methoxybenzylamine (NH₂CH₂-C₆H₄-OCH₃) | 203–218/0.05 | 77.36 | 77.49 | 11.24 | 11.48 | 3.47 | 3.44 |
| 1295 | 4-ethoxybenzylamine (NH₂CH₂-C₆H₄-OC₂H₅) | 208–218/0.05 | 77.64 | 77.64 | 11.34 | 11.34 | 3.35 | 3.27 |
| 1296 | 3-methylbenzylamine (NH₂CH₂-C₆H₄-CH₃) | 200–215/0.05 | 80.56 | 80.74 | 11.70 | 11.90 | 3.61 | 3.66 |

-continued

| Example No. | Amine | b.p. °C./mmHg. | Theoretical | Analytical | Theoretical | Analytical | Theoretical | Analytical |
|---|---|---|---|---|---|---|---|---|
| 1297 | NH₂CH₂-C₆H₄-CH₃ | 200–208/0.04 | 80.56 | 80.74 | 11.70 | 11.86 | 3.61 | 3.45 |
| 1298 | NH₂CH₂-C₆H₄-CH₃ | 200–205/0.04 | 80.56 | 80.58 | 11.70 | 11.94 | 3.61 | 3.36 |
| 1299 | C₆H₅-NH-CH₃ | 200–218/0.05 | 80.37 | 80.39 | 11.60 | 11.63 | 3.75 | 3.65 |
| 1300 | C₆H₅-NH-C₂H₅ | 201–208/0.02 | 80.73 | 80.82 | 11.80 | 11.94 | 3.49 | 3.15 |
| 1301 | (CH₃)₂-C₆H₃-NH₂-CH₃ | 203–207/0.04 | 80.73 | 80.71 | 11.80 | 12.05 | 3.49 | 3.38 |
| 1302 | NH₂-C₆H₃(CH₃)Cl | 200–218/0.05 | 73.61 | 73.88 | 10.30 | 10.56 | 3.43 | 3.34 |
| 1303 | NH₂-C₆H₃(CH₃)Cl | 200–216/0.05 | 73.61 | 73.74 | 10.30 | 10.49 | 3.43 | 3.36 |
| 1304 | NH₂-C₆H₄-F | 200–214/0.05 | 76.39 | 73.61 | 10.61 | 10.88 | 8.71 | 3.48 |
| 1305 | NH₂-C₆H₄-Br | 200–215/0.05 | 65.75 | 65.86 | 9.13 | 9.23 | 3.19 | 3.47 |
| 1306 | NH₂-C₆H₃(CH₃)Cl | 200–218/0.05 | 73.61 | 73.75 | 10.30 | 10.49 | 3.43 | 3.18 |
| 1307 | NH₂-adamantyl | 215–223/0.06 | 80.51 | 80.78 | 12.31 | 12.40 | 3.35 | 3.06 |

EXAMPLE 1308

To a mixture of 5 g. of cyclohexylamine, 2.5 g. of trimethylamine and 50 ml. of anhydrous ether was added 10 g. of isostearic acid chloride dropwise at 0°–5° C. The reaction mixture was stirred at room temperature for about 10 hours and boiled for 2 hours. Subsequently, the ether layer was washed with acid, alkali and water and was then dried, concentrated and distilled to obtain 11.9 g. of a desired product, b.p. 200°–203° C./0.05 mmHg. Elementary analysis:

|  | Theoretical | Analytical |
|---|---|---|
| C (%) | 77.48 | 77.58 |
| H (%) | 13.32 | 13.41 |
| N (%) | 4.32 | 4.16 |

Examples 1309–1386 are shown in the following table, in which:
Condensation assistant:
a. NaOH
b. KOH
c. Na₂CO₃
d. K₂CO₃
e. Trimethylamine
f. Pyridine
g. Excess amine
h. Anion exchange resin IRA-400
Solvent:
A. Acetone
B. Methylisobutylketone
C. Ether
D. Tetrahydrofuran
E. Dioxane
F. Benzene G. Toluene
H. Water
I. Pyridine

| Ex. No. | Amine | Condensing agent | Solvent | b.p. °C./mmHg | C % Theoretical | C % Analytical | H % Theoretical | H % Analytical | N % Theoretical | N % Analytical |
|---|---|---|---|---|---|---|---|---|---|---|
| 1309 | NH$_2$CH(CH$_3$)$_2$ (isopropyl-like, NH$_2$CH with two CH$_3$) | a | A | 190–203/0.03 | 77.48 | 77.39 | 13.32 | 13.61 | 4.30 | 4.18 |
| 1310 | NH$_2$C$_{12}$H$_{25}$ | g | B | Semisolid | 80.11 | 80.35 | 13.22 | 13.40 | 3.11 | 3.06 |
| 1311 | NH$_2$CH$_2$—C≡CH$_2$ | g | B | 191–199/0.04 | 77.95 | 78.21 | 12.77 | 12.89 | 4.33 | 4.09 |
| 1312 | NH(CH$_3$)$_2$ | g | C | 188–192/0.04 | 77.10 | 77.23 | 13.27 | 13.41 | 4.50 | 4.40 |
| 1313 | NH(CH$_2$—CH=CH$_2$)$_2$ | g | F | 192–208/0.02 | 79.27 | 79.41 | 12.47 | 12.52 | 3.85 | 3.69 |
| 1314 | cyclopentyl-NH$_2$ | | I | 200–204/0.06 | 78.56 | 78.62 | 12.90 | 13.02 | 3.98 | 3.89 |
| 1315 | cyclohexyl-NH$_2$ | g | F | 200–205/0.06 | 78.84 | 78.96 | 12.96 | 13.05 | 3.83 | 3.79 |
| 1316 | cycloheptyl-NH$_2$ | d | B | 202–207/0.05 | 79.09 | 79.21 | 13.01 | 13.42 | 3.69 | 3.32 |
| 1317 | dicyclohexyl-NH | e | C | 210–222/0.05 | 80.47 | 80.61 | 12.83 | 12.93 | 3.13 | 3.09 |
| 1318 | 2-methylcyclohexyl-NH$_2$ | f | I | 202–209/0.05 | 79.09 | 79.31 | 13.01 | 13.21 | 3.69 | 3.50 |
| 1319 | 3-methylcyclohexyl-NH$_2$ | f | I | 204–211/0.05 | 79.09 | 79.20 | 13.01 | 13.03 | 3.69 | 3.58 |
| 1320 | 4-methylcyclohexyl-NH$_2$ | f | B | 203–211/0.05 | 79.09 | 79.23 | 13.01 | 13.05 | 3.69 | 3.57 |
| 1321 | 2-hydroxycyclohexyl-NH$_2$ | f | C | 200–206/0.04 | 75.53 | 75.62 | 12.41 | 12.59 | 3.67 | 3.45 |
| 1322 | 3-hydroxycyclohexyl-NH$_2$ | b | HD | 201–207/0.04 | 75.53 | 75.65 | 12.41 | 12.43 | 3.67 | 3.54 |
| 1323 | 4-hydroxycyclohexyl-NH$_2$ | c | B | 200–208/0.05 | 75.53 | 75.57 | 12.41 | 12.57 | 3.67 | 3.62 |
| 1324 | 2-methoxycyclohexyl-NH$_2$ | d | B | 201–210/0.04 | 75.89 | 75.94 | 12.48 | 12.57 | 3.54 | 3.53 |

-continued

| Ex. No. | Amine | Condensing agent | Solvent | b.p. °C./mmHg | C % Theoretical | C % Analytical | H % Theoretical | H % Analytical | N % Theoretical | N % Analytical |
|---|---|---|---|---|---|---|---|---|---|---|
| 1325 | 2-methoxycyclohexylamine | d | HA | 203–211/0.05 | 75.89 | 75.96 | 12.48 | 12.68 | 3.54 | 3.45 |
| 1326 | 4-methoxycyclohexylamine | f | I | 202–209/0.05 | 75.89 | 76.01 | 12.48 | 12.61 | 3.54 | 3.48 |
| 1327 | 4-ethoxycyclohexylamine | f | I | 200–214/0.08 | 76.22 | 76.24 | 12.55 | 12.64 | 3.42 | 3.34 |
| 1328 | 2-methylaniline | h | F | 204–211/0.06 | 80.37 | 80.52 | 11.60 | 11.68 | 3.75 | 3.62 |
| 1329 | 3-methylaniline | f | F | 202–210/0.05 | 80.37 | 80.63 | 11.60 | 11.79 | 3.75 | 3.63 |
| 1330 | 4-methylaniline | f | G | 202–211/0.05 | 80.37 | 80.33 | 11.60 | 11.75 | 3.75 | 3.25 |
| 1331 | 4-tert-butylaniline | f | C | 205–215/0.05 | 80.90 | 81.26 | 11.88 | 11.97 | 3.37 | 3.33 |
| 1332 | 2-hydroxyaniline | h | E | 210–216/0.06 | 80.15 | 80.39 | 11.49 | 11.62 | 3.90 | 3.81 |
| 1333 | 4-hydroxyaniline | f | D | 211–219/0.05 | 80.15 | 80.39 | 11.49 | 11.55 | 3.90 | 3.88 |
| 1334 | 2-chloroaniline | h | F | 203–214/0.07 | 73.18 | 73.44 | 10.16 | 10.29 | 3.55 | 3.40 |
| 1335 | 3-chloroaniline | e | F | 204–213/0.06 | 73.18 | 73.47 | 10.16 | 10.31 | 3.55 | 3.40 |
| 1336 | 4-chloroaniline | h | C | 202–213/0.06 | 73.18 | 73.31 | 10.16 | 10.64 | 3.55 | 3.38 |
| 1337 | 2-bromoaniline | e | C | 204–218/0.06 | 65.75 | 65.96 | 9.13 | 9.29 | 3.19 | 3.09 |
| 1338 | 4-fluoroaniline | h | C | 199–204/0.04 | 76.39 | 76.58 | 10.61 | 10.83 | 3.71 | 3.54 |
| 1339 | 2-chloro-3-methylaniline | e | C | 204–211/0.05 | 73.61 | 73.82 | 10.30 | 10.51 | 3.43 | 3.37 |
| 1340 | 4-trifluoromethylaniline | h | F | 202–215/0.04 | 70.25 | 70.65 | 9.36 | 9.62 | 3.27 | 3.07 |
| 1341 | 3-trifluoromethylaniline | e | C | 203–214/0.03 | 70.25 | 70.41 | 9.36 | 9.45 | 3.25 | 3.06 |

-continued
| Ex. No. | Amine | Condensing agent | Solvent | b.p. °C./mmHg | C % Theoretical | C % Analytical | H % Theoretical | H % Analytical | N % Theoretical | N % Analytical |
|---|---|---|---|---|---|---|---|---|---|---|
| 1342 | 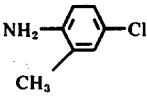 | e | F | 205,214/0.06 | 73.61 | 73.87 | 10.30 | 10.45 | 3.43 | 3.39 |
| 1343 |  | e | G | 200–223/0.05 | 79.09 | 79.34 | 13.01 | 13.09 | 3.69 | 3.46 |
| 1344 | 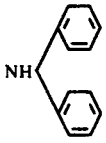 | e | B | 201–223/0.05 | 82.70 | 82.43 | 10.41 | 10.68 | 3.22 | 3.09 |
| 1345 | 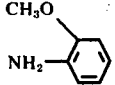 | a | A | 203–209/0.05 | 77.07 | 77.24 | 11.13 | 11.25 | 3.63 | 3.58 |
| 1346 | 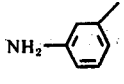 | b | H | 201–209/0.05 | 77.07 | 77.19 | 11.13 | 11.29 | 3.60 | 3.41 |
| 1347 | 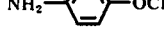 | a | HD | 200–210/0.05 | 77.07 | 77.33 | 11.13 | 11.25 | 3.60 | 3.40 |
| 1348 | 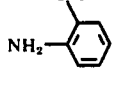 | a | HD | 201–214/0.04 | 77.36 | 77.51 | 11.24 | 11.63 | 3.47 | 3.36 |
| 1349 | 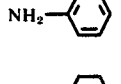 | a | HE | 200–220/0.08 | 77.36 | 77.49 | 11.24 | 11.35 | 3.47 | 3.18 |
| 1350 |  | c | B | 199–218/0.08 | 77.36 | 77.46 | 11.24 | 11.38 | 3.47 | 3.27 |
| 1351 |  | f | I | 200–208/0.04 | 78.27 | 78.53 | 12.84 | 12.99 | 4.15 | 3.95 |
| 1352 |  | d | B | 200–208/0.05 | 78.56 | 78.84 | 12.90 | 13.07 | 3.98 | 3.88 |
| 1353 | 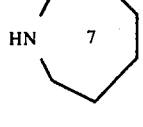 | f | C | 200–213/0.05 | 78.84 | 78.92 | 12.96 | 13.08 | 3.83 | 3.46 |
| 1354 |  | d | B | 200–214/0.06 | 74.73 | 74.92 | 12.26 | 12.54 | 3.96 | 3.65 |
| 1355 | 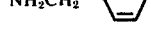 | f | C | 201–209/0.05 | 80.37 | 80.61 | 11.60 | 11.87 | 3.75 | 3.52 |
| 1356 | 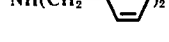 | a | HE | 218–223/0.06 | 82.88 | 82.90 | 10.65 | 10.94 | 3.02 | 3.00 |

-continued

| Ex. No. | Amine | Condensing agent | Solvent | b.p. °C./mmHg | C % Theoretical | C % Analytical | H % Theoretical | H % Analytical | N % Theoretical | N % Analytical |
|---|---|---|---|---|---|---|---|---|---|---|
| 1357 | NH$_2$CH(CH$_3$)–C$_6$H$_5$ | f | F | 201–212/0.05 | 80.56 | 80.76 | 11.70 | 11.92 | 3.61 | 3.38 |
| 1358 | NH$_2$CH(C$_2$H$_5$)–C$_6$H$_5$ | b | HD | 203–209/0.05 | 81.14 | 81.34 | 11.35 | 11.48 | 3.51 | 3.50 |
| 1359 | 2-OH–C$_6$H$_4$–CH$_2$NH$_2$ | f | G | 211–219/0.04 | 77.07 | 77.27 | 11.13 | 11.22 | 3.60 | 3.49 |
| 1360 | 4-OH–C$_6$H$_4$–CH$_2$NH$_2$ | d | B | 209–218/0.05 | 77.07 | 77.30 | 11.13 | 11.32 | 3.60 | 3.25 |
| 1361 | 2-OCH$_3$–C$_6$H$_4$–CH$_2$NH$_2$ | f | C | 205–218/0.05 | 77.36 | 77.49 | 11.24 | 11.46 | 3.47 | 3.33 |
| 1362 | 3-OCH$_3$–C$_6$H$_4$–CH$_2$NH$_2$ | f | I | 205–215/0.04 | 77.36 | 77.52 | 11.24 | 11.38 | 3.47 | 3.29 |
| 1363 | 4-OCH$_3$–C$_6$H$_4$–CH$_2$NH$_2$ | c | G | 203–218/0.05 | 77.36 | 77.54 | 11.24 | 11.49 | 3.47 | 3.41 |
| 1364 | 4-OC$_2$H$_5$–C$_6$H$_4$–CH$_2$NH$_2$ | a | HE | 206–219/0.05 | 77.64 | 77.66 | 11.34 | 11.38 | 3.35 | 3.29 |
| 1365 | 2-CH$_3$–C$_6$H$_4$–CH$_2$NH$_2$ | c | HE | 200–213/0.05 | 80.56 | 80.84 | 11.70 | 11.91 | 3.61 | 3.67 |
| 1366 | 3-CH$_3$–C$_6$H$_4$–CH$_2$NH$_2$ | e | B | 200–206/0.04 | 80.56 | 80.72 | 11.70 | 11.90 | 3.61 | 3.48 |
| 1367 | 4-CH$_3$–C$_6$H$_4$–CH$_2$NH$_2$ | a | H | 200–206/0.04 | 80.56 | 80.63 | 11.70 | 11.94 | 3.61 | 3.35 |
| 1368 | C$_6$H$_5$–CH(CH$_3$)–NH– | e | C | 200–214/0.05 | 80.37 | 80.49 | 11.60 | 11.83 | 3.75 | 3.67 |
| 1369 | 3-CH$_3$–C$_6$H$_4$–CH(C$_2$H$_5$)–NH– | f | C | 201–209/0.02 | 80.73 | 80.82 | 11.80 | 11.90 | 3.49 | 3.16 |
| 1370 | 2,4,6-(CH$_3$)$_3$–C$_6$H$_2$–NH$_2$ | f | F | 203–209/0.04 | 80.73 | 80.91 | 11.80 | 12.05 | 3.49 | 3.34 |
| 1371 | 2-Cl-4-CH$_3$–C$_6$H$_3$–NH$_2$ | f | G | 200–214/0.05 | 73.61 | 73.88 | 10.30 | 10.58 | 3.43 | 3.31 |
| 1372 | 2-CH$_3$-3-Cl–C$_6$H$_3$–NH$_2$ | b | HA | 200–217/0.05 | 73.61 | 73.79 | 10.30 | 10.49 | 3.43 | 3.30 |

-continued

| Ex. No. | Amine | Condensing agent | Solvent | b.p. °C./mmHg | C % Theoretical | C % Analytical | H % Theoretical | H % Analytical | N % Theoretical | N % Analytical |
|---|---|---|---|---|---|---|---|---|---|---|
| 1373 | NH₂—⟨⟩—F (meta) | f | C | 200–211/0.05 | 76.39 | 73.62 | 10.61 | 10.87 | 3.71 | 3.49 |
| 1374 | NH₂—⟨⟩—Br | f | C | 200–213/0.05 | 65.75 | 65.85 | 9.13 | 9.43 | 3.19 | 3.48 |
| 1375 | NH₂—⟨⟩(CH₅)—Cl | f | C | 200–215/0.05 | 73.61 | 73.76 | 10.30 | 10.66 | 3.43 | 3.19 |
| 1376 | NH₂—(bicyclic) | b | HA | 215–223/0.06 | 80.51 | 80.77 | 12.31 | 10.42 | 3.35 | 3.05 |

EXAMPLE 1377

A mixture of 10 g. of isostearic acid and 5 g. of cyclohexylamine was reacted with stirring at 150° C. for 39 hours removing water during the reaction. The reaction mixture was immediately distilled to obtain 11.5 g. of a desired product, b.p. 200°–206° C./0.08 mmHg. Elementary analysis:

|  | Theoretical | Analytical |
|---|---|---|
| C (%) | 78.84 | 79.06 |
| H (%) | 12.96 | 12.83 |
| N (%) | 3.83 | 3.78 |

Examples 1378–1428 are shown in the following table:

| Ex. No. | Amine | Reaction time (hr.) | Reaction temperature (°C.) | Autoclave | b.p. °C./mmHg | C % Theoretical | C % Analytical | H % Theoretical | H % Analytical | N % Theoretical | N % Analytical |
|---|---|---|---|---|---|---|---|---|---|---|---|
| 1378 | NH₂CH(CH₃)₂ | 20 | 180 | Used | 187–201/0.05 | 77.48 | 77.68 | 13.32 | 13.09 | 4.30 | 4.18 |
| 1379 | NH(CH₃)₂ | 50 | 200 | Used | 190–200/0.06 | 77.10 | 77.41 | 13.27 | 13.07 | 4.50 | 4.22 |
| 1380 | NH₂CH₂CH=CH₂ | 20 | 180 | Used | 193–204/0.06 | 77.95 | 78.26 | 12.77 | 12.51 | 4.33 | 4.10 |
| 1381 | NH(CH₂CH=CH₂)₂ | 50 | 200 | Used | 198–208/0.05 | 79.27 | 79.41 | 12.47 | 12.22 | 3.85 | 3.58 |
| 1382 | NH₂—⟨cyclobutyl⟩ | 28 | 185 | Used | 200–207/0.05 | 78.56 | 78.78 | 12.90 | 12.77 | 3.98 | 3.64 |
| 1383 | NH₂—⟨cycloheptyl⟩ | 38 | 150 | None | 200–212/0.06 | 79.09 | 79.15 | 13.01 | 12.89 | 3.69 | 3.43 |
| 1384 | NH₂—⟨⟩(CH₃) (2-Me-cyclohexyl) | 27 | 160 | — | 205–212/0.07 | 77.09 | 79.23 | 13.01 | 12.86 | 3.69 | 3.45 |
| 1385 | NH₂—⟨⟩(CH₃) (3-Me-cyclohexyl) | 25 | 160 | — | 202–209/0.07 | 79.09 | 79.22 | 13.01 | 12.91 | 3.69 | 3.42 |
| 1386 | NH₂—⟨⟩—CH₃ (4-Me-cyclohexyl) | 25 | 160 | — | 200–210/0.05 | 79.09 | 79.31 | 13.01 | 12.37 | 3.69 | 3.53 |

-continued

| Ex. No. | Amine | Reaction time (hr.) | Reaction temperature (°C.) | Autoclave | b.p. °C./mmHg | C % Theoretical | C % Analytical | H % Theoretical | H % Analytical | N % Theoretical | N % Analytical |
|---|---|---|---|---|---|---|---|---|---|---|---|
| 1387 | OCH₃-cyclohexyl-NH₂ (1,2) | 28 | 185 | — | 205–213/0.06 | 75.89 | 76.02 | 12.48 | 12.40 | 3.54 | 3.28 |
| 1388 | OCH₃-cyclohexyl-NH₂ (1,3) | 30 | 185 | — | 203–214/0.05 | 75.89 | 76.04 | 12.48 | 12.28 | 3.54 | 3.37 |
| 1389 | NH₂-cyclohexyl-CH₃ | 29 | 185 | — | 200–218/0.05 | 75.89 | 76.00 | 12.48 | 12.19 | 3.54 | 3.31 |
| 1390 | NH₂-cyclohexyl-OC₂H₅ | 29 | 185 | — | 203–209/0.04 | 76.22 | 76.40 | 12.55 | 12.28 | 3.42 | 3.10 |
| 1391 | HO-cyclohexyl-NH₂ | 29 | 185 | — | 200–211/0.05 | 75.53 | 75.75 | 12.41 | 12.06 | 3.67 | 3.37 |
| 1392 | NH₂-cyclohexyl-OH | 29 | 185 | — | 200–209/0.05 | 75.53 | 75.80 | 12.41 | 12.38 | 3.67 | 3.43 |
| 1393 | CH₃-phenyl-NH₂ (o) | 32 | 180 | — | 199–208/0.06 | 80.37 | 80.46 | 11.60 | 11.41 | 3.75 | 3.52 |
| 1394 | CH₃-phenyl-NH₂ (m) | 32 | 180 | — | 200–211/0.06 | 80.37 | 80.54 | 11.60 | 11.43 | 3.75 | 3.56 |
| 1395 | NH₂-phenyl-CH₃ (p) | 32 | 180 | — | 200–213/0.06 | 80.37 | 80.63 | 11.60 | 11.34 | 3.75 | 3.79 |
| 1396 | OH-phenyl-NH₂ | 30 | 185 | — | 210–231/0.04 | 80.15 | 80.43 | 11.49 | 11.29 | 3.90 | 3.47 |
| 1397 | NH₂-phenyl-OH | 30 | 185 | — | 208–222/0.04 | 80.15 | 80.33 | 11.49 | 11.31 | 3.90 | 3.90 |
| 1398 | CH₃O-phenyl-NH₂ | 30 | 185 | — | 200–208/0.05 | 77.07 | 77.39 | 11.13 | 11.50 | 3.60 | 3.62 |
| 1399 | NH₂-phenyl-OCH₃ | | 185 | — | 201–209/0.06 | 77.07 | 77.25 | 11.13 | 11.00 | 3.60 | 3.43 |
| 1400 | NH₂-phenyl-OCH₃ | 33 | 185 | — | 202–211/0.06 | 77.07 | 77.28 | 11.13 | 10.87 | 3.60 | 3.59 |
| 1401 | OC₂H₅-phenyl-NH₂ | 33 | 185 | — | 201–209/0.05 | 77.36 | 77.60 | 11.24 | 10.94 | 3.47 | 3.04 |
| 1402 | OC₂H₅-phenyl-NH₂ | 30 | 185 | — | 201–213/0.06 | 77.36 | 77.54 | 11.24 | 10.02 | 3.47 | 3.30 |
| 1403 | NH₂-phenyl-OC₂H₅ | 42 | 185 | — | 203–214/0.07 | 77.36 | 77.55 | 11.24 | 10.02 | 3.47 | 3.29 |

-continued

| Ex. No. | Amine | Reaction time (hr.) | Reaction temperature (°C.) | Autoclave | b.p. °C./mmHg | C % Theoretical | C % Analytical | H % Theoretical | H % Analytical | N % Theoretical | N % Analytical |
|---|---|---|---|---|---|---|---|---|---|---|---|
| 1404 | $NH_2$—⟨⟩—F | 32 | 185 | — | 199–210/0.05 | 76.39 | 76.61 | 10.61 | 10.41 | 3.71 | 3.56 |
| 1405 | $NH_2$—⟨⟩—Cl | 31 | 185 | — | 195–208/0.05 | 73.18 | 73.30 | 10.16 | 10.04 | 3.55 | 3.30 |
| 1406 | $NH_2$—⟨⟩—$CF_3$ | 30 | 185 | — | 198–207/0.05 | 70.25 | 70.52 | 9.36 | 8.98 | 3.27 | 3.04 |
| 1407 | $NH_2$—⟨⟩ ($CF_3$ meta) | 30 | 185 | — | 201–211/0.07 | 70.25 | 70.54 | 9.36 | 9.12 | 3.27 | 3.03 |
| 1408 | $CH_3$, $NH_2$, Cl (substituted phenyl) | 42 | 185 | — | 207–211/0.05 | 73.61 | 73.89 | 10.30 | 10.08 | 3.43 | 3.15 |
| 1409 | $NH_2$—⟨⟩—Cl, $CH_3$ | 38 | 185 | — | 200–214/0.04 | 73.61 | 73.80 | 10.30 | 10.17 | 3.43 | 3.11 |
| 1410 | $NH_2$—⟨⟩—C($CH_3$)$_3$ | 40 | 180 | — | 203–213/0.04 | 80.90 | 81.15 | 11.88 | 11.59 | 3.37 | 3.16 |
| 1411 | $NH_2$—⟨⟩—OH | 39 | 185 | — | 210–223/0.03 | 80.15 | 80.46 | 11.49 | 11.10 | 3.90 | 3.65 |
| 1412 | HO, $NH_2$ (substituted phenyl) | 40 | 185 | — | 207–217/0.06 | 80.15 | 80.35 | 11.49 | 11.31 | 3.90 | 3.74 |
| 1413 | HN⟨⟩ (5-ring) | 60 | 185 | — | 200–210/0.05 | 78.27 | 78.44 | 12.84 | 12.63 | 4.15 | 4.07 |
| 1414 | HN⟨⟩ (6-ring) | 60 | 200 | — | 200–213/0.05 | 78.56 | 78.72 | 12.90 | 12.74 | 3.98 | 3.82 |
| 1415 | HN⟨7⟩ | 60 | 200 | — | 199–209/0.05 | 78.84 | 79.05 | 12.96 | 12.81 | 3.83 | 3.71 |
| 1416 | HN⟨⟩O (morpholine) | 60 | 200 | — | 203–215/0.05 | 74.73 | 74.93 | 12.26 | 12.05 | 3.96 | 3.85 |
| 1417 | $NH_2CH_2$—⟨⟩ | 30 | 185 | — | 200–214/0.05 | 80.37 | 80.67 | 11.60 | 11.40 | 3.75 | 3.63 |
| 1418 | $NH_2CH$(—⟨⟩)$C_3$ | 32 | 185 | — | 201–207/0.04 | 80.56 | 80.74 | 11.70 | 11.57 | 3.61 | 3.61 |
| 1419 | $NH_2CH$(—⟨⟩)$C_2H_5$ | 33 | 200 | — | 203–211/0.05 | 81.14 | 81.48 | 11.35 | 11.25 | 3.51 | 3.58 |

| Ex. No. | Amine | Reaction time (hr.) | Reaction temperature (°C.) | Auto-clave | b.p. °C./mmHg | C % Theoretical | C % Analytical | H % Theoretical | H % Analytical | N % Theoretical | N % Analytical |
|---|---|---|---|---|---|---|---|---|---|---|---|
| 1420 | NH₂CH₂–C₆H₄–CH₃ | 30 | 185 | — | 200–215/0.08 | 80.56 | 80.99 | 11.70 | 11.53 | 3.61 | 3.49 |
| 1421 | NH₂CH₂–C₆H₄–CH₃ | 25 | 200 | — | 207–223/0.1 | 80.56 | 80.81 | 11.70 | 11.46 | 3.61 | 3.44 |
| 1422 | NH₂CH₂–C₆H₄–OH | 25 | 185 | — | 205–213/0.08 | 77.07 | 77.24 | 11.13 | 11.02 | 3.60 | 3.43 |
| 1423 | NH₂CH₂–C₆H₄(HO) | 25 | 185 | — | 206–223/0.07 | 77.07 | 77.27 | 11.13 | 10.96 | 3.60 | 3.25 |
| 1424 | NH₂CH₂–C₆H₄–CH₃O | 28 | 190 | — | 203–222/0.05 | 77.36 | 77.52 | 11.24 | 11.01 | 3.47 | 3.39 |
| 1425 | NH₂CH₂–C₆H₄–OCH₃ | 28 | 190 | — | 207–219/0.07 | 77.36 | 77.68 | 11.24 | 11.04 | 3.47 | 3.28 |
| 1426 | NH₂C₁₂H₂₅ | 33 | 190 | — | | 80.11 | 80.41 | 13.22 | 13.10 | 3.11 | 3.06 |
| 1427 | (bicyclic)NH₂ | 30 | 185 | — | 218–228/0.06 | 80.51 | 80.78 | 12.31 | 12.00 | 3.35 | 3.17 |
| 1428 | dicyclohexyl-NH | 60 | 200 | — | 210–221/0.04 | 80.47 | 80.63 | 12.83 | 13.18 | 3.13 | 3.02 |

EXAMPLE 1429

A mixture of 10 g. of methyl isostearate and 5 g. of cyclohexylamine was stirred at 140° C for 30 hours removing methanol out of the reaction system. The reaction mixture was distilled to obtain 12.1 g. of a desired product, b.p. 200°–205° C./mmHg. Elementary analysis:

|  | Theoretical | Analytical |
|---|---|---|
| C (%) | 78.84 | 79.12 |
| H (%) | 12.96 | 12.61 |
| N (%) | 3.83 | 3.70 |

EXAMPLE 1430

To a mixture of 10 g. of methyl isostearate and 2 g. of isopropylamine was added a solution of 0.5 g. of sodium in 5 ml. of anhydrous methanol, and the mixture was reacted in an autoclave at 140° C. for 2 hours. The reaction mixture was charged with 100 ml. of ether and washed with water, 5% hydrochloric acid water and water, and was then dried, concentrated and distilled to obtain 9.9 g. of a desired product, b.p. 185°–199° C./0.02 mmHg. Elementary analysis:

|  | Theoretical | Analytical |
|---|---|---|
| C (%) | 77.48 | 77.64 |
| H (%) | 13.32 | 13.10 |
| N (%) | 4.30 | 4.19 |

EXAMPLE 1431

A mixture of 10 g. of methyl isostearate, 2 g of allylamine and 0.5 g. of powdery sodium methylate was stirred in an autoclave at 150° C. for 3 hours. The mixture was treated in the same manner as in Example 1430 to obtain 9.3 g. of a desired product, b.p. 191°–197° C./0.05 mmHg. Elementary analysis:

|  | Theoretical | Analytical |
|---|---|---|
| C (%) | 77.95 | 77.69 |
| H (%) | 12.77 | 12.49 |
| N (%) | 4.33 | 4.41 |

EXAMPLE 1432

A mixture of 10 g. of ethyl isostearate, 6 g. of α-methylbenzylamine and 1 g. of potassium t-butyrate was heated with stirring at 180° C. for 5 hours. Immediately after the heating, the mixture was distilled to obtain 11.8 g. of a desired product, b.p. 205°–208° C./0.1 mmHg. Elementary analysis:

|       | Theoretical | Analytical |
|-------|-------------|------------|
| C (%) | 80.56       | 80.81      |
| H (%) | 11.70       | 11.38      |
| N (%) | 3.61        | 3.31       |

EXAMPLE 1433

A mixture of 10 g. of methyl isostearate and 5 g. of p-methoxy-cyclohexylamine was heated with stirring in an autoclave at 220° C. for 8 hours to obtain 10.4 g. of a desired product, b.p. 204°–211° C./0.05 mmHg. Elementary analysis:

|       | Theoretical | Analytical |
|-------|-------------|------------|
| C (%) | 75.89       | 76.10      |
| H (%) | 12.48       | 12.27      |
| N (%) | 3.54        | 3.29       |

EXAMPLE 1434

A mixture of 10 g. of methyl isostearate, 6 g. of cycloheptylamine and 0.5 g. of sodium methylate, and the mixture was heated with stirring at 150° C. for 48 hours removing methanol. Subsequently, the same treatments as in Example 1430 were effected to obtain a desired product, b.p. 206°–210° C.0.09 mmHg. Elementary analysis:

|       | Theoretical | Analytical |
|-------|-------------|------------|
| C (%) | 79.09       | 79.33      |
| H (%) | 13.01       | 12.84      |
| N (%) | 3.69        | 3.35       |

EXAMPLE 1435

To a mixture of 10 g. of methyl isostearate and 5 g. of o-toluidine was added a solution of 1 g. of sodium in 10 ml. of anhydrous methanol, and the mixture was stirred at 150° C. for 6 hours, removing methanol. The same treatments as in Example 1430 were effected to obtain a desired product, b.p. 204°–212° C./0.07 mmHg. Elementary analysis:

|       | Theoretical | Analytical |
|-------|-------------|------------|
| C (%) | 80.37       | 80.57      |
| H (%) | 11.60       | 11.29      |
| N (%) | 3.75        | 3.50       |

EXAMPLE 1436

To a mixture of 10 g. of methyl isostearate and 5 g. of 2-chloro-6-methylaniline was added a suspension of 1 g. of sodium methylate in 5 ml. of benzene, and the mixture was stirred at 85° C. for 10 hours. The same treatments as in Example 1430 were effected to obtain 12.1 g. of a desired product, b.p. 209°–215° C./0.06 mmHg. Elementary analysis:

|       | Theoretical | Analytical |
|-------|-------------|------------|
| C (%) | 73.61       | 73.88      |
| H (%) | 10.30       | 10.14      |
| N (%) | 3.43        | 3.16       |

EXAMPLE 1437

A mixture of 10 g. of methyl isostearate and 10 g. of dodecylamine, was stirred at 180° C. for 26 hours. The reaction product was treated in the same manner as in Example 1430 to obtain a desired product. Elementary analysis:

|       | Theoretical | Analytical |
|-------|-------------|------------|
| C (%) | 80.11       | 80.41      |
| H (%) | 13.22       | 12.89      |
| N (%) | 3.11        | 3.01       |

Examples 1438–1476 are shown in the following table:

| Example No. | Amine | Reference example | Condensing agent | Reaction temperature ° C. | Reaction time hr. | Solvent | Autoclave | b.p. ° C./mmHg |
|---|---|---|---|---|---|---|---|---|
| 1438 | NH(CH₃)₂ (see structure) | 1433 | — | 200 | 18 | — | Used | 189–194/0.04 |
| 1439 | NH(CH₂CH=CH₂)₂ | 1433 | — | 200 | 18 | — | Used | 195–201/0.06 |
| 1440 | NH₂-cyclobutyl | 1433 | — | 200 | 10 | — | Used | 200–204/0.07 |
| 1441 | CH₃-cyclohexyl-NH₂ | 1434 | NaOCH₃ | 150 | 6 | — | — | 202–208/0.05 |

-continued

| # | Structure | Ref | Base | Temp | Time | Solv | Cat | bp/mmHg |
|---|---|---|---|---|---|---|---|---|
| 1442 | NH₂—⟨cyclohexyl⟩—OCH₃ | 1434 | NaOCH₃ | 150 | 6 | — | — | 200–211/0.05 |
| 1443 | NH₂—⟨cyclohexyl⟩—OC₂H₅ | 1434 | NaOCH₃ | 150 | 6 | — | — | 203–213/0.05 |
| 1444 | NH₂—⟨phenyl⟩—C(CH₃)₃ | 1433 | — | 200 | 10 | — | Used | 205–215/0.05 |
| 1445 | NH₂—⟨phenyl⟩—OH | 1429 | — | 160 | 30 | — | — | 209–214/0.04 |
| 1446 | 2-CH₃, 6-Cl aniline | 1429 | — | 160 | 35 | — | — | 208–214/0.04 |
| 1447 | NH₂—⟨phenyl⟩—F | 1429 | — | 140 | 60 | — | — | 198–206/0.04 |
| 1448 | NH₂—⟨phenyl⟩—CF₃ | 1429 | — | 140 | 58 | — | — | 202–216/0.04 |
| 1449 | 2-OCH₃ aniline | 1434 | NaOMe | 150 | 8 | — | — | 208–214/0.04 |
| 1450 | NH₂—⟨phenyl⟩—OCH₃ | 1434 | NaOMe | 150 | 8 | — | — | 200–206/0.04 |
| 1451 | 3-OC₂H₅ aniline | 1432 | KOtBu | 150 | 8 | — | — | 200–209/0.04 |
| 1452 | 2-OC₂H₅ aniline | 1431 | NaOMe | 200 | 10 | — | Used | 204–209/0.04 |
| 1453 | HN⟨pyrrolidine⟩ | 1431 | NaOEt | 200 | 10 | — | Used | 200–207/0.06 |
| 1454 | HN⟨piperidine⟩ | 1431 | NaOEt | 200 | 10 | — | Used | 200–206/0.06 |
| 1455 | HN⟨morpholine⟩O | 1431 | KOtBu | 200 | 10 | — | Used | 209–213/0.05 |
| 1456 | HN⟨7-membered ring⟩ | 1431 | KOtBu | 200 | 10 | — | Used | 206–211/0.07 |
| 1457 | NH₂CH₂—⟨phenyl⟩ | 1435 | NaOEt | 180 | 8 | MeOH | — | 201–209/0.05 |
| 1458 | NH₂—CH(CH₃)—⟨phenyl⟩ | 1429 | — | 180 | 32 | — | — | 201–205/0.04 |
| 1459 | NH₂—CH(C₂H₅)—⟨phenyl⟩ | 1432 | KOtBu | 180 | 5 | — | — | 203–206/0.05 |
| 1460 | NH₂CH₂—⟨phenyl⟩—OH | 1429 | — | 180 | 20 | — | — | 211–218/0.04 |

-continued

| | | | | | | | |
|---|---|---|---|---|---|---|---|
| 1461 | 2-(HO)C6H4-CH2NH2 | 1429 | — | 180 | 20 | — | — | 209-217/0.04 |
| 1462 | 2-(OCH3)C6H4-CH2NH2 | 1429 | — | 180 | 22 | — | — | 208-215/0.05 |
| 1463 | 4-(OCH3)C6H4-CH2NH2 | 1429 | — | 180 | 20 | — | — | 205-213/0.04 |
| 1464 | 2-(OCH3)C6H4-CH2NH2 | 1433 | — | 200 | 20 | — | Used | 204-209/0.04 |
| 1465 | 2-(CH3)C6H4-CH2NH2 | 1434 | NaOEt | 180 | 5 | — | — | 200-211/0.07 |
| 1466 | 3-(CH3)C6H4-CH2NH2 | 1434 | NaOMe | 180 | 5 | — | — | 203-217/0.1 |
| 1467 | 4-(CH3)C6H4-CH2NH2 | 1434 | NaOMEe | 180 | 5 | — | — | 205-212/0.05 |
| 1468 | 2-(OCH3)cyclohexyl-NH2 | 1431 | NaOMe | 200 | 5 | — | Used | 201-206/0.06 |
| 1469 | 3-(CF3)C6H4-NH2 | 1429 | — | 180 | 25 | — | — | 207-220/0.07 |
| 1470 | 4-Cl-C6H4-NH2 | 1429 | — | 180 | 35 | — | — | 201-207/0.06 |
| 1471 | 4-Cl-2-CH3-C6H3-NH2 | 1429 | — | 180 | 35 | — | — | 200-209/0.06 |
| 1472 | 2-(HO)C6H4-CH2NH2 | 1433 | — | 200 | 27 | — | Used | 209-215/0.06 |
| 1473 | 4-(HO)C6H4-CH2NH2 | 1433 | — | 200 | 30 | — | Used | 205-210/0.07 |
| 1474 | 4-(HO)cyclohexyl-NH2 | 1429 | — | 180 | 32 | — | — | 202-208/0.06 |
| 1475 | 1-adamantyl-NH2 | 1429 | — | 200 | 40 | — | — | 218-225/0.07 |
| 1476 | dicyclohexyl-NH | 1431 | KOtBu | 220 | 10 | — | Used | 210-221/0.05 |

| Example No. | Amine | C % Theoretical | C % Analytical | H % Theoretical | H % Analytical | N % Theoretical | N % Analytical |
|---|---|---|---|---|---|---|---|
| 1438 | 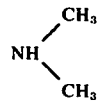 NH(CH₃)₂ | 77.10 | 77.41 | 13.27 | 13.00 | 4.50 | 4.31 |
| 1439 | NH(CH₂CH=CH₂)₂ | 79.27 | 79.59 | 12.47 | 12.09 | 3.85 | 3.55 |
| 1440 | 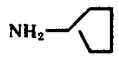 | 78.56 | 78.78 | 12.90 | 12.62 | 3.98 | 3.78 |
| 1441 | 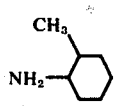 | 79.09 | 79.38 | 13.01 | 12.87 | 3.69 | 3.48 |
| 1442 | 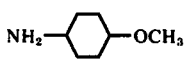 | 75.89 | 75.99 | 12.48 | 12.29 | 3.54 | 3.23 |
| 1443 | 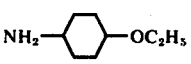 | 76.22 | 76.56 | 12.55 | 12.31 | 3.42 | 3.19 |
| 1444 | 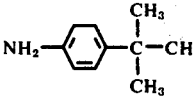 | 80.90 | 81.20 | 11.88 | 11.65 | 3.37 | 3.17 |
| 1445 | 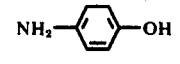 | 80.15 | 80.42 | 11.49 | 11.19 | 3.90 | 3.65 |
| 1446 | 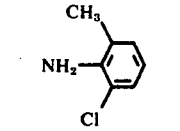 | 73.61 | 73.90 | 10.30 | 10.05 | 3.43 | 3.33 |
| 1447 | 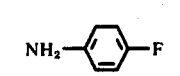 | 76.39 | 76.66 | 10.61 | 10.45 | 3.71 | 3.70 |
| 1448 | 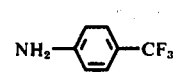 | 70.25 | 70.50 | 9.36 | 9.18 | 3.27 | 3.29 |
| 1449 | 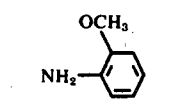 | 77.07 | 77.19 | 11.13 | 11.05 | 3.63 | 3.85 |
| 1450 | 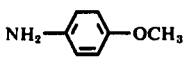 | 77.07 | 77.23 | 11.13 | 11.54 | 3.60 | 3.32 |
| 1451 | 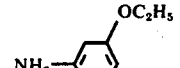 | 77.36 | 77.59 | 11.24 | 11.04 | 3.47 | 3.34 |
| 1452 | 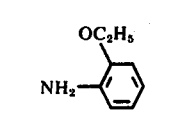 | 77.36 | 77.58 | 11.24 | 11.60 | 3.47 | 3.21 |
| 1453 | 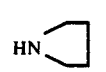 | 78.27 | 78.59 | 12.84 | 12.53 | 4.15 | 4.00 |
| 1454 | 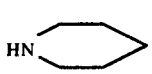 | 78.56 | 78.39 | 12.90 | 13.06 | 3.98 | 4.05 |
| 1455 | 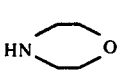 | 74.73 | 74.99 | 12.26 | 12.01 | 3.96 | 3.80 |

-continued
| | | | | | | | |
|---|---|---|---|---|---|---|---|
| 1456 |  | 78.84 | 79.08 | 12.96 | 12.70 | 3.83 | 3.62 |
| 1457 | 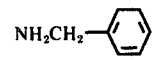 | 80.37 | 80.66 | 11.60 | 11.27 | 3.75 | 3.65 |
| 1458 | 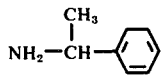 | 80.56 | 80.98 | 11.70 | 11.53 | 3.61 | 3.47 |
| 1459 | 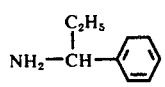 | 81.14 | 81.51 | 11.35 | 10.99 | 3.51 | 3.31 |
| 1460 | 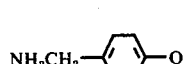 | 77.07 | 77.16 | 11.13 | 11.02 | 3.60 | 3.48 |
| 1461 |  | 77.07 | 77.26 | 11.13 | 11.02 | 3.60 | 3.50 |
| 1462 | 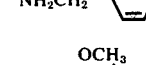 | 77.36 | 77.67 | 11.24 | 11.09 | 3.47 | 3.13 |
| 1463 | 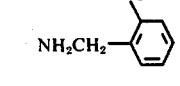 | 77.36 | 77.74 | 11.24 | 11.08 | 3.47 | 3.21 |
| 1464 | 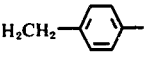 | 77.36 | 77.62 | 11.24 | 11.12 | 3.47 | 3.19 |
| 1465 | 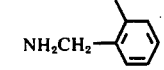 | 80.56 | 80.78 | 11.70 | 11.54 | 3.61 | 3.58 |
| 1466 | 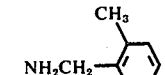 | 80.56 | 80.81 | 11.70 | 11.37 | 3.61 | 3.51 |
| 1467 |  | 80.56 | 80.80 | 11.70 | 11.61 | 3.61 | 3.60 |
| 1468 | 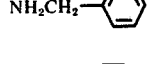 | 75.89 | 76.06 | 12.48 | 12.09 | 3.54 | 3.41 |
| 1469 | 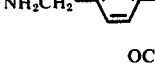 | 70.25 | 70.82 | 9.36 | 9.04 | 3.27 | 3.00 |
| 1470 | 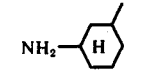 | 73.18 | 73.89 | 10.16 | 9.85 | 3.55 | 3.19 |
| 1471 | 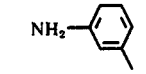 | 73.61 | 73.91 | 10.30 | 9.94 | 3.43 | 3.18 |
| 1472 | 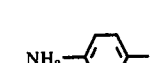 | 77.07 | 77.21 | 11.13 | 10.97 | 3.60 | 3.30 |
| 1473 | 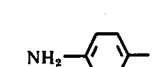 | 77.07 | 77.25 | 11.13 | 10.89 | 3.60 | 3.41 |

-continued

| 1474 | NH₂—⬡—OH | 75.53 | 75.69 | 12.41 | 12.19 | 3.67 | 3.33 |
| --- | --- | --- | --- | --- | --- | --- | --- |
| 1475 | NH₂-adamantyl | 80.51 | 80.88 | 12.31 | 12.06 | 3.35 | 3.16 |
| 1476 | dicyclohexyl-NH | 80.47 | 80.61 | 12.83 | 12.66 | 3.13 | 3.04 |

EXAMPLE 1477

Linoleic acid (16 g.), 16 g. of dicyclohexyl carbodiimide and 9.5 g. of dicyclohexylamine were individually dissolved in 20 ml. of benzene. The thus prepared three solutions were mixed together at one portion, and the mixed solution was stirred for about 3 minutes. The mixed solution was allowed to stand at room temperature for about 18 hours, and 3 ml. of acetic acid was added to the solution, and then the mixture was allowed to stand at room temperature for additional 2 hours. Thereafter, precipitated dicyclohexylurea was separated by filtration, and the filtrate was washed with 5% HCl water, 5% NaOH water and water, and was then dried, concentrated and distilled to obtain 19.2 g. of a desired product, b.p. 200°–209° C./0.05 mmHg, $n_D^{26}$ 1.4880. Elementary analysis:

|  | Theoretical | Analytical |
| --- | --- | --- |
| C (%) | 81.20 | 79.94 |
| H (%) | 12.04 | 12.00 |
| N (%) | 3.16 | 3.24 |

Examples 1478–1504 are shown in the following table:

| Example No. | Acid | Condensing agent | Solvent | b.p. °C/mmHg | C (%) Theoretical | C (%) Analytical | H (%) Theoretical | H (%) Analytical | N (%) Theoretical | N (%) Analytical |
| --- | --- | --- | --- | --- | --- | --- | --- | --- | --- | --- |
| 1478 | Linoleic acid | cyclohexyl | Dioxane | 203–210/0.07 | 81.20 | 81.09 | 12.04 | 11.99 | 3.16 | 3.21 |
| 1479 | " | cyclohexyl | Pyridine | 200–208/0.06 | 81.20 | 81.11 | 12.04 | 11.98 | 3.16 | 3.19 |
| 1480 | " | cyclohexyl | Chloroform | 202–209/0.06 | 81.20 | 81.07 | 12.04 | 12.01 | 3.16 | 3.14 |
| 1481 | " | phenyl | Chloroform | 203–209/0.06 | 81.20 | 81.05 | 12.04 | 12.31 | 3.16 | 3.20 |
| 1482 | " | phenyl | Toluene | 201–209/0.06 | 81.20 | 81.00 | 12.04 | 11.89 | 3.16 | 3.23 |
| 1483 | " | -i-Pro | Dioxane | 201–209/0.05 | 81.20 | 81.14 | 12.04 | 11.95 | 3.16 | 3.18 |
| 1484 | " | -i-Pro | Ether | 201–208/0.07 | 81.20 | 81.30 | 12.04 | 12.00 | 3.16 | 3.21 |
| 1485 | " | -i-Pro | Benzene | 204–211/0.08 | 81.20 | 80.99 | 12.04 | 12.03 | 3.16 | 3.19 |
| 1486 | Linolenic acid | cyclohexyl | Dioxane | 204–208/0.06 | 81.57 | 81.33 | 11.64 | 11.88 | 3.17 | 3.09 |
| 1487 | " | cyclohexyl | Tetrahydrofuran | 200–212/0.07 | 81.57 | 81.41 | 11.64 | 11.53 | 3.17 | 3.06 |
| 1488 | " | -i-Pro | Pyridine | 209–215/0.1 | 81.57 | 81.45 | 11.64 | 11.51 | 3.17 | 3.14 |
| 1489 | Oleic acid | cyclohexyl | Benzene | 195–208/0.05 | 80.83 | 80.81 | 12.44 | 12.29 | 3.14 | 3.05 |
| 1490 | Safflower oil | cyclohexyl | Benzene | 195–213/0.07 | — | — | — | — | — | — |
| 1491 | Cottonseed oil fatty acid | cyclohexyl | Toluene | 200–214/0.05 | — | — | — | — | — | — |
| 1492 | Cuttlefish oil | " | Ether | 200–215/0.05 | — | — | — | — | — | — |
| 1493 | Mackeral oil fatty acid | " | Tetrahydrofuran | 201–217/0.06 | — | — | — | — | — | — |
| 1494 | Flatfish oil fatty acid | " | Ether | 200–209/0.05 | — | — | — | — | — | — |
| 1495 | Saury pike oil fatty acid | " | Ether | 192–210/0.06 | — | — | — | — | — | — |
| 1496 | Herring oil fatty acid | " | Tetrahydrofuran | 199–213/0.06 | — | — | — | — | — | — |
| 1497 | Cod oil fatty acid | " | Toluene | 187–208/0.04 | — | — | — | — | — | — |
| 1498 | Sardine oil fatty acid | " | Dioxane | 187–209/0.05 | — | — | — | — | — | — |
| 1499 | Shark oil fatty acid | " | Ether | 187–211/0.07 | — | — | — | — | — | — |
| 1500 | Liver oil fatty acid | " | Dioxane | 200–214/0.06 | — | — | — | — | — | — |

-continued

| Example No. | Acid | Condensing agent | Solvent | b.p. °C/mmHg | C (%) Theoretical | C (%) Analytical | H (%) Theoretical | H (%) Analytical | N (%) Theoretical | N (%) Analytical |
|---|---|---|---|---|---|---|---|---|---|---|
| 1501 | Residual oil | " | Toluene | 205–216/0.08 | — | — | — | — | — | — |
| 1502 | Whale oil fatty acid | " | Ether | 200–209/0.07 | — | — | — | — | — | — |
| 1503 | Saurel oil fatty acid | " | Chloroform | 185–211/0.06 | — | — | — | — | — | — |
| 1504 | Menuke oil fatty acid | " | Ether | 195–209/0.07 | — | — | — | — | — | — |

EXAMPLE 1505 e. Xylene
f. Tetrachlorocarbon

| Example No. | Acid | Catalyst | Solvent | Reaction time hr | b.p. °C./mmHg | C (%) Theoretical | C (%) Analytical | H (%) Theoretical | H (%) Analytical | N (%) Theoretical | N (%) Analytical |
|---|---|---|---|---|---|---|---|---|---|---|---|
| 1506 | Oleic acid | A | a | 8 | 204–210/0.06 | 80.83 | 80.77 | 12.44 | 12.39 | 3.14 | 3.09 |
| 1507 | Oleic acid | A | c | 8 | 206–210/0.06 | 80.83 | 80.69 | 12.44 | 13.33 | 3.14 | 3.08 |
| 1508 | Oleic acid | C | a | 8 | 200–209/0.06 | 80.83 | 80.45 | 12.44 | 12.31 | 3.14 | 3.15 |
| 1509 | Linoleic acid | A | a | 8 | 203–207/0.05 | 81.20 | 81.56 | 12.04 | 12.01 | 3.16 | 3.33 |
| 1510 | Linoleic acid | B | b | 20 | 202–207/0.05 | 81.20 | 81.45 | 12.04 | 11.87 | 3.16 | 3.45 |
| 1511 | Linoleic acid | C | a | 8 | 203–207/0.06 | 81.20 | 81.09 | 12.04 | 11.95 | 3.16 | 3.09 |
| 1512 | Linoleic acid | D | a | 10 | 204–209/0.06 | 81.20 | 81.04 | 12.04 | 11.98 | 3.16 | 3.08 |
| 1513 | Linoleic acid | A | a | 8 | 204–209/0.06 | 81.20 | 81.29 | 12.04 | 11.88 | 3.16 | 3.43 |
| 1514 | Linoleic acid | A | d | 10 | 200–210/0.06 | 81.20 | 81.09 | 12.04 | 11.69 | 3.16 | 3.19 |
| 1515 | Linolenic acid | A | c | 8 | 206–209/0.06 | 81.57 | 81.69 | 11.64 | 11.45 | 3.17 | 3.09 |
| 1516 | Linolenic acid | A | c | 8 | 204–210/0.07 | 81.57 | 81.50 | 11.64 | 11.39 | 3.17 | 3.00 |
| 1517 | Linolenic acid | B | b | 20 | 203–207/0.06 | 81.57 | 81.47 | 11.64 | 11.58 | 3.17 | 3.15 |
| 1518 | Safflower oil acid | A | d | 10 | 195–207/0.06 | — | — | — | — | — | — |
| 1519 | Cottonseed oil acid | D | f | 10 | 198–210/0.06 | — | — | — | — | — | — |
| 1520 | Sesame oil acid | A | b | 15 | 196–209/0.06 | — | — | — | — | — | — |
| 1521 | Castor oil acid | B | c | 8 | 191–211/0.05 | — | — | — | — | — | — |
| 1522 | Cuttlefish oil acid | C | a | 12 | 195–214/0.06 | — | — | — | — | — | — |
| 1523 | Mackerel oil acid | C | e | 12 | 192–213/0.05 | — | — | — | — | — | — |
| 1524 | Flatfish oil acid | E | e | 10 | 195–209/0.06 | — | — | — | — | — | — |
| 1525 | Saury pike oil acid | A | a | 8 | 190–214/0.06 | — | — | — | — | — | — |
| 1526 | Herring oil acid | C | d | 8 | 192–215/0.06 | — | — | — | — | — | — |
| 1527 | Cod oil acid | B | b | 18 | 188–216/0.05 | — | — | — | — | — | — |
| 1528 | Sardine oil acid | B | b | 18 | 189–209/0.04 | — | — | — | — | — | — |
| 1529 | Shark oil acid | A | b | 15 | 187–216/0.06 | — | — | — | — | — | — |
| 1530 | Whale oil acid | F | a | 20 | 189–217/0.06 | — | — | — | — | — | — |

A solution of 16 g. of linoleic acid, 9.5 g. of dicyclohexylamine and 0.5 g. of p-toluenesulfonic acid in 100 ml. of toluene was reacted for 8 hours using a water separator. The reaction product was washed with 5% NaOH water, 5% HCl water and water, and was then dried and concentrated, and the residue was distilled to obtain 18.6 g. of a desired product, b.p. 205°–208° C./0.06 mmHg, $n_D^{25}$ 1.4882. Elementary analysis:

| | Theoretical | Analytical |
|---|---|---|
| C (%) | 81.20 | 79.99 |
| H (%) | 12.04 | 11.95 |
| N (%) | 3.16 | 3.31 |

Examples 1506–1530 are shown in the following table, in which:
Catalytic assistant:
A. p-Toluenesulfonic acid
B. p-Toluenesulfonic acid chloride
C. Sulfuric acid
D. Phenolsulfonic acid
E. IRA-400
F. Amberlist-15
Solvent:
a. Toluene
b. Pyridine
c. Benzene
d. Chloroform

EXAMPLE 1531

A mixture of 16 g. of linoleic acid and 9.5 g. of dicyclohexylamine was heated at 180° C. for 28 hours. The reaction product was immediately distilled to obtain 18.0 g. of a desired product, b.p. 206°–211° C./0.04 mmHg, $n_D^{28}$ 1.4880. Elementary analysis:

| | Theoretical | Analytical |
|---|---|---|
| C (%) | 31.20 | 80.99 |
| H (%) | 12.04 | 11.98 |
| N (%) | 3.16 | 3.14 |

EXAMPLE 1532

A mixture of 16 g. of methyl linoleate and 13 g. of dicyclohexylamine was reacted at 200° C. for 100 hours, and methanol was removed by distillation out of the reaction system. The reaction product was immediately distilled to obtain 12.0 g. of a desired product, b.p. 205°–213° C./0.05 mmHg. $n_D^{28}$ 1.4875. Elmentary analysis:

| | Theoretical | Analytical |
|---|---|---|
| C (%) | 81.20 | 80.97 |
| H (%) | 12.04 | 12.00 |

-continued

| | Theoretical | Analytical |
|---|---|---|
| N (%) | 3.16 | 3.08 |

Examples 1534–1548, carried out according to Examples 1531, 1532 and 1533, are shown in the following table:

| Example No. | Acid | b.p. °C./mmHg | C % Theoretical | C % Analytical | H % Theoretical | H % Analytical | N % Theoretical | N % Analytical |
|---|---|---|---|---|---|---|---|---|
| 1534 | Oleic acid | 200–209/0.06 | 80.83 | 80.75 | 12.44 | 12.34 | 3.14 | 3.18 |
| 1535 | Linolenic acid | 206–209/0.06 | 81.57 | 81.67 | 11.64 | 11.48 | 3.17 | 3.07 |
| 1536 | Safflower oil acid | 195–206/0.06 | — | — | — | — | — | — |
| 1537 | Cottonseed oil acid | 198–218/0.06 | — | — | — | — | — | — |
| 1538 | Sesame oil acid | 196–207/0.06 | — | — | — | — | — | — |
| 1539 | Castor oil acid | 191–214/0.05 | — | — | — | — | — | — |
| 1540 | Cuttlefish oil acid | 198–214/0.06 | — | — | — | — | — | — |
| 1541 | Mackerel oil acid | 192–215/0.05 | — | — | — | — | — | — |
| 1542 | Flatfish oil acid | 195–208/0.06 | — | — | — | — | — | — |
| 1543 | Saury pike oil acid | 196–214/0.06 | — | — | — | — | — | — |
| 1544 | Herring oil acid | 192–218/0.06 | — | — | — | — | — | — |
| 1545 | Cod oil acid | 188–215/0.05 | — | — | — | — | — | — |
| 1546 | Sardine oil acid | 189–208/0.04 | — | — | — | — | — | — |
| 1547 | Shark oil acid | 187–215/0.06 | — | — | — | — | — | — |
| 1548 | Whale oil acid | 189–219/0.06 | — | — | — | — | — | — |

EXAMPLE 1533

To a solution of 14 g. of linoleic acid and 5.5 g. of triethylamine in 100 cc. of tetrahydrofuran was added, 5.9 g. of ethyl chloroformate dropwise under stirring at −10° to −5° C. The stirring was further continued at −5° C. for additional 20 minutes, and then 9.5 g. of dicyclohexylamine was added dropwise under stirring at −5° C. Treatment is in the same manner as in Example 397. Yield: 16.2 g. b.p. 204°–213° C./0.02 mmHg, $n_D^{23}$ 1.4888. Elementary analysis:

| | Theoretical | Analytical |
|---|---|---|
| C (%) | 81.20 | 80.98 |
| H (%) | 12.04 | 11.98 |
| N (%) | 3.16 | 3.18 |

EXAMPLE 1549

To a mixture of 9.3 g. of dicyclohexylamine, 100 ml. of anhydrous ether and 4 g. of trimethylamine was added a solution of 16 g. of linoleic acid chloride in 20 ml. of anhydrous ether under stirring at 0° – 5° C. The reaction mixture was stirred at room temperature for 2 hours and allowed to stand overnight and boiled for 2 hours. Subsequently, the ether solution was washed with 5% HCl water, 5% NaOH water and water, and dried over anhydrous sodium sulfate and concentrated and distilled to obtain 17 g. of a desired product, b.p. 202°–207° C./0.06 mmHg, $n_D^{25}$ 1.4878. Elementary analysis:

| | Theoretical | Analytical |
|---|---|---|
| C (%) | 81.20 | 79.99 |
| H (%) | 12.04 | 12.02 |
| N (%) | 3.16 | 3.12 |

Examples 1550–1568 are shown in the following table:

| Example No. | Chloride Acid | Condensing agent | Solvent | b.p. °C./mmHg |
|---|---|---|---|---|
| 1550 | Linoleic acid | NaOH | H₂O Dioxane | 203–208/0.07 |
| 1551 | " | K₂CO₃ | Methylisobutyl-ketone | 203–208/0.07 |
| 1552 | " | Excess of 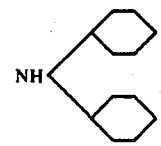 | Benzene | 200–206/0.08 |
| 1553 | " | Na₂CO₃ | Acetone | 205–210/0.08 |
| 1554 | " | KOH | Toluene | 204–209/0.07 |
| 1555 | Safflower oil acid | NaOH | H₂O-dioxane | 198–210/0.06 |
| 1556 | Linolenic acid | NaOH | H₂O-tetrahydrofuran | 204–209/0.05 |
| 1557 | " | K₂CO₃ | Acetone | 206–210/0.05 |
| 1558 | Oleic acid | N(CH₃)₃ | Benzene | 200–206/0.06 |
| 1559 | Cuttlefish oil | NaOH | H₂O-dioxane | 200–215/0.06 |
| 1560 | Mackeral oil | NaOH | H₂O-dioxane | 201–216/0.06 |

-continued

| Example No. | Chloride Acid | Condensing agent | Solvent | b.p. °C./mmHg |
|---|---|---|---|---|
| 1561 | Flatfish oil | NaOH | $H_2O$-dioxane | 200–208/0.03 |
| 1562 | Saury pike oil | NaOH | $H_2O$-dioxane | 192–210/0.08 |
| 1563 | Herring oil | $K_2CO_3$ | Methylisobutyl-ketone | 194–211/0.07 |
| 1564 | Cod oil | N(Et)$_3$ | Ether | 198–214/0.06 |
| 1565 | Sardine oil | pyridine | Toluene | 200–216/0.05 |
| 1566 | Shark oil | N,N-dimethylaniline | Dimethylformamide | 198–217/0.07 |
| 1567 | Liver oil | NaOH | $H_2O$-tetrahydrofuran | 194–220/0.07 |
| 1568 | Residual oil | NaOH | $H_2O$-dioxane | 193–264/0.07 |

| Example No. | $n_D^{25}$ | C (%) Theoretical | C (%) Analytical | H (%) Theoretical | H (%) Analytical | N (%) Theoretical | N (%) Analytical |
|---|---|---|---|---|---|---|---|
| 1550 | 1.4878 | 81.20 | 81.09 | 12.04 | 12.00 | 3.16 | 3.21 |
| 1551 | 1.4878 | 81.20 | 81.14 | 12.04 | 12.01 | 3.16 | 3.21 |
| 1552 | 1.4875 | 81.20 | 81.13 | 12.04 | 12.00 | 3.16 | 3.28 |
| 1553 | 1.4877 | 81.20 | 81.10 | 12.04 | 12.03 | 3.16 | 3.18 |
| 1554 | 1.4878 | 81.20 | 81.09 | 12.04 | 12.01 | 3.16 | 3.17 |
| 1555 | 1.4865 | — | — | — | — | — | — |
| 1556 | 1.4881 | 81.57 | 81.39 | 11.64 | 11.58 | 3.17 | 3.15 |
| 1557 | 1.4883 | 81.57 | 81.45 | 11.64 | 11.59 | 3.17 | 3.15 |
| 1558 | 1.4874 | 80.83 | 80.80 | 12.44 | 12.38 | 3.14 | 3.09 |
| 1559 | 1.4890 | — | — | — | — | — | — |
| 1560 | 1.4895 | — | — | — | — | — | — |
| 1561 | 1.4896 | — | — | — | — | — | — |
| 1562 | 1.4893 | — | — | — | — | — | — |
| 1563 | 1.4880 | — | — | — | — | — | — |
| 1564 | 1.4782 | — | — | — | — | — | — |
| 1565 | 1.4888 | — | — | — | — | — | — |
| 1566 | 1.4873 | — | — | — | — | — | — |
| 1567 | 1.4869 | — | — | — | — | — | — |
| 1568 | 1.4889 | — | — | — | — | — | — |

EXAMPLE 1569

A mixture of 12 g. of linoleic acid, 10 g. of dicyclohexyl carbodiimide, and 6 g. of adamantylamine in 40 ml. of benzene was allowed to stand overnight at room temperature. The mixture was added 3 ml. of acetic acid and was then filtered. The filtrate was washed with 5% hydrochloric acid water, 5% sodium carbonate water and water and was then dried over anhydrous sodium sulfate, and concentrated and distilled to obtain 15.3 g. of a desired product, b.p. 188°–190° C./0.03 mmHg, $n_D^{30}$ 1.4888 (Yield 86.9%). Elementary analysis:

|  | Theoretical | Analytical |
|---|---|---|
| C (%) | 81.29 | 81.56 |
| H (%) | 11.45 | 11.90 |
| N (%) | 3.39 | 3.72 |

EXAMPLE 1570

A mixture of 12 g. of stearic acid, 10 g. of diisopropyl carbodiimide and 6 g. of adamantylamine in 20 ml. of tetrahydrofuran were treated in the same manner as in Example 1569 to obtain 13.9 g. of a desired product, b.p. 188°–184° C./0.03 mmHg, (Yield 79.0%). Elementary analysis:

|  | Theoretical | Analytical |
|---|---|---|
| C (%) | 80.51 | 80.88 |
| H (%) | 12.31 | 11.95 |
| N (%) | 3.35 | 3.48 |

EXAMPLE 1571

A mixture of 12 g. of oleic acid, 10 g. of diphenyl carbodiimide and 6 g. of adamantylamine in 20 ml. of methyl acetate was treated in the same manner as in Example 1569 to obtain 15.1 g. of a desired product, b.p. 187°–189° C./0.03 mmHg. (Yield 85.8%). Elementary analysis:

|  | Theoretical | Analytical |
|---|---|---|
| C (%) | 80.91 | 80.52 |
| H (%) | 12.31 | 12.66 |
| N (%) | 3.35 | 3.70 |

EXAMPLE 1572

A mixture of 12 g. of linoleic acid, 10 g. of dibenzyl carbodiimide and 6 g. of adamantylamine in 40 ml. of chloroform was treated in the same manner as in Example 1569 to obtain 14.3 g. of a desired product, b.p. 188°–191° C./0.03 mmHg. Elementary analysis:

|   | Theoretical | Analytical |
|---|---|---|
| C (%) | 81.69 | 81.99 |
| H (%) | 11.02 | 10.94 |
| N (%) | 3.40 | 3.65 |

EXAMPLE 1573

A mixture of 12 g. of a mixed fatty acid obtained by hydrolysis of corn oil, a solution of 10 g. of dicyclohexyl carbodiimide in 20 ml. of benzene and a solution of 6 g. of adamantylamine in 10 ml. of benzene was treated in the same manner as in Example 1569 to obtain 10.8 g. of a desired product, b.p. 180°–196° C./0.03 mmHg.

EXAMPLE 1574

A mixture of 12 g. of a mixed fatty acid obtained by hydrolysis of cod oil, a solution of 10 g. of dicyclohexyl carbodiimide in 20 ml. of tetrahydrofuran and a solution of 6 g. of adamantylamine in 10 ml. of tetrahydrofuran was treated in the same manner as in Example 1569 to obtain 11.2 g. of a desired product, b.p. 176°–199° C./0.03 mmHg.

EXAMPLE 1575

A mixture of 10 g. of linoleic acid, 6 g. of adamantylamine, 2 g. of IRA-400 and 50 ml. of toluene was boiled with stirring for about 8 hours, using a water separator. Subsequently, the mixture was washed with 5% HCl water, 5% $Na_2CO_3$ water and water to obtain 4.8 g. of a desired product, b.p. 189°–190° C./0.04 mmHg, $n_D^{24}$ 1.4892. Elementary analysis:

|   | Theoretical | Analytical |
|---|---|---|
| C (%) | 81.29 | 81.35 |
| H (%) | 11.45 | 11.58 |
| N (%) | 3.39 | 3.61 |

EXAMPLE 1576

A mixture of 10 g. of oleic acid, 6 g. of adamantylamine and 3 g. of p-toluenesulfonic acid chloride was boiled for 4 hours in 20 ml. of pyridine. After removing the solvent, the mixture was washed by acid, alkali and water and was then distilled to obtain 8.0 g. of a desired product, b.p. 188°–192° C./0.03 mmHg. Elementary analysis:

|   | Theoretical | Analytical |
|---|---|---|
| C (%) | 80.91 | 81.21 |
| H (%) | 12.31 | 12.09 |
| N (%) | 3.35 | 3.52 |

EXAMPLE 1577

A mixture of 5 g. of oleic acid, 3 g. of adamantylamine and a small amount of p-toluenesulfonic acid in 20 ml. of toluene was boiled for 8 hours, using a water separator. The reaction product was washed with acid, alkali and water and was then distilled to obtain 4.7 g. of a desired product, b.p. 188°–191° C./0.03 mmHg. Elementary analysis:

|   | Theoretical | Analytical |
|---|---|---|
| C (%) | 80.91 | 81.23 |
| H (%) | 12.31 | 12.09 |
| N (%) | 3.35 | 3.62 |

EXAMPLE 1578

A mixture of 10 g. of adamantylamine and linoleic acid was heated in a distilling flask at 200° C. for about 1 hour, and was then distilled to obtain 6 g. of a desired product, b.p. 188°–192° C./0.04 mmHg, $n_D^{24}$ 1.4892. Elementary analysis:

|   | Theoretical | Analytical |
|---|---|---|
| C (%) | 81.29 | 81.31 |
| H (%) | 11.45 | 11.67 |
| N (%) | 3.39 | 3.29 |

EXAMPLE 1579

A mixture of 8 g. of soybean oil and 3 g. of adamantylamine was heated with stirring at 150° C. for 40 hours in a nitrogen atmosphere and was then distilled to obtain 10 g. of a desired product, b.p. 178°–192° C./0.03 mmHg.

EXAMPLE 1580

A mixture of 8 g. of safflower oil, 3 g. of adamantylamine and 0.6 g. of sodium methoxide was heated at 100° C. for 2 hours. In this case, methanol was distilled off out of the system. The reaction mixture was dissolved in ether, and the solution was washed with 5% HCl water, 5% $Na_2CO_3$ and water and was then dried and concentrated to obtain 10 g. of a desired product, b.p. 180°–193° C./0.04 mmHg.

EXAMPLE 1581

A solution of 8 g. of cuttlefish oil, 3 g. of adamantylamine and 0.8 g. of potassium t-butoxide in 50 ml. of benzene was boiled for 2 hours. The reaction mixture was washed with 5% HCl water, 5% $Na_2CO_3$ and water and was then dried, concentrated and distilled to obtain 8.3 g. of a desired product, b.p. 172°–202° C./0.04 mmHg.

EXAMPLE 1582

A mixture of 10 g. of linoleic anhydride, 5 g. of adamantylamine and 20 ml. of tetrahydrofuran was allowed to stand overnight. Subsequently, the mixture was washed with acid, alkali and water and was then distilled to obtain 4.2 g. of a desired product, b.p. 188°–190° C./0.03 mmHg, $n_D^{24}$ 1.4891. Elementary analysis:

|       | Theoretical | Analytical |
|-------|-------------|------------|
| C (%) | 81.29       | 81.40      |
| H (%) | 11.45       | 11.59      |
| N (%) | 3.39        | 3.38       |

EXAMPLE 1583

To a mixture of 6 g. adamantylamine, 6 g. of potassium carbonate and 50 ml. of methyl-i-butylketone was added 11 g. of linoleic acid chloride. The mixture was allowed to stand overnight at room temperature, and was then heated with stirring at 50° C. for 2 hours. Subsequently, the reaction mixture was washed with 5% hydrochloric acid water, 5% sodium bicarbonate water and water and was then dried, concentrated and distilled to obtain 13.1 g. of a desired product, b.p. 188°–191° C./0.05 mmHg, $n_D^{24}$ 1.4892. Elementary analysis:

|       | Theoretical | Analytical |
|-------|-------------|------------|
| C (%) | 81.29       | 81.31      |
| H (%) | 11.45       | 11.67      |
| N (%) | 3.39        | 3.29       |

EXAMPLE 1584

Palmitic acid chloride (10 g.) was added dropwise at 2°–5° C. to a solution of 5 g. of adamantylamine and 3.2 g. of pyridine in 50 ml. of benzene. Subsequently, the mixture was treated in the same manner as in Example 1569 to obtain 10.5 g. of a desired product, b.p. 183°–186° C./0.02 mmHg. Elementary analysis:

|       | Theoretical | Analytical |
|-------|-------------|------------|
| C (%) | 80.14       | 80.40      |
| H (%) | 12.16       | 12.09      |
| N (%) | 3.60        | 3.47       |

EXAMPLE 1585

Linoleic acid chloride (10 g.) was added dropwise to a solution of 6 g. of adamantylamine and 2 g. of caustic soda in a water-dioxane. Thereafter, the same treatments as in Example 1569 were effected to obtain 11.2 g. of a desired product. b.p. 188°–192° C./0.03 mmHg. Elementary analysis:

|       | Theoretical | Analytical |
|-------|-------------|------------|
| C (%) | 81.69       | 81.87      |
| H (%) | 11.02       | 10.81      |
| N (%) | 3.40        | 3.51       |

EXAMPLE 1586

Oleic acid chloride (10 g.) was added dropwise to a solution of 5 g. of adamantylamine in 30 ml. of trimethylamine. Thereafter, the same treatments as in Example 1569 were effected to obtain 10.1 g. of a desired product, b.p. 185°–188° C./0.02 mmHg. Elementary analysis:

|       | Theoretical | Analytical |
|-------|-------------|------------|
| C (%) | 80.91       | 81.05      |
| H (%) | 12.31       | 12.19      |
| N (%) | 3.35        | 3.41       |

EXAMPLE 1587

Safflower oil fatty acid chloride (10 g.) was added 5 g. of adamantylamine in the same manner as in Example 1569 to obtain 9.8 g. of a desired product, b.p. 180°–194° C./0.04 mmHg.

EXAMPLE 1588

Sardine oil fatty acid chloride (10 g.) was added to 5 g. of adamantylamine in the same manner as in Example 1569 to obtain 9.3 g. of a desired product, b.p. 164°–208° C./0.05 mmHg.

EXAMPLE 1589

A mixture of 10 g. of t-butyl linoleate and 10 g. of adamantylamine was stirred in a nitrogen atmosphere at 150° C. for 40 hours, and then the mixture was distilled to obtain 13.0 g. of a desired product, b.p. 185°–186° C./0.02 mmHg, $n_D^{30}$ 1.4889 (Yield 87.8%) Elementary analysis:

|       | Theoretical | Analytical |
|-------|-------------|------------|
| C (%) | 81.29       | 81.55      |
| H (%) | 11.45       | 11.71      |
| N (%) | 3.39        | 3.69       |

EXAMPLE 1590

A mixture of 10 g. of methyl linoleate, 5.5 g. of adamentylamine and 2 g. of sodium methylate was heated with stirring at 100° C. for 1 hour, the methanol was distilled off out of the reaction system. The reaction product was dissolved in ether and the ether layer was washed with water, dried, concentrated and distilled to obtain 13.0 g. of desired product, b.p. 188°–189° C./0.03 mmHg, $n_D^{32}$ 1.4884 (Yield 87.8%) Elementary analysis:

|       | Theoretical | Analytical |
|-------|-------------|------------|
| C (%) | 81.29       | 81.09      |
| H (%) | 11.45       | 11.59      |
| N (%) | 3.39        | 3.48       |

EXAMPLE 1591

A mixture of 10 g. of methyl oleate and 6 g. of adamantylamine were heated with stirring at 140° C. for about 50 hours, and then the mixture was distilled to obtain a desired product, b.p. 188°–192° C./0.03 mmHg. Elementary analysis:

|       | Theoretical | Analytical |
|-------|-------------|------------|
| C (%) | 80.91       | 81.09      |
| H (%) | 12.91       | 12.18      |
| N (%) | 3.35        | 3.51       |

EXAMPLE 1592

A mixture of 10 g. of methyl palmitate, 6 g. of adamentylamine, 50 ml. of benzene and 2 g. of sodium ethylate was refluxed for 2 hours to obtain a desired product, b.p. 182°–186° C./0.03 mmHg. Elementary analysis:

|  | Theoretical | Analytical |
|---|---|---|
| C (%) | 80.14 | 80.31 |
| H (%) | 12.16 | 12.05 |
| N (%) | 3.60 | 3.51 |

EXAMPLE 1593

A mixture of 10 g. of safflower oil methyl ester and 6 g. of adamentylamine was heated at 150° C. for 50 hours and was then distilled to obtain 11.2 g. of a desired product, b.p. 177°–199° C./0.03 mmHg.

EXAMPLE 1594

A mixture of 10 g. of ethyl ester of cod oil and 6 g. of adamentylamine was heated at 150° C. for 40 hours to obtain 9.2 g. of a desired product, b.p. 168°–213° C./0.03 mmHg.

Following amides are also synthesized according to the above mentioned methods.

| | $n_D$ | C % Theoretical | C % Analytical | H % Theoretical | H % Analytical | N % Theoretical | N % Analytical |
|---|---|---|---|---|---|---|---|
| $C_{17}H_{31}CONHCH(CH_3)$–C$_6$H$_4$–NO$_2$ (d) | 23°1.5120 | 72.86 | 72.90 | 9.41 | 9.27 | 6.54 | 6.44 |
| $C_{17}H_{31}CONHCH(CH_3)$–C$_6$H$_4$–NO$_2$ (l) | 22°1.5118 | 72.86 | 72.95 | 9.41 | 9.22 | 6.54 | 6.43 |
| $C_{17}H_{33}CONHCH(C_2H_5)$–C$_6$H$_4$–NO$_2$ (d) | 32°1.5123 | 72.93 | 73.12 | 9.97 | 10.07 | 6.30 | 6.19 |
| $C_{17}H_{33}CONHCH(C_2H_5)$–C$_6$H$_4$–NO$_2$ (l) | 33°1.5122 | 72.93 | 73.10 | 9.97 | 10.05 | 6.30 | 6.15 |
| $C_{17}H_{29}CONHCH(C_2H_5)$–C$_6$H$_4$–NO$_2$ (d) | 32°1.5012 | 73.60 | 73.82 | 9.15 | 9.28 | 6.36 | 6.18 |
| $C_{17}H_{29}CONHCH(C_2H_5)$–C$_6$H$_4$–NO$_2$ (l) | 30°1.5020 | 73.60 | 73.76 | 9.15 | 9.22 | 9.36 | 6.22 |
| Iso—$C_{17}H_{35}CONHCH(CH_3)$–C$_6$H$_4$–NO$_2$ (dl) | 27°1.5163 | 72.18 | 72.00 | 10.25 | 10.09 | 6.48 | 6.52 |
| Safflower—CONHCH(CH$_3$)–C$_6$H$_4$–NO$_2$ (d) | 24°1.5140 | | | | | | |
| Safflower—CONHCH(CH$_3$)–C$_6$H$_4$–NO$_2$ (l) | 20°1.5142 | | | | | | |
| Sardine—CONHCH(CH$_3$)–C$_6$H$_4$–NO$_2$ (d) | 21°1.5222 | | | | | | |
| Sardine—CONHCH(CH$_3$)–C$_6$H$_4$–NO$_2$ (l) | 23°1.5220 | | | | | | |

| | b.p. ° C.mmHg. | C % Theoretical | C % Analysis | H % Theoretical | H % Analysis | N % Theoretical | N % Analysis |
|---|---|---|---|---|---|---|---|
| $C_{17}H_{31}CONH$–CH(CH$_3$)–C$_6$H$_4$–OCH$_3$ (d) | 214–223°/0.04 | 78.40 | 78.49 | 10.48 | 10.66 | 3.39 | 3.33 |
| $C_{17}H_{31}CONHCH(CH_3)$–C$_6$H$_4$–OCH$_3$ (l) | 214–224/0.04 | 78.40 | 78.53 | 10.48 | 10.68 | 3.39 | 3.20 |
| $C_{17}H_{33}CONHCH(CH_3)$–C$_6$H$_4$–OCH$_3$ (dl) | 210–221/0.03 | 78.02 | 78.20 | 10.91 | 11.05 | 3.37 | 3.27 |

-continued

| | b.p. °C.mmHg. | C % Theoretical | C % Analysis | H % Theoretical | H % Analysis | N % Theoretical | N % Analysis |
|---|---|---|---|---|---|---|---|
| $C_{17}H_{33}CONHCH(CH_3)$-C$_6$H$_4$-OCH$_3$ (d) | 213–223/0.03 | 78.02 | 78.21 | 10.91 | 11.16 | 3.37 | 3.22 |
| $C_{17}H_{33}CONHCH(CH_3)$-C$_6$H$_4$-OCH$_3$ (l) | 213–225/0.03 | 78.02 | 78.19 | 10.91 | 11.09 | 3.37 | 3.30 |
| iso-$C_{17}H_{35}CONHCH(CH_3)$-C$_6$H$_4$-OCH$_3$ (d) | 218–228/0.04 | 77.64 | 77.77 | 11.34 | 11.50 | 3.35 | 3.50 |
| iso-$C_{17}H_{35}CONHCH(CH_3)$-C$_6$H$_4$-OCH$_3$ (l) | 216–228/0.03 | 77.64 | 77.80 | 11.34 | 11.48 | 3.35 | 3.52 |
| $C_{17}H_{29}CONHCH(C_2H_5)$-C$_6$H$_4$-OCH$_3$ (d) | 217–225/0.05 | 79.61 | 79.42 | 10.18 | 10.12 | 3.29 | 3.40 |
| $C_{17}H_{29}CONHCH(C_2H_5)$-C$_6$H$_4$-OCH$_3$ (l) | 217–227/0.05 | 79.61 | 79.53 | 10.18 | 10.20 | 3.29 | 3.38 |
| Safflower oil—CONHCH(CH$_3$)-C$_6$H$_4$-OCH$_3$ (l) | 208–227/0.04 | | | | | | |
| Sardine oil—CONHCH(CH$_3$)-C$_6$H$_4$-OCH$_3$ (l) | 210–227/0.03 | | | | | | |

| | | C % Theoretical | C % Analytical | H % Theoretical | H % Analytical | N % Theoretical | N % Analytical |
|---|---|---|---|---|---|---|---|
| $C_{17}H_{33}CONHCH(CH_2C_6H_5)$-C$_6$H$_5$ (d) | Semi solid | 83.24 | 83.33 | 10.26 | 10.45 | 3.03 | 3.31 |
| $C_{17}H_{33}CONHCH(CH_2C_6H_5)$-C$_6$H$_5$ (l) | " | 83.24 | 83.40 | 10.26 | 10.39 | 3.03 | 2.94 |
| $C_{17}H_{29}CONHCH(CH_2C_6H_5)$-C$_6$H$_5$ (d) | " | 83.97 | 84.01 | 9.47 | 9.67 | 3.06 | 3.00 |
| $C_{17}H_{29}CONHCH(CH_2C_6H_5)$-C$_6$H$_5$ (l) | " | 83.97 | 84.13 | 9.47 | 9.53 | 3.06 | 2.99 |
| $C_{17}H_{29}CONHCH(CH_2C_6H_5)$-C$_6$H$_5$ (d) | " | 83.97 | 84.22 | 9.47 | 9.57 | 3.06 | 3.21 |

-continued

| | | C % Theoretical | C % Analytical | H % Theoretical | H % Analytical | N % Theoretical | N % Analytical |
|---|---|---|---|---|---|---|---|
| Sardine oil-CONHCH(d)(-C₆H₅)-CH₂-C₆H₅ | ″ | | | | | | |
| Sardine oil-CONHCH(l)(-C₆H₅)-CH₂-C₆H₅ | ″ | | | | | | |

| | | C % Theoretical | C % Analysis | H % Theoretical | H % Analysis | N % Theoretical | N % Analysis |
|---|---|---|---|---|---|---|---|
| C₁₇H₃₃CONHCH(d)(-C₆H₄-Br)-CH₃ | 222–236°/0.08 | 67.24 | 67.40 | 9.05 | 8.97 | 3.01 | 2.78 |
| C₁₇H₃₃CONHCH(l)(-C₆H₄-Br)-CH₃ | 219–223/0.03 | 67.24 | 67.38 | 9.05 | 9.15 | 3.01 | 2.84 |
| Iso-C₁₇H₃₅CONHCH(l)(-C₆H₄-Cl)-CH₃ | 215–230/0.05 | 74.02 | 74.20 | 10.43 | 10.65 | 3.32 | 3.19 |
| Iso-C₁₇H₃₅CONHCH(d)(-C₆H₄-Cl)-CH₃ | 214–232/0.05 | 74.02 | 74.21 | 10.43 | 10.67 | 3.32 | 3.30 |
| C₁₇H₂₉CONHCH(l)(-C₆H₄-Cl)-CH₃ | 205–217/0.05 | 75.09 | 75.24 | 9.14 | 9.33 | 3.36 | 3.29 |
| C₁₇H₂₉CONHCH(d)(-C₆H₄-Cl)-CH₃ | 209–219/0.04 | 75.09 | 75.30 | 9.14 | 9.30 | 3.36 | 3.28 |
| Safflower oil-CONHCH(d)(-C₆H₄-Br)-C₂H₅ | 215–224/0.03 | | | | | | |
| Safflower oil-CONHCH(l)(-C₆H₄-Br)-C₂H₅ | 213–225/0.03 | | | | | | |
| Flatfish oil-CONHCH(l)(-C₆H₄-Cl)-C₂H₅ | 190–232/0.04 | | | | | | |
| Flatfish oil-CONHCH(d)(-C₆H₄-Cl)-C₂H₅ | 192–228/0.03 | | | | | | |

| | | C % Theoretical | C % Analytical | H % Theoretical | H % Analytical | N % Theoretical | N % Analytical |
|---|---|---|---|---|---|---|---|
| C₁₇H₃₃CONHCH(d)(-C₆H₄-C₂H₅)-CH₃ | 200–218/0.05 | 81.29 | 81.43 | 11.45 | 11.55 | 3.39 | 3.22 |

-continued

| | | C % | | H % | | N % | |
|---|---|---|---|---|---|---|---|
| | | Theoretical | Analytical | Theoretical | Analytical | Theoretical | Analytical |
| $C_{17}H_{33}CONHCH(CH_3)$—C$_6$H$_4$—$C_2H_5$ (l) | 200–215/0.05 | 81.29 | 81.50 | 11.45 | 11.62 | 3.39 | 3.21 |
| Iso-$C_{17}H_{35}CONHCH(CH_3)$—C$_6$H$_4$—$CH_3$ (d) | 198–215/0.06 | 80.72 | 80.91 | 11.83 | 12.02 | 3.49 | 3.42 |
| Iso-$C_{17}H_{35}CONHCH(CH_3)$—C$_6$H$_4$—$CH_3$ (l) | 196–215/0.06 | 80.73 | 80.88 | 11.83 | 12.07 | 3.49 | 3.39 |
| $C_{17}H_{29}CONHCH(CH_3)$—C$_6$H$_4$—$CH_3$ (d) | 210–221/0.04 | 81.97 | 82.14 | 10.45 | 10.62 | 3.54 | 3.47 |
| $C_{17}H_{29}CONHC(CH_3)$—C$_6$H$_4$—$CH_3$ (l) | 209–218/0.04 | 81.97 | 82.13 | 10.45 | 10.55 | 3.54 | 3.39 |
| Safflower oil-CONHCH(CH$_3$)—C$_6$H$_4$—$CH_3$ (d) | 200–212°/0.03 | | | | | | |
| Safflower oil-CONHCH(CH$_3$)—C$_6$H$_4$—$CH_3$ (l) | 200–214/0.03 | | | | | | |
| Herring oil-CONHCH(CH$_3$)—C$_6$H$_3$(CH$_3$) (d) | 194–227/0.04 | | | | | | |
| Herring oil-CONHCH(CH$_3$)—C$_6$H$_3$(CH$_3$) (l) | 190–226/0.04 | | | | | | |

What is claimed is:

1. A composition consisting essentially of a cholesterol lowering pharmaceutically effective amount of a compound of the formula,

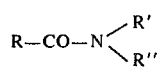

wherein R is a $C_{13}$–$C_{25}$ aliphatic hydrocarbon chain or a $C_{13}$–$C_{25}$ hydroxylated aliphatic hydrocarbon chain, R' is racemic-, d- or l-α-benzylbenzyl, and R'' is hydrogen, and a solid or liquid pharmaceutically acceptable carrier.

2. A method of lowering cholesterol content in patients having an elevated cholesterol level, which comprises orally administering 0.1 to 20 grams per day of a compound of the formula,

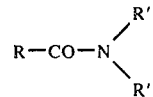

wherein R is a $C_{13}$–$C_{25}$ aliphatic hydrocarbon chain or a $C_{13}$–$C_{25}$ hydroxylated aliphatic hydrocarbon chain, R' racemic-, d- or l-α-benzylbenzyl, and R'' is hydrogen.

* * * * *